US007981065B2

(12) United States Patent
Westlund et al.

(10) Patent No.: US 7,981,065 B2
(45) Date of Patent: Jul. 19, 2011

(54) LEAD ELECTRODE INCORPORATING EXTRACELLULAR MATRIX

(75) Inventors: Randy Westlund, River Falls, WI (US); Jeffrey Ross, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1281 days.

(21) Appl. No.: 11/017,238

(22) Filed: Dec. 20, 2004

(65) Prior Publication Data

US 2006/0136027 A1 Jun. 22, 2006

(51) Int. Cl.
 *A61H 7/00* (2006.01)
(52) U.S. Cl. ........................................ 601/136; 601/137
(58) Field of Classification Search .......... 601/136–137; 607/51, 73
See application file for complete search history.

(56) References Cited

U.S. PATENT DOCUMENTS

| | | |
|---|---|---|
| 3,692,027 A | 9/1972 | Ellinwood, Jr. |
| 4,003,379 A | 1/1977 | Ellinwood, Jr. |
| 4,051,842 A | 10/1977 | Hazel et al. |
| 4,140,122 A | 2/1979 | Kuhl et al. |
| 4,146,029 A | 3/1979 | Ellinwood, Jr. |
| 4,202,340 A | 5/1980 | Langer et al. |
| 4,271,192 A | 6/1981 | Wurtman et al. |
| 4,281,664 A | 8/1981 | Duggan |
| 4,299,220 A | 11/1981 | Dorman |
| 4,383,529 A | 5/1983 | Webster |
| 4,470,987 A | 9/1984 | Wurtman et al. |
| 4,544,371 A | 10/1985 | Dormandy, Jr. et al. |
| 4,556,063 A | 12/1985 | Thompson et al. |
| 4,559,946 A | 12/1985 | Mower |
| 4,651,716 A | 3/1987 | Forester et al. |
| 4,674,518 A | 6/1987 | Salo |
| 4,677,989 A | 7/1987 | Robblee |
| 4,686,987 A | 8/1987 | Salo et al. |
| 4,693,253 A | 9/1987 | Adams |
| 4,787,389 A | 11/1988 | Tarjan |
| 4,790,317 A | 12/1988 | Davies |
| 4,871,351 A | 10/1989 | Feingold |
| 4,880,005 A | 11/1989 | Pless et al. |
| 4,897,987 A | 2/1990 | Spalla |
| 4,902,508 A | 2/1990 | Badylak et al. |
| 4,904,472 A | 2/1990 | Belardinelli et al. |
| 4,924,875 A | 5/1990 | Chamoun |
| 4,930,075 A | 5/1990 | Kortas |
| 4,938,231 A | 7/1990 | Milijasevic et al. |
| 4,940,054 A | 7/1990 | Grevis et al. |
| 4,944,299 A | 7/1990 | Silvian |
| 4,949,719 A | 8/1990 | Pless et al. |

(Continued)

FOREIGN PATENT DOCUMENTS

EP 0054138 A1 6/1982

(Continued)

OTHER PUBLICATIONS

Bader, A., et al., "Tissue Engineering of Heart Valves—Human Endothelial Cell Seeding of Detergent Acellularized Porcine Valves", *Eur J Cardiothorac Surg*, 14(3), (1998), 279-284.

(Continued)

*Primary Examiner* — Michael A. Brown
(74) *Attorney, Agent, or Firm* — Schwegman, Lundberg & Woessner, P.A.

(57) ABSTRACT

Implantable devices containing extracellular matrix and methods of using the devices are provided.

17 Claims, 14 Drawing Sheets

U.S. PATENT DOCUMENTS

| | | |
|---|---|---|
| 4,980,379 A | 12/1990 | Belardinelli et al. |
| 4,987,897 A | 1/1991 | Funke |
| 5,002,052 A | 3/1991 | Haluska |
| 5,014,698 A | 5/1991 | Cohen |
| 5,025,786 A | 6/1991 | Siegel |
| 5,031,621 A | 7/1991 | Grandjean et al. |
| 5,033,477 A | 7/1991 | Chin et al. |
| 5,040,533 A | 8/1991 | Fearnot |
| 5,041,107 A | 8/1991 | Heil, Jr. |
| 5,042,497 A | 8/1991 | Shapland |
| 5,058,581 A | 10/1991 | Silvian |
| 5,087,243 A | 2/1992 | Avitall |
| 5,103,821 A | 4/1992 | King |
| 5,109,842 A | 5/1992 | Adinolfi |
| 5,113,869 A | 5/1992 | Nappholz et al. |
| 5,127,404 A | 7/1992 | Wyborny et al. |
| 5,130,141 A | 7/1992 | Law et al. |
| 5,135,004 A | 8/1992 | Adams et al. |
| 5,137,019 A | 8/1992 | Pederson et al. |
| 5,179,945 A | 1/1993 | Hofwegen et al. |
| 5,179,946 A | 1/1993 | Weiss |
| 5,184,614 A | 2/1993 | Collins et al. |
| 5,188,105 A | 2/1993 | Keimel |
| 5,190,035 A | 3/1993 | Salo et al. |
| 5,193,535 A | 3/1993 | Bardy et al. |
| 5,199,428 A | 4/1993 | Obel et al. |
| 5,215,083 A | 6/1993 | Drane et al. |
| 5,220,917 A | 6/1993 | Cammilli et al. |
| 5,251,621 A | 10/1993 | Collins |
| 5,259,380 A | 11/1993 | Mendes et al. |
| 5,269,301 A | 12/1993 | Cohen |
| 5,275,826 A | 1/1994 | Badylak et al. |
| 5,282,836 A | 2/1994 | Kreyenhagen et al. |
| 5,284,136 A | 2/1994 | Hauck et al. |
| 5,292,338 A | 3/1994 | Bardy |
| 5,301,677 A | 4/1994 | Hsung |
| 5,305,745 A | 4/1994 | Zacouto |
| 5,312,453 A | 5/1994 | Shelton et al. |
| 5,314,430 A | 5/1994 | Bardy |
| 5,325,856 A | 7/1994 | Nitzsche et al. |
| 5,334,222 A | 8/1994 | Salo et al. |
| 5,342,408 A | 8/1994 | deCoriolis et al. |
| 5,346,506 A | 9/1994 | Mower et al. |
| 5,350,406 A | 9/1994 | Nitzsche et al. |
| 5,352,463 A | 10/1994 | Badylak et al. |
| 5,353,800 A | 10/1994 | Pohndorf et al. |
| 5,354,317 A | 10/1994 | Alt |
| 5,366,485 A | 11/1994 | Kroll et al. |
| 5,368,028 A | 11/1994 | Palti |
| 5,379,776 A | 1/1995 | Murphy et al. |
| 5,391,190 A | 2/1995 | Pederson et al. |
| 5,404,877 A | 4/1995 | Nolan et al. |
| 5,405,362 A | 4/1995 | Kramer et al. |
| 5,416,695 A | 5/1995 | Stutman et al. |
| 5,417,717 A | 5/1995 | Salo et al. |
| 5,423,883 A | 6/1995 | Helland |
| 5,431,682 A | 7/1995 | Hedberg |
| 5,435,999 A | 7/1995 | Austin |
| 5,439,483 A | 8/1995 | Duong-Van |
| 5,441,525 A | 8/1995 | Shelton et al. |
| 5,456,692 A | 10/1995 | Smith, Jr. et al. |
| 5,458,619 A | 10/1995 | Olson |
| 5,460,605 A | 10/1995 | Tuttle et al. |
| 5,464,434 A | 11/1995 | Alt |
| 5,476,503 A | 12/1995 | Yang |
| 5,486,359 A | 1/1996 | Caplan et al. |
| 5,487,752 A | 1/1996 | Salo et al. |
| 5,489,293 A | 2/1996 | Pless et al. |
| 5,496,360 A | 3/1996 | Hoffmann et al. |
| 5,499,971 A | 3/1996 | Shapland et al. |
| 5,500,008 A | 3/1996 | Fain |
| 5,501,701 A | 3/1996 | Markowitz et al. |
| 5,522,853 A | 6/1996 | Kroll |
| 5,531,768 A | 7/1996 | Alferness |
| 5,538,722 A | 7/1996 | Blau et al. |
| 5,540,723 A | 7/1996 | Ideker et al. |
| 5,540,728 A | 7/1996 | Shelton et al. |
| 5,543,318 A | 8/1996 | Smith et al. |
| 5,545,186 A | 8/1996 | Olson et al. |
| 5,545,205 A | 8/1996 | Schulte et al. |
| 5,551,953 A | 9/1996 | Lattin et al. |
| 5,554,174 A | 9/1996 | Causey, III |
| 5,554,389 A | 9/1996 | Badylak et al. |
| 5,556,421 A | 9/1996 | Prutchi et al. |
| 5,560,369 A | 10/1996 | McClure et al. |
| 5,560,370 A | 10/1996 | Verrier et al. |
| 5,562,711 A | 10/1996 | Yerich et al. |
| 5,562,713 A | 10/1996 | Silvian |
| 5,571,151 A | 11/1996 | Gregory |
| 5,579,876 A | 12/1996 | Adrian et al. |
| 5,580,779 A | 12/1996 | Smith et al. |
| 5,584,864 A | 12/1996 | White |
| 5,584,867 A | 12/1996 | Limousin et al. |
| 5,584,868 A | 12/1996 | Salo et al. |
| 5,586,556 A | 12/1996 | Spivey et al. |
| 5,591,215 A | 1/1997 | Greenhut et al. |
| 5,602,301 A | 2/1997 | Field |
| 5,603,331 A | 2/1997 | Heemels et al. |
| 5,605,159 A | 2/1997 | Smith et al. |
| 5,607,418 A | 3/1997 | Arzbaecher |
| 5,607,463 A | 3/1997 | Schwartz et al. |
| 5,609,629 A | 3/1997 | Fearnot et al. |
| 5,610,172 A | 3/1997 | Weidmann et al. |
| 5,613,495 A | 3/1997 | Mills et al. |
| 5,626,620 A | 5/1997 | Kieval et al. |
| 5,626,622 A | 5/1997 | Cooper |
| 5,626,623 A | 5/1997 | Kieval et al. |
| 5,632,267 A | 5/1997 | Hognelid et al. |
| 5,632,766 A | 5/1997 | Hsu |
| 5,634,899 A | 6/1997 | Shapland et al. |
| 5,662,689 A | 9/1997 | Elsberry et al. |
| 5,674,250 A | 10/1997 | de Coriolis et al. |
| 5,674,251 A | 10/1997 | Combs et al. |
| 5,674,255 A | 10/1997 | Walmsley et al. |
| 5,676,153 A | 10/1997 | Smith et al. |
| 5,676,686 A | 10/1997 | Jensen et al. |
| 5,681,735 A | 10/1997 | Emerson et al. |
| 5,683,424 A | 11/1997 | Brown et al. |
| 5,683,429 A | 11/1997 | Mehra |
| 5,690,682 A | 11/1997 | Buscemi et al. |
| 5,690,689 A | 11/1997 | Sholder |
| 5,693,075 A | 12/1997 | Plicchi et al. |
| 5,700,283 A | 12/1997 | Salo |
| 5,703,125 A | 12/1997 | Bovy et al. |
| 5,706,829 A | 1/1998 | Kadri |
| 5,709,215 A | 1/1998 | Perttu et al. |
| 5,713,929 A | 2/1998 | Hess et al. |
| 5,713,930 A | 2/1998 | van der Veen et al. |
| 5,713,932 A | 2/1998 | Gillberg et al. |
| 5,716,383 A | 2/1998 | Kieval et al. |
| 5,718,235 A | 2/1998 | Golosarsky et al. |
| 5,720,770 A | 2/1998 | Nappholz et al. |
| 5,725,561 A | 3/1998 | Stroebel et al. |
| 5,725,562 A | 3/1998 | Sheldon |
| 5,730,125 A | 3/1998 | Prutchi et al. |
| 5,730,141 A | 3/1998 | Fain et al. |
| 5,730,142 A | 3/1998 | Sun et al. |
| 5,733,727 A | 3/1998 | Field |
| RE35,779 E | 4/1998 | Alferness et al. |
| 5,738,096 A | 4/1998 | Ben-Haim |
| 5,741,304 A | 4/1998 | Patwardhan et al. |
| 5,741,308 A | 4/1998 | Sholder |
| 5,741,319 A | 4/1998 | Woloszko et al. |
| 5,749,900 A | 5/1998 | Schroeppel et al. |
| 5,749,901 A | 5/1998 | Bush et al. |
| 5,749,906 A | 5/1998 | Kieval et al. |
| 5,755,736 A | 5/1998 | Gillberg et al. |
| 5,755,737 A | 5/1998 | Prieve et al. |
| 5,755,739 A | 5/1998 | Sun et al. |
| 5,755,740 A | 5/1998 | Nappholz |
| 5,759,196 A | 6/1998 | Hess et al. |
| 5,772,604 A | 6/1998 | Langberg et al. |
| 5,776,164 A | 7/1998 | Ripart |
| 5,776,167 A | 7/1998 | Levine et al. |
| 5,782,876 A | 7/1998 | Flammang |
| 5,782,879 A | 7/1998 | Rosborough et al. |
| 5,782,887 A | 7/1998 | van Krieken et al. |

| Patent No. | Date | Inventor |
|---|---|---|
| 5,788,717 A | 8/1998 | Mann et al. |
| 5,792,193 A | 8/1998 | Stoop |
| 5,797,967 A | 8/1998 | KenKnight |
| 5,800,464 A | 9/1998 | Kieval |
| 5,800,471 A | 9/1998 | Baumann |
| 5,800,498 A | 9/1998 | Obino et al. |
| 5,814,077 A | 9/1998 | Sholder et al. |
| 5,814,081 A | 9/1998 | Ayers et al. |
| 5,814,085 A | 9/1998 | Hill |
| 5,817,131 A | 10/1998 | Elsberry et al. |
| 5,824,049 A | 10/1998 | Ragheb et al. |
| 5,833,603 A | 11/1998 | Kovacs et al. |
| 5,833,978 A | 11/1998 | Tremblay |
| 5,834,029 A | 11/1998 | Bellamkonda et al. |
| 5,836,935 A | 11/1998 | Ashton et al. |
| 5,836,975 A | 11/1998 | DeGroot |
| 5,836,987 A | 11/1998 | Baumann et al. |
| 5,840,079 A | 11/1998 | Warman et al. |
| 5,842,997 A | 12/1998 | Verrier et al. |
| 5,849,033 A | 12/1998 | Mehmanesh et al. |
| 5,855,610 A | 1/1999 | Vacanti et al. |
| 5,865,787 A | 2/1999 | Shapland et al. |
| 5,873,904 A | 2/1999 | Ragheb et al. |
| 5,874,420 A | 2/1999 | Pelleg |
| 5,876,353 A | 3/1999 | Riff |
| 5,879,295 A | 3/1999 | Li et al. |
| 5,885,797 A | 3/1999 | Chen et al. |
| 5,893,881 A | 4/1999 | Elsberry et al. |
| 5,899,928 A | 5/1999 | Sholder et al. |
| 5,902,324 A | 5/1999 | Thompson et al. |
| 5,909,924 A | 6/1999 | Roslund, Jr. |
| 5,913,879 A | 6/1999 | Ferek-Petric et al. |
| 5,914,242 A | 6/1999 | Honkanen et al. |
| 5,916,239 A | 6/1999 | Geddes et al. |
| 5,919,210 A | 7/1999 | Lurie et al. |
| 5,925,066 A | 7/1999 | Kroll et al. |
| 5,928,943 A | 7/1999 | Franz et al. |
| 5,945,577 A | 8/1999 | Stice et al. |
| 5,949,659 A | 9/1999 | Lesche |
| 5,957,861 A | 9/1999 | Combs et al. |
| 5,957,957 A | 9/1999 | Sheldon |
| 5,967,986 A | 10/1999 | Cimochowski et al. |
| 5,968,079 A | 10/1999 | Warman et al. |
| 5,978,705 A | 11/1999 | KenKnight et al. |
| 5,991,660 A | 11/1999 | Goyal |
| 5,991,668 A | 11/1999 | Leinders et al. |
| 6,005,009 A | 12/1999 | Murad et al. |
| 6,016,447 A | 1/2000 | Juran et al. |
| 6,016,448 A | 1/2000 | Busacker et al. |
| 6,021,350 A | 2/2000 | Mathson |
| 6,022,322 A | 2/2000 | Prutchi |
| 6,035,233 A | 3/2000 | Schroeppel et al. |
| 6,044,297 A | 3/2000 | Sheldon et al. |
| 6,048,722 A | 4/2000 | Farb et al. |
| 6,049,735 A | 4/2000 | Hartley et al. |
| 6,050,980 A | 4/2000 | Wilson |
| 6,059,726 A | 5/2000 | Lee et al. |
| 6,066,094 A | 5/2000 | Ben-Haim |
| 6,076,015 A | 6/2000 | Hartley et al. |
| 6,077,218 A | 6/2000 | Alferness |
| 6,078,834 A | 6/2000 | Lurie et al. |
| 6,083,930 A | 7/2000 | Roufa et al. |
| 6,085,754 A | 7/2000 | Alferness et al. |
| 6,090,622 A | 7/2000 | Gearhart et al. |
| 6,095,968 A | 8/2000 | Snyders |
| 6,096,070 A | 8/2000 | Ragheb et al. |
| 6,096,347 A | 8/2000 | Geddes et al. |
| 6,099,832 A | 8/2000 | Mickle et al. |
| 6,100,242 A | 8/2000 | Hammond |
| 6,104,949 A | 8/2000 | Pitts Crick et al. |
| 6,110,459 A | 8/2000 | Mickle et al. |
| 6,112,116 A | 8/2000 | Fischell et al. |
| 6,112,117 A | 8/2000 | KenKnight et al. |
| 6,114,164 A | 9/2000 | Dennis et al. |
| 6,115,636 A | 9/2000 | Ryan |
| 6,119,554 A | 9/2000 | Plankenhorn |
| 6,126,590 A | 10/2000 | Alferness |
| 6,128,526 A | 10/2000 | Stadler et al. |
| 6,135,976 A | 10/2000 | Tachibana et al. |
| 6,140,740 A | 10/2000 | Porat et al. |
| 6,151,525 A | 11/2000 | Soykan et al. |
| 6,152,955 A | 11/2000 | KenKnight et al. |
| 6,154,672 A | 11/2000 | Pendekanti et al. |
| 6,154,675 A | 11/2000 | Juran et al. |
| 6,155,267 A | 12/2000 | Nelson |
| 6,156,572 A | 12/2000 | Bellamkonda et al. |
| 6,161,042 A | 12/2000 | Hartley et al. |
| 6,165,164 A | 12/2000 | Hill et al. |
| 6,168,801 B1 | 1/2001 | Heil, Jr. et al. |
| 6,174,871 B1 | 1/2001 | Hammond et al. |
| 6,198,394 B1 | 3/2001 | Jacobsen et al. |
| 6,200,265 B1 | 3/2001 | Walsh et al. |
| 6,203,495 B1 | 3/2001 | Bardy |
| 6,206,914 B1 | 3/2001 | Soykan et al. |
| 6,207,451 B1 | 3/2001 | Dennis et al. |
| 6,213,942 B1 | 4/2001 | Flach et al. |
| 6,221,011 B1 | 4/2001 | Bardy |
| 6,224,566 B1 | 5/2001 | Loeb |
| 6,231,516 B1 | 5/2001 | Keilman et al. |
| 6,235,970 B1 | 5/2001 | Stice et al. |
| 6,237,398 B1 | 5/2001 | Porat et al. |
| 6,245,566 B1 | 6/2001 | Gearhart et al. |
| 6,251,125 B1 | 6/2001 | KenKnight et al. |
| 6,254,573 B1 | 7/2001 | Haim et al. |
| 6,256,233 B1 | 7/2001 | Glass |
| 6,261,230 B1 | 7/2001 | Bardy |
| 6,266,554 B1 | 7/2001 | Hsu et al. |
| 6,270,457 B1 | 8/2001 | Bardy |
| 6,272,377 B1 | 8/2001 | Sweeney et al. |
| 6,277,072 B1 | 8/2001 | Bardy |
| 6,277,078 B1 | 8/2001 | Porat et al. |
| 6,278,894 B1 | 8/2001 | Salo et al. |
| 6,280,380 B1 | 8/2001 | Bardy |
| 6,284,242 B1 | 9/2001 | Kurachi |
| 6,287,285 B1 | 9/2001 | Michal et al. |
| 6,298,267 B1 | 10/2001 | Rosborough et al. |
| 6,298,272 B1 | 10/2001 | Peterfeso et al. |
| 6,306,830 B1 | 10/2001 | Hammond et al. |
| 6,309,370 B1 | 10/2001 | Haim et al. |
| 6,312,378 B1 | 11/2001 | Bardy |
| 6,316,419 B1 | 11/2001 | Leiden et al. |
| 6,317,631 B1 | 11/2001 | Ben-Haim et al. |
| 6,330,481 B1 | 12/2001 | Van Wijk et al. |
| 6,331,160 B1 | 12/2001 | Bardy |
| 6,336,903 B1 | 1/2002 | Bardy |
| 6,358,202 B1 | 3/2002 | Arent |
| 6,358,203 B2 | 3/2002 | Bardy |
| 6,361,522 B1 | 3/2002 | Scheiner et al. |
| 6,361,780 B1 | 3/2002 | Ley et al. |
| 6,368,284 B1 | 4/2002 | Bardy |
| 6,370,424 B1 | 4/2002 | Prutchi |
| 6,385,491 B1 | 5/2002 | Lindemans et al. |
| 6,387,369 B1 | 5/2002 | Pittenger et al. |
| 6,398,728 B1 | 6/2002 | Bardy |
| 6,399,300 B1 | 6/2002 | Field |
| 6,410,236 B1 | 6/2002 | Metzger |
| 6,411,840 B1 | 6/2002 | Bardy |
| 6,411,844 B1 | 6/2002 | Steve et al. |
| 6,424,847 B1 | 7/2002 | Mastrototaro et al. |
| 6,428,802 B1 | 8/2002 | Atala |
| 6,436,672 B1 | 8/2002 | Tomlinson |
| 6,436,907 B1 | 8/2002 | Leiden et al. |
| 6,438,419 B1 | 8/2002 | Callaway et al. |
| 6,440,066 B1 | 8/2002 | Bardy |
| 6,442,413 B1 | 8/2002 | Silver |
| 6,443,949 B2 | 9/2002 | Altman |
| 6,451,594 B1 | 9/2002 | Chien et al. |
| 6,453,195 B1 | 9/2002 | Thompson |
| 6,459,917 B1 | 10/2002 | Gowda et al. |
| 6,459,929 B1 | 10/2002 | Hopper et al. |
| 6,463,335 B1 | 10/2002 | Munch et al. |
| 6,468,263 B1 | 10/2002 | Fischell et al. |
| 6,468,985 B1 | 10/2002 | Huang |
| 6,473,640 B1 | 10/2002 | Erlebacher |
| 6,475,232 B1 | 11/2002 | Babbs et al. |
| 6,478,737 B2 | 11/2002 | Bardy |
| 6,501,983 B1 | 12/2002 | Natarajan et al. |
| 6,507,756 B1 | 1/2003 | Heynen et al. |

| | | |
|---|---|---|
| 6,511,477 B2 | 1/2003 | Altman et al. |
| 6,518,245 B1 | 2/2003 | Anderson et al. |
| 6,539,256 B1 | 3/2003 | KenKnight et al. |
| 6,540,725 B1 | 4/2003 | Ponzi |
| 6,541,116 B2 | 4/2003 | Michal et al. |
| 6,569,082 B1 | 5/2003 | Chin |
| 6,574,507 B1 | 6/2003 | Bonnet |
| 6,575,931 B1 | 6/2003 | Ponzi |
| 6,592,623 B1 | 7/2003 | Bowlin et al. |
| 6,596,745 B2 | 7/2003 | Gall |
| 6,604,000 B2 | 8/2003 | Lu |
| 6,610,716 B2 | 8/2003 | Wagle et al. |
| 6,623,473 B1 | 9/2003 | Ponzi |
| 6,623,474 B1 | 9/2003 | Ponzi |
| 6,628,987 B1 | 9/2003 | Hill et al. |
| 6,653,291 B1 | 11/2003 | Badylak et al. |
| 6,656,517 B2 | 12/2003 | Michal |
| 6,660,737 B2 | 12/2003 | Almstead et al. |
| 6,666,826 B2 | 12/2003 | Salo et al. |
| 6,671,558 B1 | 12/2003 | Soykan et al. |
| 6,689,117 B2 | 2/2004 | Sweeney et al. |
| 6,690,970 B1 | 2/2004 | Taheri et al. |
| 6,695,769 B2 | 2/2004 | French et al. |
| 6,702,732 B1 | 3/2004 | Lau et al. |
| 6,702,777 B2 | 3/2004 | Haim et al. |
| 6,709,456 B2 | 3/2004 | Langberg et al. |
| 6,723,041 B2 | 4/2004 | Lau et al. |
| 6,730,016 B1 | 5/2004 | Cox et al. |
| 6,733,996 B2 | 5/2004 | Froehlich et al. |
| 6,735,471 B2 | 5/2004 | Hill et al. |
| 6,748,653 B2 | 6/2004 | Lindemans et al. |
| 6,749,556 B2 | 6/2004 | Banik |
| 6,755,779 B2 | 6/2004 | Vanden Hoek et al. |
| 6,759,236 B1 | 7/2004 | Fung et al. |
| 6,775,574 B1 | 8/2004 | Soykan et al. |
| 6,790,172 B2 | 9/2004 | Alferness et al. |
| 6,793,618 B2 | 9/2004 | Schweich et al. |
| 6,801,805 B2 | 10/2004 | Stokes et al. |
| 6,808,483 B1 | 10/2004 | Ortiz et al. |
| 6,808,488 B2 | 10/2004 | Mortier et al. |
| 6,810,286 B2 | 10/2004 | Donovan et al. |
| 6,832,112 B1 | 12/2004 | Bornzin |
| 6,855,124 B1 | 2/2005 | Gonzalez et al. |
| 6,865,420 B1 | 3/2005 | Kroll |
| 6,876,887 B2 | 4/2005 | Okuzumi et al. |
| 6,902,522 B1 | 6/2005 | Walsh et al. |
| 6,905,476 B2 | 6/2005 | Ponzi |
| 6,919,207 B2 | 7/2005 | Goodman et al. |
| 6,965,798 B2 | 11/2005 | Kim |
| 6,973,349 B2 | 12/2005 | Salo |
| 7,039,462 B2 | 5/2006 | Pastore et al. |
| 7,043,305 B2 | 5/2006 | Kenknight et al. |
| 7,072,711 B2 | 7/2006 | Girouard et al. |
| 7,294,334 B1 | 11/2007 | Michal et al. |
| 7,326,571 B2 | 2/2008 | Freyman |
| 7,627,373 B2 | 12/2009 | Girouard et al. |
| 7,764,995 B2 | 7/2010 | Steven et al. |
| 2001/0000802 A1 | 5/2001 | Soykan et al. |
| 2001/0016193 A1 | 8/2001 | Engler |
| 2001/0055590 A1 | 8/2001 | Kurachi |
| 2001/0041928 A1 | 11/2001 | Pavcnik et al. |
| 2001/0051148 A1 | 12/2001 | Tremblay |
| 2002/0001577 A1 | 1/2002 | Haverich et al. |
| 2002/0010492 A1 | 1/2002 | Donovan et al. |
| 2002/0012657 A1 | 1/2002 | Tremblay |
| 2002/0019350 A1 | 2/2002 | Levine et al. |
| 2002/0022022 A1 | 2/2002 | Shi et al. |
| 2002/0022259 A1 | 2/2002 | Lee et al. |
| 2002/0026228 A1 | 2/2002 | Schauerte |
| 2002/0031501 A1 | 3/2002 | Law |
| 2002/0031827 A1 | 3/2002 | Kanno et al. |
| 2002/0048800 A1 | 4/2002 | Gu et al. |
| 2002/0049154 A1 | 4/2002 | Grissom et al. |
| 2002/0055530 A1 | 5/2002 | Neuberger et al. |
| 2002/0065243 A1 | 5/2002 | Fung et al. |
| 2002/0072785 A1 | 6/2002 | Nelson et al. |
| 2002/0077311 A1 | 6/2002 | Leiden et al. |
| 2002/0098167 A1 | 7/2002 | Anversa et al. |
| 2002/0099026 A1 | 7/2002 | Goodman et al. |
| 2002/0107553 A1 | 8/2002 | Hill et al. |
| 2002/0110910 A1 | 8/2002 | Gwathmey et al. |
| 2002/0115208 A1 | 8/2002 | Mitchell et al. |
| 2002/0124855 A1 | 9/2002 | Chachques |
| 2002/0127210 A1 | 9/2002 | Mickle et al. |
| 2002/0133198 A1 | 9/2002 | Kramer et al. |
| 2002/0142457 A1 | 10/2002 | Umezawa et al. |
| 2002/0147172 A1 | 10/2002 | Podsakoff et al. |
| 2002/0147329 A1 | 10/2002 | Luyten et al. |
| 2002/0147479 A1 | 10/2002 | Aldrich |
| 2002/0155101 A1 | 10/2002 | Donahue et al. |
| 2002/0161410 A1 | 10/2002 | Kramer et al. |
| 2002/0172663 A1 | 11/2002 | Palasis et al. |
| 2002/0183686 A1 | 12/2002 | Darvish et al. |
| 2002/0183720 A1 | 12/2002 | Hill et al. |
| 2003/0004403 A1 | 1/2003 | Drinan et al. |
| 2003/0036773 A1 | 2/2003 | Whitehurst et al. |
| 2003/0036801 A1 | 2/2003 | Schwartz et al. |
| 2003/0040777 A1 | 2/2003 | Shemer et al. |
| 2003/0044802 A1 | 3/2003 | Sayler et al. |
| 2003/0059463 A1 | 3/2003 | Lahtinen |
| 2003/0060854 A1 | 3/2003 | Zhu |
| 2003/0060857 A1 | 3/2003 | Perrson et al. |
| 2003/0065379 A1 | 4/2003 | Babbs et al. |
| 2003/0073235 A1 | 4/2003 | Lagarias et al. |
| 2003/0082148 A1 | 5/2003 | Ludwig |
| 2003/0087264 A1 | 5/2003 | Kaplitt et al. |
| 2003/0087867 A1 | 5/2003 | Vogels et al. |
| 2003/0104568 A1 | 6/2003 | Lee |
| 2003/0105493 A1 | 6/2003 | Salo |
| 2003/0113303 A1 | 6/2003 | Schwartz |
| 2003/0125615 A1 | 7/2003 | Schwartz |
| 2003/0129750 A1 | 7/2003 | Schwartz |
| 2003/0130581 A1 | 7/2003 | Salo et al. |
| 2003/0144702 A1 | 7/2003 | Yu et al. |
| 2003/0144703 A1 | 7/2003 | Yu et al. |
| 2003/0148351 A1 | 8/2003 | Henry et al. |
| 2003/0148968 A1 | 8/2003 | Hammond et al. |
| 2003/0153952 A1 | 8/2003 | Auricchio et al. |
| 2003/0167081 A1 | 9/2003 | Zhu et al. |
| 2003/0171723 A1 | 9/2003 | Ponzi |
| 2003/0187396 A1 | 10/2003 | Ponzi |
| 2003/0187490 A1 | 10/2003 | Gliner |
| 2003/0195470 A1 | 10/2003 | Ponzi |
| 2003/0199813 A1 | 10/2003 | Struble |
| 2003/0204206 A1 | 10/2003 | Padua et al. |
| 2003/0211130 A1 | 11/2003 | Sanders et al. |
| 2003/0216476 A1 | 11/2003 | Kleemann |
| 2003/0216811 A1 | 11/2003 | Badylak |
| 2003/0216812 A1 | 11/2003 | Badylak |
| 2004/0002739 A1 | 1/2004 | Cates et al. |
| 2004/0006395 A1 | 1/2004 | Badylak |
| 2004/0018174 A1 | 1/2004 | Palasis |
| 2004/0030379 A1 | 2/2004 | Hamm et al. |
| 2004/0038400 A1 | 2/2004 | Froehlich et al. |
| 2004/0043006 A1 | 3/2004 | Badylak et al. |
| 2004/0047909 A1 | 3/2004 | Ragheb et al. |
| 2004/0048286 A1 | 3/2004 | Lee |
| 2004/0073260 A1 | 4/2004 | Brighton |
| 2004/0087019 A1 | 5/2004 | Soykan et al. |
| 2004/0088017 A1 | 5/2004 | Sharma et al. |
| 2004/0098075 A1 | 5/2004 | Lee |
| 2004/0106954 A1 | 6/2004 | Whitehurst et al. |
| 2004/0122478 A1 | 6/2004 | Stadler et al. |
| 2004/0122484 A1 | 6/2004 | Hatlestad et al. |
| 2004/0131601 A1 | 7/2004 | Epstein et al. |
| 2004/0132184 A1 | 7/2004 | Dennis et al. |
| 2004/0158289 A1 | 8/2004 | Girouard et al. |
| 2004/0158290 A1 | 8/2004 | Girouard |
| 2004/0161421 A1 | 8/2004 | Komowski et al. |
| 2004/0186546 A1 | 9/2004 | Mandrusov et al. |
| 2004/0208845 A1 | 10/2004 | Michal et al. |
| 2004/0213770 A1 | 10/2004 | Seward et al. |
| 2004/0214182 A1 | 10/2004 | Sharma et al. |
| 2004/0215251 A1 | 10/2004 | Sharma et al. |
| 2004/0215253 A1 | 10/2004 | Weinberg |
| 2004/0253209 A1 | 12/2004 | Soykan et al. |
| 2005/0002912 A1 | 1/2005 | Chachques |
| 2005/0005923 A1 | 1/2005 | Herrin |

| | | |
|---|---|---|
| 2005/0008628 A1 | 1/2005 | Feld et al. |
| 2005/0013870 A1 | 1/2005 | Freyman et al. |
| 2005/0021091 A1 | 1/2005 | Laske et al. |
| 2005/0025752 A1 | 2/2005 | Kutryk et al. |
| 2005/0025838 A1 | 2/2005 | Badylak |
| 2005/0043675 A1 | 2/2005 | Pastore et al. |
| 2005/0059153 A1 | 3/2005 | George et al. |
| 2005/0059999 A1 | 3/2005 | Mongeon et al. |
| 2005/0079202 A1 | 4/2005 | Chen et al. |
| 2005/0096701 A1 | 5/2005 | Donovan et al. |
| 2005/0112759 A1 | 5/2005 | Radisic et al. |
| 2005/0118144 A1 | 6/2005 | Zhang |
| 2005/0123526 A1 | 6/2005 | Shafer |
| 2005/0130136 A1 | 6/2005 | Lee |
| 2005/0137626 A1 | 6/2005 | Pastore et al. |
| 2005/0137631 A1 | 6/2005 | Yu et al. |
| 2005/0137671 A1 | 6/2005 | Liu et al. |
| 2005/0192637 A1 | 9/2005 | Girouard et al. |
| 2005/0209665 A1* | 9/2005 | Hunter et al. ............. 607/115 |
| 2005/0209666 A1* | 9/2005 | Hunter et al. ............. 607/115 |
| 2005/0245972 A1 | 11/2005 | Onyekaba et al. |
| 2005/0283197 A1 | 12/2005 | Daum et al. |
| 2005/0288721 A1 | 12/2005 | Girouard et al. |
| 2006/0008500 A1 | 1/2006 | Chavan et al. |
| 2006/0134071 A1 | 6/2006 | Ross et al. |
| 2006/0134079 A1 | 6/2006 | Sih et al. |
| 2006/0136027 A1 | 6/2006 | Westlund et al. |
| 2006/0136028 A1 | 6/2006 | Ross et al. |
| 2006/0282123 A1* | 12/2006 | Hunter et al. ............. 607/3 |
| 2007/0027487 A1 | 2/2007 | Mika et al. |
| 2007/0198063 A1* | 8/2007 | Hunter et al. ............. 607/3 |
| 2008/0124374 A1 | 5/2008 | Freyman |

FOREIGN PATENT DOCUMENTS

| | | |
|---|---|---|
| EP | 0347708 A1 | 12/1989 |
| EP | 0467695 A2 | 1/1992 |
| EP | 0545628 A2 | 6/1993 |
| EP | 0550343 A1 | 7/1993 |
| EP | 0550344 A1 | 7/1993 |
| EP | 0620420 A1 | 10/1994 |
| EP | 0633031 A1 | 1/1995 |
| EP | 0674916 A2 | 10/1995 |
| EP | 1050265 A2 | 11/2000 |
| EP | 1142607 A2 | 10/2001 |
| WO | WO-92/08796 A1 | 5/1992 |
| WO | WO-93/20888 A1 | 10/1993 |
| WO | WO-94/28143 A1 | 12/1994 |
| WO | WO-95/28494 A1 | 10/1995 |
| WO | WO-95/34647 A1 | 12/1995 |
| WO | WO-96/00295 A1 | 1/1996 |
| WO | WO-96/32984 A1 | 10/1996 |
| WO | WO-96/40195 A1 | 12/1996 |
| WO | WO-97/06854 A1 | 2/1997 |
| WO | WO-97/33513 A1 | 9/1997 |
| WO | WO-98/02150 A1 | 1/1998 |
| WO | WO-98/34537 A1 | 8/1998 |
| WO | WO-99/25385 A1 | 5/1999 |
| WO | WO-00/07497 A1 | 2/2000 |
| WO | WO-00/17326 A1 | 3/2000 |
| WO | WO-00/74584 A1 | 12/2000 |
| WO | WO-01/03750 A1 | 1/2001 |
| WO | WO-02/04063 A1 | 1/2002 |
| WO | WO-02/05866 A2 | 1/2002 |
| WO | WO-02/49669 A2 | 6/2002 |
| WO | WO-02/49714 A2 | 6/2002 |
| WO | WO-02/070065 A2 | 9/2002 |
| WO | WO-2004/016200 A1 | 2/2004 |
| WO | WO-2004/024206 A1 | 3/2004 |
| WO | WO-2004/030706 A2 | 4/2004 |
| WO | WO-2004/050180 A2 | 6/2004 |
| WO | WO-2004/080533 A1 | 9/2004 |
| WO | WO-2004/093969 A1 | 11/2004 |
| WO | WO-2005/084751 A2 | 9/2005 |
| WO | WO-2005/120635 A1 | 12/2005 |

OTHER PUBLICATIONS

Badylak, S., et al., "Extracellular Matrix for Myocardial Repair", *Heart Surgery Forum*, 6(2), (2003),E20-E26.

Badylak, S. F., "Small Intestinal Submucosa (SIS): A Biomaterial Conducive to Smart Tissue Remodeling", In: *Tissue Engineering: Current Perspectives*, Bell, E., Editor, Burkhauser Publishers, Cambridge, MA, (1993), 179-189.

Badylak, S. F., et al., "Small Intestinal Submucosa: A Rapidly Resorbed Bioscaffold for Augmentation Cystoplasty in a Dog Model", *Tissue Engineeering*, 4(4), (1998),379-387.

Badylak, S. F., "The Extracellular Matrix as a Scaffold for Tissue Reconstruction", *Seminars in Cell Developmental Biology*, 13(5), (Oct. 2002),377-383.

Bell, E., "Strategy for the Selection of Scaffolds for Tissue Engineering", *Tissue Engineering*, 1(2), (1995),163-179.

Bellamkonda, R., et al., "Hydrogel-based three-dimensional matrix for neural cells.", *J Biomed Mater Res.*, 29(5), (May 1995),663-71.

Boekstegers, P., et al., "Regional Myocardial Gene Transfer Using High Efficacy with Selective Pressure-Regulated Retroinfusion of Coronary Veins", *Circulation*, 100 (Suppl. 1), (Abstract #4302), Abstracts from the 72$^{nd}$ Scientific Sessions, (Nov. 1999), p. I-815.

Bouhadir, K. H., et al., "In Vitro and In Vivo Models for the Reconstruction of Intercellular Signaling", *Annals of the New York Academy of Sciences*, 842, (1998),188-194.

Brigham, K. L., et al., "Cationic Liposomes and DNA Delivery", *Journal of Liposome Research*, 3(1), (1993),31-49.

Capecchi, M. R., "High efficiency transformation by direct microinjection of DNA into cultured mammalian cells.", *Cell*, 22(2 Pt 2), (Nov. 1980),479-88.

Chonn, A., et al., "Recent Advances in Liposomal Drug-Delivery Systems", *Current Opinion in Biotechnolgy*, 6(6), (1995),698-708.

Chu, G., "SV40 DNA transfection of cells in suspension: analysis of efficiency of transcription and translation of T-antigen.", *Gene*, 13(2), (Mar. 1981),197-202.

Courtman, D. W., et al., "Development of a pericardial acellular matrix biomaterial: Biochemical and mechanical effects of cell extraction", *J Biomed Materi Res.*, 28(6), (1994),655-66.

Curiel, D. T., et al., "Adenovirus enhancement of transferrin-polylysine-mediated gene delivery", *Proc Natl Acad Sci USA.*, 88(19), (Oct. 1, 1991),8850-4.

Curtil, A. , et al., "Freeze Drying of Cardiac Valves in Preparation for Cellular Repopulation", *Cryobiology*, 34(1), (Feb. 1997),13-22.

Donahue, J. K., et al., "Focal Modification of Electrical Conduction in the Heart by Viral Gene Transfer", *Nature Medicine*, 6(12), (2000),1395-1398.

Felgner, P. L., et al., "Lipofection: A highly efficient, lipid-mediated DNA-transfection procedure", *Proc. Natl. Acad. Sci. USA*, 84, (Nov. 1987),7413-7417.

Gleeson, M. J., et al., "The use of alloplastic biomaterials in bladder substitution", *Journal of Urology*, 148, (1992),1377-1382.

Graham, F. L., "A New Technique for the Assay of Infectivity of Human Adenovirus 5 DNA", *Virology*, 52, (1973),456-467.

Hajjar, R. J., et al., "Modulation of Ventricular Function Through Gene Transfer in vivo", *Proc Natl Acad Sci USA*, 95, (1998),5251-5256.

Hajjar, R. J., et al., "Prospects for Gene Therapy for Heart Failure", *Circulation Research*, 86(6), (2000),616-621.

Hodde, J. P., et al., "Retention of Endothelial Cell Adherence to Porcine-Derived Extracellular Matrix After Disinfection and Sterilization", *Tissue Engineering*, 8(2), (Apr. 2002),225-34.

Hoshijima, M., et al., "Chronic Suppression of Heart-Failure Progression by a Pseudophosphorylated Mutant of Phospholamban via in vivo Cardiac rAAV Gene Delivery", *Nature Medicine*, 8(8), (2002),864-871.

Isner, J. M., "Myocardial Gene Therapy", *Nature*, 415(6868), (2002),234-239.

Klein, T. M., "High-Velocity Microprojectiles for Delivering Nucleic Acids into Living Cells", *Nature*, 327, (1987),70-73.

Ledley, F. D., "Non-Viral Gene Therapy: The Promise of Genes as Pharmaceutical Products", *Human Gene Therapy*, 6, (1995),1129-1144.

Lynch, C. M., et al., "Adeno-Associated Virus Vectors for Vascular Gene Delivery", *Circulation Research*, 80(4), (1997),497-505.

Mannino, R. J., "Liposome Mediated Gene Transfer.", *BioTechniques*, 6(7), (Jul.-Aug. 1988),682-90.

Meezan, E., et al., "A simple, versatile, nondisruptive method for the isolation of morphologically and chemically pure basement membranes from several tissues", *Life Sciences*, 17(11), (Dec. 1, 1974),1721-1732.

Miller, N., et al., "Targeted Vectors for Gene Therapy", *FASEB Journal*, 9(2), (Feb. 1995),190-199.

Schnepp, B., et al., "Chapter 29—Highly Purified Recombinant Adeno-Associated Virus Vectors. Preparation and Quantitation", In: Methods in Molecular Medicine, vol. 29—*Gene Therapy Protocols*, Jeffrey R. Morgan, Editor, Humana Press, Totowa, N.J.,(2002),427-443.

Schofield, J. P., et al., "Non-Viral Approaches to Gene Therapy", *British Medical Bulletin*, 51(1), (1995),56-71.

Schreier, H., "The New Frontier: Gene and Oligonucleotide Therapy", *Pharmaceutical Acta Helvetiae* 68(3), (1994),145-159.

Shigekawa, K., "Electroporation of Eukaryotes and Prokaryotes: A General Approach to the Introduction of Macromolecules into Cells", *BioTechniques*, 6, (1988),742-751.

"U.S. Appl. No. 10/722,115, Final Office Action mailed Dec. 11, 2009", 13 pgs.

"U.S. Appl. No. 11/017,237, Final Office Action mailed Jan. 25, 2010", 14 pgs.

"U.S. Appl. No. 11/017,432, Response filed Dec. 21, 2009 to Non Final Office Action mailed Aug. 20, 2009", 19 pgs.

"U.S. Appl. No. 11/017,237, Response filed Jan. 28, 2008 to Restriction Requirement mailed Dec. 28, 2007", 7 pgs.

"U.S. Appl. No. 11/017,237, Response filed Jul. 10, 2008 to Non Final Office Action mailed Apr. 10, 2008", 8 pgs.

"U.S. Appl. No. 11/017,237, Final Office Action mailed Nov. 13, 2008", 9 pgs.

"U.S. Appl. No. 11/017,237, Non Final Office Action mailed May 29, 2009", 11 pgs.

"U.S. Appl. No. 11/017,237, Non-Final Office Action mailed Apr. 10, 2008", 6 pgs.

"U.S. Appl. No. 11/017,237, Response filed Sep. 29, 2009 to Non Final Office Action mailed May 29, 2009", 15 pgs.

"U.S. Appl. No. 11/017,237, Response filed Mar. 10, 2009 to Final Office Action mailed Nov. 13, 2008", 9 pgs.

"U.S. Appl. No. 11/017,237, Restriction Requirement mailed Dec. 28, 2007", 7 pgs.

"U.S. Appl. No. 11/017,432, Non-Final Office Action mailed Aug. 20, 2009", 19 pgs.

"U.S. Appl. No. 11/017,432, Advisory Action mailed Aug. 16, 2007", 8 pgs.

"U.S. Appl. No. 11/017,432, Final Office Action mailed Apr. 5, 2007", 30 pgs.

"U.S. Appl. No. 11/017,432, Final Office Action mailed on Nov. 3, 2008", 24 pgs.

"U.S. Appl. No. 11/017,432, Non Final Office Action mailed Sep. 13, 2006", 29 pgs.

"U.S. Appl. No. 11/017,432, Non-Final Office Action mailed Nov. 5, 2007", 25 pgs.

"U.S. Appl. No. 11/017,432, Response filed Jan. 16, 2007 to Non Final Office Action mailed Sep. 13, 2006", 15 pgs.

"U.S. Appl. No. 11/017,432, Response filed Mar. 5, 2008 to Non-Final Office Action mailed Nov. 5, 2007", 13 pgs.

"U.S. Appl. No. 11/017,432, Response filed Jul. 7, 2008 to Restriction Requirement mailed Jun. 6, 2008", 12 pgs.

"U.S. Appl. No. 11/017,432, Response filed Jul. 28, 2006 to Restriction Requirement mailed Jun. 28, 2006", 8 pgs.

"U.S. Appl. No. 11/017,432, Response filed Aug. 3, 2007 to Final Office Action mailed Apr. 5, 2007", 16 pgs.

"U.S. Appl. No. 11/017,432, Response filed Feb. 19, 2009 to Final Office Action mailed Nov. 3, 2008", 23 pgs.

"U.S. Appl. No. 11/017,432, Restriction Requirement mailed Jun. 6, 2008", 6 pgs.

"U.S. Appl. No. 11/017,432, Restriction Requirement mailed Jun. 28, 2006", 9 pgs.

"U.S. Appl. No. 11/017,627, Advisory Action mailed May 21, 2007", 3 pgs.

"U.S. Appl. No. 11/017,627, Advisory Action mailed Apr. 20, 2007", 2 pgs.

"U.S. Appl. No. 11/017,627, Advisory Action mailed Aug. 11, 2008", 3 pgs.

"U.S. Appl. No. 11/017,627, Final Office Action mailed Feb. 13, 2007", 15 pgs.

"U.S. Appl. No. 11/017,627, Final Office Action mailed May 15, 2008", 11 pgs.

"U.S. Appl. No. 11/017,627, Non Final Office Action mailed Sep. 22, 2006", 17 pgs.

"U.S. Appl. No. 11/017,627, Non-Final Office Action mailed Oct. 9, 2007", 12 pgs.

"U.S. Appl. No. 11/017,627, Response filed Jan. 9, 2008 to Non-Final Office Action mailed Oct. 9, 2007", 13 pgs.

"U.S. Appl. No. 11/017,627, Response filed Apr. 12, 2007 to Final Office Action mailed Feb. 13, 2007", 16 pgs.

"U.S. Appl. No. 11/017,627, Response filed Jul. 3, 2007 to Final Office Action mailed Feb. 13, 2007 and Advisory Action mailed May 21, 2007", 17 pgs.

"U.S. Appl. No. 11/017,627, Response filed Jul. 15, 2008 to Final Office Action mailed May 15, 2008", 14 pgs.

"U.S. Appl. No. 11/017,627, Response filed Aug. 13, 2009 to Non Final Office Action mailed Dec. 2, 2008", 14 pgs.

"U.S. Appl. No. 11/017,627, Response filed Sep. 15, 2008 to Advisory Action mailed Aug. 11, 2008 and Final Office Action mailed May 15, 2008", 14 pgs.

"U.S. Appl. No. 11/017,627, Response filed Dec. 22, 2006 to Non Final Office Action mailed Sep. 22, 2006", 19 pgs.

"COOK SIS Technology: Scientific Information: Clinical References", [online]. [retrieved Apr. 7, 2004]. Retrieved from the Internet: <URL: http://www.cooksis.com/sci/ref1.html>, (2004), 4 pgs.

"COOK SIS Technology: Scientific Information: Safety", [online]. [retrieved Apr. 7, 2004]. Retrieved from the Internet: <URL: http://www.cooksis.com/sci/tech3.html>, (2004), 2 pgs.

"COOK SIS Technology: Scientification Information: Tissue Repair: Challenges & Complications", [online]. [retrieved Apr. 7, 2004]. Retrieved from the Internet: <http://www.cooksis.com/sci/tech.html>, (2004), 2 pgs.

"European Applicaion Serial No. 05757159.8, Office Action received Oct. 29, 2009", 3 pgs.

Akiyama-Uchida, Y., et al., "Norepinephrine enhances fibrosis mediated by TGF-β in cardiac fibroblasts", *Hypertension*, 40(2), (Aug. 2002), 148-54.

Allman, A. J., et al., "Xenogeneic extracellular matrix grafts elicit a TH2-restricted immune response", *Transplantation*, 71(11), (Jun. 15, 2001), 1631-1640.

Arnaud, C., et al., "iNOS is a mediator of the heat stress-induced preconditioning against myocardial infarction in vivo in the rat", *Cardiovascular Research* 58, 2003, 118-125.

Askari, A., et al., "Targeted Gene Therapy for the Treatment of Cardiac Dysfunction", *Seminars in Thoracic and Cardiovascular Surgery*, 14(2), (Apr. 2002), 167-177.

Aukrust, P., et al., "Immunomodulating Therapy: New Treatment Modality in Congestive Heart Failure", *Congest Heart Fail.*, 9(2), (Mar.-Apr. 2003), 64-69.

Badylak, S. F., et al., "Marrow-Derived Cells Populate Scaffolds Composed of Xenogeneic Extracellular Matrix", *Experimental Hematology*, 29(11), (Nov. 2001), 1310-1318.

Badylak, S. F., et al., "Resorbable bioscaffold for esophageal repair in a dog model", *Journal of Pediatric Surgery*, 35(7), (Jul. 2000), 1097-1103.

Baker, A. H., "Development and Use of Gene Transfer for Treatment of Cardiovascular Disease", *J Card Surg*, 17, (2002), 543-548.

Barbone, A., "Comparison of right and left ventricular responses to left ventricular assist device support in patients with severe heart failure: a primary role of mechanical unloading underlying reverse remodeling", *Circulation*, 104(6), (Aug. 7, 2001), 670-675.

Bigatel, D. A., et al., "The matrix metalloproteinase inhibitor BB-94 limits expansion of experimental abdominal aortic aneurysms", *J Vasc Surg*, 29(1), (1999), 130-138.

Boheler, K. R, et al., "Differentiation of Pluripotent Embryonic Stem Cells into Cardiomyocytes", *Circulation Research*, 91(3), (Aug. 9, 2002), 189-201.

Bovenberg, W. A., et al., "Expression of recombinant human insulin-like growth factor I in mammalian cells", *Mol Cell Endocrinol.*, 74(1), (Nov. 12, 1990), 45-59.

Bralet, J, et al., "Vasopeptidase inhibitors: an emerging class of cardiovascular drugs", *Trends Pharmacol Sci.*, 22(3), (Mar. 2001), 106-109.

Brugada, R., et al., "Genetics of Cardiovascular Disease with Emphasis on Atrial Fibrillation", *Journal of Interventional Cardiac Electrophysiology*, 3, (1999), 7-13.

Brundel, B. J. M., et al., "Alterations in Potassium Channel Gene Expression in Atria of Patients With Persistant and Paroxysmal Atrial Fibrillation: Differential Regulation of Protein and mRNA Levels for $K^+$ Channels", *Journal of the American College of Cardiology*, 37(3), (2001), 926-932.

Brunner, F., "Attenuation of myocardial ischemia/reperfusion injury in mice with myocyte-specific overexpression of endothelial nitric oxide synthase", *Cardiovasular Research*, 57, (2003), 55-62.

Buchwald, A B, et al., "Decoy Oligodeoxynucleotide Against Activator Protein-1 Reduces Neointimal Proliferation After Coronary Angioplasty in Hypercholesterolemic Minipigs", *Journal of the American College of Cardiology*, 39 (4), (Feb. 20, 2002), 732-738.

Bursac, N., et al., "Cardiac Muscle Tissue Engineering: toward Electrophysiological Studies", *Am. J. Phvsio.*; 277, Heart Cric. Physiol.; 46, (1999), H433-H444.

Burton, D. Y., et al., "The Incorporation of an Ion Channel Gene Mutation Associated with the Long QT Syndrome (Q9E-hMiRPI) in a Plasmid Vector for Site-Specific Arrhythmia Gene Therapy: In Vitro and In Vivo Feasibility Studies", *Human Gene Therapy*, 14, (2003), 907-922.

Cate, F. U, et al., "Endocardial and epicardial steroid lead pacing in the neonatal and paediatric age group", *Heart*, 88(4), (2002), 392-396.

Chachques, J. C., et al., "Electrostimulation Enhanced Fatigue Resistant Myosin Expression in Cellular Cardiomyoplasty", *Circulation*, 104(Suppl. 2), (Abstract No. 2626), *Abstracts from Scientific Sessions 2001*, Anaheim, CA, Nov. 11-14, 2001, (2001), pp. II-555-II-556.

Cheng, C.-F., et al., "Genetic Modifiers of Cardiac Arrhythmias", *Trends in Molecular Medicine*, 9(2), (2003), 59-66.

Cleland, J. G. F., et al., "Update of Clinical Trials from the American College of Cardiology 2003. Ephesus, Sportif-III, Ascot, Companion, UK-PACE and T-wave Alternans", *The European Journal of Heart Failure*, 5, 2003, 391-398.

Cohen, M. I., et al., "Permanent epicardial pacing in pediatric patients: seventeen years of experience and 1200 outpatient visits.", *Circulation*, 103 (21), (2001), 2585-2590.

Colonna, P., et al., "Myocardial infarction and left ventricular remodeling: results of the CEDIM trial. Carnitine Ecocardiografia Digitalizzata Infarto Mio", *Am Heart J.*, 139(2 Pt 3), (Feb. 2000), S124-30.

Colucci, W. S., "Molecular and Cellular Mechanisms of Myocardial Failure", *Am J Cardiol* 80(11A), (1997), 15L-25L.

Condorelli, G, et al., "Cardiomyocytes Induce Endothelial Cells to Trans-Differentiate into Cardiac Muscle: Implications for Myocardium Regeneration", *PNAS*, 98(19), (Sep. 11, 2001), 10733-10738.

Conley, B. J, et al., "Derivation, propagation and differentiation of human embryonic stem cells", *The International Journal of Biochemistry & Cell Biology*, 36, (2004), 555-567.

Cserjesi, P., et al., "Myogenin Induces the Myocyte-Specific Enhancer Binding Factor MEF-2 Independently of Other Muscle-Specific Gene Products", *Molecular and Cellular Biology*, 11(10), (1991), 4854-4862.

Daum, D. R., "Systems and Methods for Hypotension", U.S. Appl. No. 11/141,260, filed May 31, 2005, 51 pgs.

De Silva, R., et al., "Delivery and tracking of therapeutic cell preparations for clinical cardiovascular applications", *Cytotherapy*, 6(6), (2004), 12 pgs.

Del Monte, F., et al., "Targeting Calcium Cycling Proteins in Heart Failure Through Gene Transfer", *The Journal of Physiology*, 546(1), (2002), 49-61.

Depre, Christophe, et al., "Metabolic Aspects of Programmed Cell Survival and Cell Death in The Heart", *Cardiovascular Research*, 45(3), (Feb. 2000), 538-548.

Dhawan, J., et al., "Tetracycline-Regulated Gene Expression Following Direct Gene Transfer into Mouse Skeletal Muscle", *Somatic Cell and Molecular Genetics*, 21(4), (1995), 233-240.

Dobrev, D., et al., "Molecular Basis of Downregulation of G-Protein-Coupled Inward Rectifying $K^+$ Current ($I_{K,A,Ch}$) in Chronic Human Atrial Fibrillation", *Circulation*, 104, (2001), 2551-2557.

Eck, S., et al., "Chapter 5—Gene-Based Therapy", *Goodman & Gilman's The Pharmacological Basis of Therapeutics, Section 1, General Principles*, New York; McGraw-Hill, (2001), 77-101.

Eckardt, L., et al., "Load-induced changes in repolarization: evidence from experimental and clinical data", *Basic Res Cardiol*, 96(4), (2001), 369-380.

Ferdinandy, P., et al., "Nitric oxide, superoxide, and peroxynitrite in myocardial ischaemia-reperfusion injury and preconditioning", *British Journal of Pharmacology*, 138(4), (2003), 532-543.

Flögel, U., "Myoglobin: A scanvenger of bioactive NO", *Proc. Natl. Acad. Sci. USA*, 98(2), (Jan. 16, 2001), 735-740.

Freedman, S. B., et al., "Therapeutic Angiogenesis for Ischemic Cardiovascular Disease", *J. Mol Cell Cardiol.*, 33(3), (Mar. 2001), 379-393.

Gabouev, A. I., et al., "In Vitro Construction of Urinary Bladder Wall Using Porcine Primary Cells Reseeded on Acellularized Bladder Matrix and Small Intestinal Submucosa", *The International Journal of Artifical Organs*, 26(10), (Oct. 2003), 935-942.

Gage, H. F., "Cell Therapy", *Nature, 392, Supp.*, (Apr. 28, 1998), 18-24.

Gautam, A., et al., "Delivery Systems for Pulmonary Gene Therapy", *Am. J. Respir. Med.*, 1(1), (2002), 35-46.

Gewaltig, M. T, "Vasoprotection by nitric oxide: mechanisms and therapeutic potential", *Cardiovascular Research*, 55, (2002), 250-260.

Girouard, S. D., et al., "Method and Apparatus for Device Controlled Gene Expression", U.S. Appl. No. 10/788,906, filed Feb. 27, 2004, 80 pgs.

Girouard, S. D., "Method and apparatus to modulate cellular regeneration post myocardial infarct", U.S. Appl. No. 10/862,716, filed Jun. 7, 2004, 71 pgs.

Gould, P. A., et al., "Review of the Current Management Opinion of Atrial Fibrillation", *Expert Opinion on Pharmacotherapy*, 4(11), (2003), 1889-1899.

Graham, R. M., et al., "Gene and Cell Therapy for Heart Disease", *IUBMB Life*, 54, (2002), 59-66.

Hada, Y., et al., "Pulsus alternans determined by biventricular simultaneous systolic time intervals", *Circulation*, 65(3), (Mar. 1982), 617-26.

Hafizi, S., et al., "Inhibition of human cardiac fibroblast mitogenesis by blockade of mitogen-activated protein kinase and phosphatidylinositol 3-kinase.", *Cir Exp Pharma Physiol*, 26)7), (Jul. 1999), 511-3.

Hakuno, D., et al., "Bone Marrow-Derived Regenerated Cardiomyocytes (CMG Cells) Express Functional Adrenergic and Muscarinic Receptors", *Circulation*, 105, (Jan. 22, 2002), 380-386.

Hamawy, A. H., et al., "Cardiac Angiogenesis and Gene Therapy: A Strategy for Myocardial Revascularization", *Current Opinion in Cardiology*, 14, (1999), 515-522.

Hammond, H. K., et al., "Regional myocardial downregulation of the inhibitory guanosine triphosphate-binding protein ($Gia_2$) and β-adrenergic receptors in a porcine model of chronic episodic myocardial ischemia", *J Clin Res*, 92(6), (1993), 2644-52.

Harjai, K. J., et al., "Therapeutic Angiogenesis: a Fantastic New Adventure", *Journal of Interventional Cardiology*, 15(3), (2002), 223-229.

Heerdt, P. M., "Chronic Unloading By Left Ventricular Assist Device Reverses Contractile Dysfunction and Alters Gene Expression in End-Stage Heart Failure", *Circulation*, 102(22), (Nov. 28, 2000), 2713-2719.

Higashi, T., et al., "Pharmacological characterization of endothelin-induced rat pulmonary arterial dilatation", *Br J Pharmacol*, 121(4), (1997), 782-786.

Hong, Y. S., et al., "Localized Immunosuppression in the Cardia Allograft Induced by a New Lipsome-Mediated IL-10 Gene Therapy", *J. Heart Lung Transplant*, 21, (2002), 1188-1200.

Hsia, P. W., et al., "Absolute Depolarization Vector Characteristics Associated with Successful Defibrillation: Evidence of a Vulnerable Period During Ventricular Fibrillation", (Abstract No. 2933), *Circulation*, 82 (4), Supplement III, Abstracts, Oct. 1990), pp. III-738.

Hsia, P. W., et al., "Genesis of sigmoidal dose-response curve during defibrillation by random shock: a theoretical model based on experimental evidence for a vulnerable window during ventricular fibrillation.", *Pacing Clin Electrophysiol.*, 13(10), (Oct. 1990), 1326-42.

Hsia, P. W., et al., "Improved Nonthoractomy Defibrillation Based on Ventricular Fibrillation Waveform Characteristics", (Abstract No. 29), *PACE, 18—NASPE Abstracts*, (Apr. 1995), p. 803.

Hsu, W., et al., "Effect of Shock Timing on Defibrillation Success", *Pacing Clin Electrophysiol.*, 20(1 Pt 2), (Jan. 1997), 153-157.

Huq, F., et al., "Session 5: Cellular and Subcellular Basis of Remodeling—Modulating Signalling Pathways in Hypertrophy and Heart Failure by Gene Transfer", *Journal of Cardiac Failure*, 8(6)(Suppl.), (2002), S389-S400.

Ingber, D. E., "Mechanical signaling and the cellular response to extracellular matrix in angiogenesis and cardiovascular physiology", *Circulation Research*, 91(10), (Nov. 15, 2002), 877-887.

Jackson, K. A., et al., "Regeneration of Ischemic Cardiac Muscle and Vascular Endothelium By Adult Stem Cells", *The Journal of Clinical Investigation*, 107(11), (Jun. 2001), 1395-1402.

Jain, M., "Cell therapy attenuates deleterious ventricular remodeling and improves cardiac performance after myocardial infarction", *Circulation*, 103(14), (Apr. 10, 2001), 1920-1927.

Jayakumar, J., et al., "Gene Therapy for Myocardial Prevention—Transfection of Donor Hearts With Heat Shock Protein 70 Gene Protects Cardiac Function Against Ischemia-Reperfusion Therapy", Circulation, 102 (Suppl. III), (2000), III-302-III-306.

Johnson, J. E., et al. "Muscle Creatine Kinase Sequence Elements Regulating Skeletal and Cardiac Muscle Expression in Transgenic Mice", *Molecular and Cellular Biology*, 9(8), (1989), 3393-3399.

Jones, D. L., et al., "Ventricular Fibrillation: The Importance of Being Coarse?", *Journal of Electrocardiology*, 17(4), (1984), 393-399.

Jugdutt, B. I., "Remodeling of Myocardium and Potential Targets in the Collagen Degradation and Synthesis Pathways", *Current Drug Targets Cardiovasular & Haematological Disorders*, 3, (2003), 1-30.

Kaye, D., et al., "Role of Tansiently altered sarcolemmal membrane permeability and basic fribroblast growth factor release . . .", *J.Clin. Invest.* vol. 97, (1996), 281-291.

Kehat, I., et al., "Human Embryonic Stem Cells Can Differentiate Into Myoctyes With Structural and Functional Properties of Cardiomyocytes", *The Journal of Clinical Investigation*, 108(3), (Aug. 2001), 407-414.

Kiba, A., et al., "VEGFR-2-specific ligand VEGF-E induces non-edematous hyper-vascularization in mice.", *Biochem Biophys Res Commun.*, 301(2), (Feb. 7, 2003), 371-7.

Koch, W. J., et al., "Gene transfer of β-adrenergic signaling components for heart failure", *Journal of Cardiac Failure* ,8 (6 Suppl), (2002), S526-S531.

Kocher, A. A., et al., "Neovascularization of Ischemic Myocardium by Human Bone-Marrow-Derived Angioblasts Prevents Cardiomyocyte Apoptosis, Reduces Remodeling and Improves Cardiac Function", *Nature Medicine* , 7(4) , (Apr. 2001), 430-436.

Kodama, I., et al., "Cellular electropharmacology of amiodarone.", *Cardiovas Res*, 35(1), (1997), 13-29.

Kofidis, T., et al., "In vitro engineering of heart muscle: Artificial myocardial tissue", *The Journal of Thoracic and Cardiovascular Surgery*, 124 (1), (2002), 63-69.

Komuro, I., et al., "Control of Cardiac Gene Expression by Mechanical Stress", *Annu Rev Physiol.*,. (1993), pp. 55-75.

Konta, T., et al., "Significance of Discordant ST Alternans in Ventricular Fibrillation", *Circulation*, 82(6), (Dec. 1990), 2185-2189.

Kozarsky, K. F., "Gene Therapy for Cardiovascular Disease", *Current Opinion in Pharmacology*, 1, (2001), 197-202.

Krum, H., "New and Emerging Pharmacological Strategies in the Management of Chronic Heart Failure", *Current Opinion in Pharmacology*, 1(2), (Apr. 2001), 126-33.

Kuelz, K. W., et al., "Integration of absolute ventricular fibrillation voltage correlates with successful defibrillation", *IEEE Transactions on Biomedical Engineering*, 41(8), (Aug. 1994), 782-791.

Laham, R. J., et al., "Gene Transfer to Induce Angiogenesis in Myocardial and Limb Ischaemia", *Expert Opin Biol Ther.*, 1(6),., (2001), pp. 985-994.

Lee, L. Y., et al., "Exogenous Control of Cardiac Gene Therapy: Evidence of Regulated Myocardial Transgene Expression After Adenovirus and Adeno-Associated Virus Transfer of Expression Cassettes Containing Corticosteroid Response Element Promoters", *The Journal of Thoracic and Cardiovascular Surgery*, 118, (1999), 26-35.

Lee, Y. C, et al., "Pulsus alternans in patients with congestive cardiomyopathy", *Circulation*, 65(7), (Jun. 1982), 1533-4.

Lehman, J., et al., "Gene regulatory mechanisms governing energy metabolism during cardiac hypertrophic growth", *Heart Fail Rev.*, (Apr. 2000), 175-85.

Levin, L., "Researchers present findings at European cardiology conference", *Advisory Board Daily Briefing, 8. Clinical Outlook*, (Sep. 2002), 8 pages [see pp. 5,6].

Li, Q., "Gene Therapy With Inducible Nitric Oxide Synthase Protects Against Myocardial Infarction via a Cyclooxygenase-2-Dependent Mechanism", *Circulation Research*, 92, (2003), 741-748.

Lijnen, P. J., et al., "Induction of Cardiac Fibrosis by Transforming Growth Factor-$\beta_1$ ", *Molecular Genetics and Metabolism*, 71, (2000), 418-435.

Lin, H., et al., "Regulating Genes with Electromagnetic Response Elements", *Journal of Cellular Biochemistry*, 81, (2001), 143-148.

Lin, H., et al., "Specific Region of the c-*myc* Promoter is Responsive to Electric and Magnetic Fields", *Journal of Cellular Biochemistry*, 54, (1994), 281-288.

Lodie, T. A, et al., "Systematic Analysis of Reportedly Distinct Populations of Multipotent Bone Marrow-Derived Stem Cells Reveals a Lack of Distinction", *Tissue Engineering*, 8(5), (2002), 739-751.

Lopaschuk, G., "Metabolic abnormalities in the diabetic heart", *Heart Fail Rev.*, 7(2), (Apr. 2002), 149-59.

Losordo, D. W., et al., "Gene Therapy for Myocardial Angiogenesis", *Am Heart J.*, vol. 138, (1999), S132-S141.

Lovett, E. G, "Technique for Discriminating Between Coordinated and Uncoordinated Cardiac Rhythms", U.S. Appl. No. 10/435,487, filed May 9, 2003, 36 pgs.

Luepker, R. V., et al., "Transthoracic Electrical Impedance: Quantitative Evaluation of a Non-Invasive Measure of Thoracic Fluid Volume", *American Heart Journal*, 85(1), (Jan. 1973), 83-93.

Luttun, A., et al., "The Role of Proteinases in Angiogenesis, Heart Development, Restenosis, Atherosclerosis, Myocardial Ischemia, and Stroke: Insights from Genetic Studies", *Current Atherosclerosis Reports*, 2, (2000), 407-416.

MacGowan, G. A., et al., "New molecular insights into heart failure and cardiomyopathy: potential strategies and therapies", *Ir J Med Sci.*, 171(2), (Apr.-Jun. 2002), 99-104.

MacKenna, D., et al., "Role of mechanical factors in modulating cardia fibroblast function and extracellular matrix synthesis", *Cardiovascular Research*, 46, (2000), 257-263.

MacNeill, B. D., et al., "Targeting Signaling Pathways in Heart Failure by Gene Transfer", *Current Atherosclerosis Reports*, 5, (2003), 178-185.

Mader, S., "A steroid-inducible promoter for the controlled overexpression of cloned genes in eukaryotic cells", *Proc Natl Acad Sci USA*, 90(12), (1993), 5603-7.

Mai, J., et al., "Enhanced Rate Response Algorithm for Orthostatic Compensation Pacing", (Abstract No. 678), *Pacing Clin Electrophysiol*, 23, Naspe Abstracts, (Apr. 2000), p. 722.

Mann, B. K, et al., "Tissue engineering in the cardiovascular system: progress toward a tissue engineered heart", *The Anatomical Record* , 263 (4), (Aug. 1, 2001), 367-371.

Marban, E., et al., "Gene Therapy for Cardiac Arrhythmias", *Cold Spring Harbor Symposia on Quantitative Biology, vol. LXVII—The Cardiovasular System*, Published by Cold Spring Harbor Laboratory Press, (2002), 527-531.

Mbai, M., et al., "Genetic Basis for the Origin of Cardiac Arrhythmias: Implications for Therapy", *Current Cardiology Reports*, 4, (2002), 411-417.

McCluskie, M. J., et al., "Route and Method of Delivery of DNA Vaccine Influence Immune Responses in Mice and Non-Human Primates", *Molecular Medicine*, 5(5), (1999), 287-300.

McPherson, T. B., et al., "Galα(1,3)Gal epitope in porcine small intestinal submucosa", *Tissue Engineering*, 6(3), (Jun. 2000), 133-139.

Menasché, P., "Cell Theraph of Heart Failure", *CR Biologies*, vol. 325., (2002), pp. 731-738.

Michal, E. T., et al., "Methods and Compositions to Treat Myocardiac Conditions", U.S. Appl. No. 10/802,955 filed Mar. 16, 2004, 113 pgs.

Miller, L. W., et al., "Limitations of Current Medical Therapies for the Treatment of Heart Failure", *Reviews in Cardiovascular Medicine*, 4(Suppl. 2), (2003), S21-S29.

Min, M., "Electrical Impedance and Cardiac Monitoring-Technology, Potential and Applications", *International Journal of Bioelectromagnetism*, 5(1), (2003), 53-56.

Miyagawa, S., et al., "Myocardial Regeneration Therapy for Heart Failure: Hepatocyte Growth Factor Enhances The Effect of Cellular Cardiomyoplasty", *Ciruclation*, 105(21), (May 28, 2002), 2556-2561.

Mower, M. M., et al., "Synchronization of Low-Energy Pulses to Rapid Deflection Signals as a Possible Mechanism of Subthreshold Ventricular Defibrillation", (Abstract No. 298), *Abstracts of the 55th Scientific Sessions*, , (1982), p. II-75.

Muscat, G. E. O., et al., "Multiple 5'—Flanking Regions of the Human α-Skeletal Actin Gene Synergistically Modulate Muscle-Specific Expression", *Molecular and Cellular Biology*, 7(11), (1987), 4089-4099.

Nemer, G., et al., "Regulation of Heart Development and Function Through Combinatorial Interactions of Transcription Factors", *The Finnish Medical Society Duodecim, Ann Med*, vol. 33,, (2001), pp. 604-610.

Nuss, H. B., et al., "Reversal of Potassium Channel Deficiency in Cells from Failing Hearts by Adenoviral Gene Transfer: A Prototype for Gene Therapy for Disorders of Cardiac Excitability and Contractility", *Gene Therapy*, 3(10), (1996), 900-912.

Odorico, S. J., et al., "Multilineage differentiation from human embryonic stem cell lines", *Stem Cells*, 19(3), (2001), 193-204.

Orlic, D., "Bone Marrow Cells Regenerate Infarcted Myocardium", *Nature*, 410(6829), (Apr. 5, 2001), 701-705.

Ostadal, P., et al., "The effect of early treatment by cerivastatin on the serum level of C-reactive protein, interleukin-6, and interleukin-8 in patients with unstable angina and non-Q-wave myocardial infarction", *Molecular and Cellular Biochemistry*, 246, (2003), 45-50.

Palermo, J., "Transgenic remodeling of the contractile apparatus in the mammalian heart", *Circ Res*, 78(3), (1996), 504-9.

Paolocci, N., et al., "Positive inotropic and lusitropic effects of HNO/NO—in failing hearts: Independence from β-adrenergic signaling", *Proc. Natl. Acad. Sci. USA*, 100(9), (Apr. 29, 2003), 5537-5542.

Paolocci, N., "Positive inotropic and lusitropic effects of HNO/NO—in failing hearts: independance from β-adrenergic signaling", *Proc. Natl Acad.Sci. USA*, 100(9), (Apr. 29, 2003), 4978-4980.

Parikh, S., et al., "Endothelial Cell Delivery for Cardiovascular Therapy", *Advanced Drug Delivery Reviews*, 42, (2000), 139-161.

Pastore, J. M, et al., "Method and Apparatus for Device Controlled Gene Expression for Cardiac Protection", U.S. Appl. No. 11/220,397, filed Sep. 6, 2005, 68 pgs.

Pastore, J. M., "Method and Apparatus for Modulating Cellular Metabolism During Post-Ischemia or Heart Failure", U.S. Appl. No. 10/645,823, filed Aug. 21, 2003, 46 pgs.

Pasumarthi, K. BS, et al., "Cardiomyocyte Cell Cycle Regulation", *Circ Res.*, 90(10), (2002), 1044-1054.

Patberg, K. W., et al., "Cardiac Memory Is Associated With Decreased Levels of the Transcriptional Factor CREB Modulated by Angiotensin II and Calcium", *Circulation Research*, vol. 93, (2003), 472-478.

Pfeifer, A., et al., "Gene Therapy: Promises and Problems", *Ann. Rev. of Genomics and Hum. Genet.*, 2, (2001), 177-211.

Pimentel, Rhea C, et al., "Autocrine Regulation of Myocyte Cx43 Expression by VEGF", *Circ Res.*, 90:, (2002), pp. 671-677.

Pouleur, H., et al., "Changes in plasma renin activity and haemodynamics during vasodilator therapy in conscious dogs with myocardial infarction or chronic volume overload.", *Eur J Clin Investig*, 13(4), (1983), 331-8.

Pouzet, B. et al., "Intramyocardial Transplantation of Autologous Myoblasts: Can Tissue Processing Be Optimized?", *Circulation*, 102(19 Suppl 3), (2000), pp. III-210-III-215.

Pratt, A. B., et al., "Synthetic Extracellular Matrices for in situ Tissue Engineering", *Biotechnology and Bioengineering*, 86(1), (2004), 27-36.

Prinzen, F. W, et al., "Mapping of Regional Myocardial Strain and Work During Ventricular Pacing: Experimental Study Using Magnetic Resonance Imaging Tagging", *Journal of American College of Cardiology*, vol. 33 No. 6,, (1999), pp. 1735-1742.

Radisic, M, et al., "Functional assembly of engineered myocardium by electrical stimulation of cardiac myocytes cultured on scaffolds", *Proc Natl Acad Sci U S A.*, 101(52), (Dec. 28, 2004), 18129-18134.

Recer, P., "Researchers find first heart attack gene", *AP Science News, Science*: www.science.org, (2003), 1 pg.

Reinecke, H., et al., "Survival, integration, and differentiation of cardiomyocyte grafts: a study in normal and injured rat hearts", *Circulation*, 100(2), (1999), 193-202.

Rideout III, W. M, et al., "Nuclear Cloning and Epigenetic Reprogramming of the Genome", *Science*, 293, www.sciencemag.org, (Aug. 10, 2001), 1093-1098.

Rinsch, C., et al., "Delivery of FGF-2 but not VEGF by encapsulated genetically engineered myoblasts improves survival and vascularization in a model of acute skin flap ischemia", *Gene Therapy*, 8, (2001), 523-533.

Rizos, I, "Three-year survival of patients with heart failure caused by dilated cardiomyopathy and L-carnitine administration", *Am Heart J.*, 139(2 Pt 3), (Feb. 2000), S120-S123.

Robbins, J., "Remodeling the Cardiac Sarcomere Using Transgenesis", *Annu Rev Physiol.*, vol. 62,, (2000), 261-287.

Roberts, R., et al., "Genetic Aspects of Arrhythmias", *American Journal of Medical Genetics (Semin. Med. Genet.)*, 97, (2000), 310-318.

Rosborough, J. P, et al., "Electrical Therapy for Pulseless Electrical Activity", (Abstract Only), *NASPE*, 23(4), *Part II*, (Apr. 2000), p. 591.

Ross, J., "Epicardial Patch Including Isolated Extracellular Matrix With Pacing Electrodes", U.S. Appl. No. 11/017,627, filed Dec. 20, 2004, 87 pgs.

Ross, J., et al., "Use of Extracellular Matrix and Electrical Therapy", U.S. Appl. No. 11/017 237 filed Dec. 20 2004, 89 pgs.

Roth, D. A., et al., "Downregulation of cardiac guanosine in 5'-triphosphate-binding proteins in right atrium and left ventricle in pacing-induced congestive heart failure", *J Clin Invest.*,.91(3), (Mar. 1993), 939-949.

Rubenstein, D. S, et al., "Premature Beats Elicit a Phase Reversal of Mechanoelectrical Alternans in Cat Ventricular Myocytes", *Circulation*, vol. 91, No. 1, Jan. 1995, American Heart Association, (Jan. 1, 1995), 201-214.

Rubenstrunk, A., et al., "Transcriptional Activation of the Metallothionein I Gene by Electric Pulses in vivo: Basis for the Development of a New Gene Switch System", *The Journal of Gene Medicine*, 5, (2003), 773-783.

Rutanen, J., et al., "Progress and Prospects—Post-Intervention Vessel Remodeling", *Gene Therapy*, 9, (2002), 1487-1491.

Sabbah, H, et al., "Partial fatty acid oxidation inhibitors: a potentially new class of drugs for heart failure", *Eur J Heart Fail.*, 4(1), (Jan. 2002), 3-6.

Salloum, F., "Sildenafil Induces Delayed Preconditioning Through Inducible Nitric Oxide Synthase-Dependent Pathway in Mouse Heart", *Circulation Research*, 92, (2003), 595-597.

Sam, F., et al., "Role of Endothelin-1 in Myocardial Failure", *Proceedings of the Association of American Physicians*, 111(5), (1999), 417-422

Samstein, B., et al., "Physiologic and Immunologic Hurdles to Xenotransplantation", *Journal of the American Society of Nephrology*,12, (2001), 182-193.

Sarikaya, Ayda, et al., "Antimicrobial Activity Associated With Extracellular Matrices", *Tissue Engineering*, 8(1), (Feb. 2002), 63-71.

Schaefer, Saul, et al., "Clinical and hemodynamic characteristics of patients with inducible pulsus alternans", *American Heart Journal*, vol. 115, No. 6, (Jun. 1988), 1251-7.

Schram, G., et al., "Differential Distribution of Cardiac Ion Channel Expression as a Basis Function for Regional Specialization in Electrical Function", *Circulation Research*, 90, (2002), 939-950.

Schuldiner, M., et al., "Effects of Eight Growth Factors on the Differentiation of Cells Derived From Human Embryonic Stem Cells", *Proc. Natl. Acad. Sci. USA*, 97(21), (Oct. 10, 2000), 11307-11312.

Semenza, G. L., et al., "Hypoxia-inducible nuclear factors bind to an enhancer element located 3' to the human erythropoietin gen", *Proc Natl Acad Sci USA*, 88(13), (1991), 5680-5684.

Semenza, G. L., et al., "Transcriptional Regulation of Genes Encoding Glycolytic Enzymes By Hypoxia-Inducible Factor 1", *The Journal of Biological Chemistry*, 269(38), (1994), 23757-23763.

Shimizu, T., et al., "Electrically Communicating Three-Dimensional Cardiac Tissue Mimic Fabricated by Layered Cultured Research Cardiomyocyte Sheets", *J. Biomedical Materials.*, 60, (2004), 110-117.

Shimizu, T., et al., "Cell Sheet Engineering for Myocardial Tissue Reconstruction", *Biomaterials*, 24 13), (Jun. 2003), 2309-2316.

Shin, H., et al., "Biomimetic materials for tissue engineering", *Biomaterials* 24, (Nov.2003), 4353-4364.

Shockett, P., et al., "A modified Tetracycline-Regulated System Provides Autoregulatory, Inducible Gene Expression in Cultured Cells and Transgenic Mice", *Proc. Natl Acad Sci USA*, 92(14), (1995), 6522-6526.

Sih, H. J., "Implantable Medical Devices Comprising Isolated Extracellular Matrix", U.S. Appl. No. 11/017,432, filed Dec. 20, 2004, 87 pgs.

Smith, D., et al., "Influence of the Aortic Component of the Second Heart Sound on Left Ventricular Maximal Negative dP/dt in the Dog", *Am. J. Cardiol.*, 55: 205, (1985), 205-209.

Srour, E. F, et al., "Ex Vivo Expansion of Hematopoietic Stem and Progenitor Cells: Are We There Yet?", *The Journal of Hematotherapy*, 8, (1999), 93-102.

Stanley, W, et al., "Energy metabolism in the normal and failing heart: potential for therapeutic interventions", *Heart Fail Rev.*, (Apr. 2002), 115-130.

Stanley, W, "Partial fatty acid oxidation inhibitors for stable angina", *Expert Opin Investiq Drugs*, 11(5), (May 2002), 615-629.

Stock, U. A., et al., "Tissue Engineering: Current State and Prospects", *Annu. Rev Med.*, 52, (2001), 443-451.

Stolen, C., et al., "Method and Apparatus for Preconditioning of Cells", U.S. Appl. No. 11/424 066 filed Jun. 14 2006, 36 pgs.

Suematsu, Y., et al., "$_{L\text{-}Arginine\ given\ after\ ischaemic\ preconditioning\ can\ enhance\ cardioprotection\ in\ isolated\ rat\ hearts}$", *European Journal of Cardio-thoracic Surgery*, 19, (2001), 873-879.

Sukenaga, Y., et al., "Development of the chymase inhibitor as an anti-tissue-remodeling drug: myocardial infarction and some other possibilities", *Jap J Pharmacol*, 90(3), (2002), 218-222.

Suzuki, K., et al., "Cell Transplantation for the Treatment of Acute Myocardial Infarction Using Vascular Endothelial Growth Factor-Expressing Skeletal Myoblasts", *Circulation*: 104(Suppl I), (2001), pp. I-207-I-212.

Taylor, D. A., et al., "Delivery of primary autologous skeletal myoblasts into rabbit heart by coronary infusion: a potential approach to myocardial repair", *Proc Assoc Am Phys*, 109(3), (May 1997), 245-253.

Taylor, D. A, et al., "Regenerating Functional Myocardium: Improved Performance after Skeletal Myoblast Transplantation", *Nature Medicine*, 4(8), (Aug. 1998), 929-933.

Terracio, L., et al., "Effects of Cyclic Mechanical Stimulation of the Cellular Components of the Heart: In Vitro.", *In Vitro Cellullar & Develomental Biology*, 24(1), (Jan. 1988), 53-58.

Thijssen, V. J. L., et al., "Analysis of Altered Gene Expression During Sustained Atrial Fibrillation", *Cardiovascular Research*, 54, (2002), 427-437.

Tomaselli, F., et al., "Photodynamic Therapy Enhanced by Hyperbaric Oxygen in Acute Endoluminal Palliation of Malignant Bronchial Stenosis (Clinical Pilot Study in 40 Patients)", *European Journal of Cardio-thoracic Surgery*, 19, (2001), 549-554.

Towbin, J. A., et al., "Chapter 3—Genetics and Cardiac Arrhythmias", *In Advances in Pediatrics*, vol. 29, Published by Mosby, Inc., (2002), 87-129.

Tran, N et al., "Autologous Cell Transplantation and Cardiac Tissue Engineering: Potential Applications in Heart Failure", *Biorheology*, 40(1-3), (2003), 411-15.

Van Gelder, I. C., et al., "Alterations in Gene Expression of Proteins Involved in the Calcium Handling in Patients with Atrial Fibrillation", *J Cardiovasc Electrophysical*, 10, (1999), 552-560.

Verma, I. M, et al., "Gene Therapy—Promises, Problems and Prospects", *Nature*, 389, (Sep. 18, 1997), 239-242.

Villarreal, F. J., et al., "Human cardiac fibroblasts and receptors for angiotensin II and bradykinin: A potential role for bradykinin in the modulation of cardiac extracellular matrix", *Basic research in cardiology*, 93 Supp 3, (1998), pp. s004-s007.

Walter, D. H., et al., "Endothelial progenitor cells: regulation and contribution to adult neovascularization", *Herz*, 27(7), 2002, 579-588.

Walther, W., et al., "Cell Type Specific and Inducible Promoters for Vectors in Gene Therapy as an Approach for Cell Targeting", *Journal of Molecular Medicine*, 74, (1996), 379-392.

Wang, G. L., et al., "Molecular basis of hypoxia-induced erythropoietin expression", *Curr Opin Hematol.*, 3(2), (Mar. 1996), 156-162.

Wang, L., et al., "Mutation of MEF2A in an inherited disorder with features of coronary artery disea", *Science*, 302(5650), (Nov. 28, 2003), 1578-81.

Washizu, M., et al., "Handling Biological Cells Using a Fluid Integrated Circuit", *IEEE Transactions on Industry Applications*, 26(2), (Mar./Apr. 1990), 352-358.

Wattanapitayakul, S. K., et al., "Recent Developments in Gene Therapy for Cardiac Disease", *Biomedical & Pharmacotherapy*, 54, (2000), 487-504.

Weintraub, H., "The *myoD* Gene Family: Nodal Point During Specification of the Muscle Cell Lineage", *Science*, 251(4995), (1991), 761-766.

Westlund, R., "Lead Electrode Incorporating Extracellular Matrix", U.S. Appl. No. 11/017,238, filed Dec. 20 2004, 85 pgs.

Willey, C. D., et al., "Focal Complex Formation in Adult Cardiomyocytes is Accompanied by the Activation of β3 Integrin and c-Src", *Journal of Molecular and Cellular Cardiology*, 35, (2003), 671-683.

Wobus, A. M, et al., "Embryonic Stem CellDerived Cardiac Differentiation: Modulation of Differentiation and "Loss-of Function" Analysis In Vitro", *TCM*, vol. 8, No. 2,, (1998), 64-74.

Woldbaek, P. R., et al., "Increased cardiac Il-18 mRNA, pro-IL-18 and plasma IL-18 after myocardial infarction in the mouse; a potential role in cardiac dysfunction", *Cardiovascular Research*, 59, (2003), 122-131.

Wolff, A, et al., "Metabolic approaches to the treatment of ischemic heart disease: the clinicians' perspective", *Heart Fail Rev.*, (Apr. 2002), 187-203.

Wolfrum, S., et al., "Acute Reduction of Myocardial Infarct Size By a Hydroxymethyl Glutaryl Coenzyme A Reductase Inhibitor Is Mediated By Endothelial Nitric Oxide Synthase", *J. Cardiovas Pharmacol*, vol. 41, No. 3, (Mar. 2003), 474-480.

Wunderlich, C., "Acute Inhibition of Myoglobin Impairs Contractility and Energy State of iNOS-Overexpressing Hearts", *Circulation Research*, 92, (2003), 1352-1358.

Wurm, F. M., et al., "Inducible Overproduction of the Mouse c-myc Protein in Mammalian Cells", *Proc Natl Acad Sci USA.*, 83(15), (Aug. 1986), 5414-5418.

Wyman, T, et al., "Promoter-Activated Expression of Nerve Growth Factor for Treatment of Neurodegenerative Diseases", *Gene Therapy*, 6, (1999), 1648-1660.

Wynn, R, "Cardiovascular drugs and dental considerations", *Cardiovascular drugs and dental considerations, J Calif Dent Assoc.*, 28(7), (Jul. 2000), 9-26.

Xu, Chunhui, et al., "Characterization and enrichment of cardiomyocytes derived from human embryonic stem cells", *Circ Res.*, 91(6), (2002), 501-508.

Yagi, A., et al., "Anti-inflammatory constituents, aloesin and aloemannan in *Aloe* species and effects of tanshinon VI in *Salvia miltiorrhiza* on heart", *J Pharm Soc Japan*, 123(7), (Jul. 2003), 517-532.

Yamamoto, K., et al., "Regulation of cardiomyocyte mechanotransduction by the cardiac cycle", *Circulation*. vol. 103, 2001, 1459-1464.

Yao, M., et al., "Long-Term Outcome of Fetal Cell Transplantation on Postinfarction Ventricular Remodeling and Function", *Journal of Molecular and Cellular Cardiology*, 35, (2003), 661-670.

Zhu, F., et al., "Purification, Characterization and Evaluation of Antibacterial Peptide from Resorbable Tissue Scaffold", (Abstract No. BIOT 137), *Abstracts of Papers American Chemical Society*, 224(1-2), (2002), 3 pgs.

Zhuang, J., et al., "Pulsatile Stretch Remodels Cell-to-Cell Communication in Cultured Myocytes", *Circ Res.*, 87(4), (2000), 316-322.

Zimmermann, W.-H., et al., "Engineered Heart Tissue for Regeneration of Diseased Hearts", *Biomaterials*, 25, (2004), 1639-1647.

Zimmermann, W.-H., et al., "Tissue Engineering of a Differentiated Cardiac Muscle Construct", *Circ Res.*, 90(2), (2002), 223-230.

Zou, Y., et al., "Heat Shock Transcription Factor 1 Protects Cardiomyocytes From Ischemia/Reperfusion Injury", *Circulation*, 108(24), (2003), 3024-3030.

"U.S. Appl. No. 11/017,432, Final Office Action mailed Mar. 19, 2010", 15 pgs.

Coombes, A. G, et al., "Biocomposites of non-crosslinked natural and synthetic polymers", *Biomaterials*, 23(10), (May 2002), 2113-8.

Everaerts, F., et al., "Quantification of carboxyl groups in carbodiimide cross-linked collagen sponges", *J Biomed Mater Res A.*, 83(4), (Dec. 15, 2007), 1176-83.

Petite, H., et al., "Use of diphenylphosphorylazide for cross-linking collagen-based biomaterials", *J Biomed Mater Res.*, 28(2), (Feb. 1994), 159-65.

Vaissiere, G., et al., "Comparative analysis of different collagen-based biomaterials as scaffolds for long-term culture of human fibroblasts", *Med Biol Eng Comput.*, 38(2), (Mar. 2000), 205-10.

Brightman, A. O., et al., "Time-Lapse Confocal Reflection Microscopy of Collagen Fibrillogenesis and Extracellular Matric Assembly", Biopolymers, vol. 54, (2000), 222-234.

Rault, I., et al., "Evaluation of different chemical methods for cross-linking collagen gel, films and sponges", Journal of Materials Science: Materials in Medicine, 7, (1996), 215-221.

"U.S. Appl. No. 11/017,237, Final Office Action mailed Nov. 15, 2010", 14 pgs.

"U.S. Appl. No. 11/017,237, Non-Final Office Action mailed May 27, 2010", 12 pgs.

"U.S. Appl. No. 11/017,237, Response filed Sep. 27, 2010 to Non Final Office Action mailed May 27, 2010", 11 pgs.

"U.S. Appl. No. 11/017,237, Response filed May 12, 2010 to Final Office Action mailed Jan. 25, 2010", 12 pgs.

"U.S. Appl. No. 11/017,432 Non-Final Office Action mailed Aug. 25, 2010", 18 pgs.

"U.S. Appl. No. 11/017,432, Response filed Jun. 21, 2010 to Final Office Action mailed Mar. 19, 2010", 16 pgs.

"U.S. Appl. No. 11/017,432, Response filed Nov. 24, 2010 to Non Final Office Action mailed Aug. 25, 2010", 20 pgs.

"U.S. Appl. No. 11/017,627 Notice of Allowance mailed Oct. 18, 2010", 8 pgs.

"U.S. Appl. No. 11/017,627, Final Office Action mailed Jun. 16, 2010", 16 pages.

"U.S. Appl. No. 11/017,627, Notice of Allowance mailed Feb. 2, 2011", 7 pgs.

"U.S. Appl. No. 11/017,627, Response filed Aug. 10, 2010 to Final Office Action mailed Jun. 16, 2010", 17 pgs.

"U.S. Appl. No. 10/722,115, Non-Final Office Action mailed Apr. 1, 2009", 14 pgs.

"U.S. Appl. No. 10/722,115, Response filed Aug. 3, 2009 to Non Final Office Action mailed Apr. 1, 2009", 10 pgs.

"U.S. Appl. No. 10/723,258 , Notice of Allowance mailed Jul. 22, 2009", 4 pgs.

"U.S. Appl. No. 10/723,258, Final Office Action mailed Apr. 6, 2009", 5 pgs.

"U.S. Appl. No. 10/723,258, Response filed Jun. 8, 2009 to Final Office Action mailed Apr. 6, 2009", 7 pgs.

"U.S. Appl. No. 10/788,906, Examiner Interview Summary mailed Apr. 23, 2007", 3 pgs.

"U.S. Appl. No. 10/788,906, Examiner Interview Summary mailed Jun. 11, 2008", 2 pgs.

"U.S. Appl. No. 10/788,906, Final Office Action mailed Mar. 18, 2010", 9 pgs.

"U.S. Appl. No. 10/788,906, Non-Final Office Action mailed Jun. 22, 2009", 9 pgs.

"U.S. Appl. No. 10/788,906, Response filed Feb. 20, 2008 to Final Office Action mailed Dec. 4, 2007", 26 pgs.

"U.S. Appl. No. 10/788,906, Response filed Apr. 9, 2009 to Final Office Action mailed Dec. 10, 2008", 24 pgs.

"U.S. Appl. No. 10/788,906, Response filed Oct. 24, 2005 to Restriction Requirement mailed Sep. 23, 2005", 23 pgs.

"U.S. Appl. No. 10/788,906, Restriction Requirement mailed Sep. 23, 2005", 12 pgs.

"U.S. Appl. No. 10/862,716, Non-Final Office Action mailed May 1, 2009", 9 pgs.

"U.S. Appl. No. 10/862,716, Notice of Allowance mailed Mar. 23, 2010", 4 pgs.

"U.S. Appl. No. 10/862,716, Response filed Feb. 4, 2009 to Restriction Requirement mailed Dec. 5, 2009", 23 pgs.

"U.S. Appl. No. 10/862,716, Response filed Jun. 30, 2009 to Non Final Office Action mailed May 1, 2009",10 pgs.

"U.S. Appl. No. 11/017,237, Response filed Feb. 15, 2011 to Final Office Action mailed Nov. 15, 2010", 13 pgs.

"U.S. Appl. No. 11/017,432, Final Office Action mailed Feb. 17, 2011", 17 pgs.

Hodde, J. P, et al., "Retention of endothelial cell adherence to porcine-derived extracellular matrix after disinfection and sterilization", Tissue Eng., 8(2), (Apr. 2002), 225-34.

Livesey, S., et al., "Decellularized porcine heart valves as templates for host cell repopulation.", Presented at Workshop on Prosthetic Heart Valves: Future Technologies, Georgia Institute of Technology, (1998) (no copy available).

US 6,875,206, 04/2005, Ponzi (withdrawn)

* cited by examiner

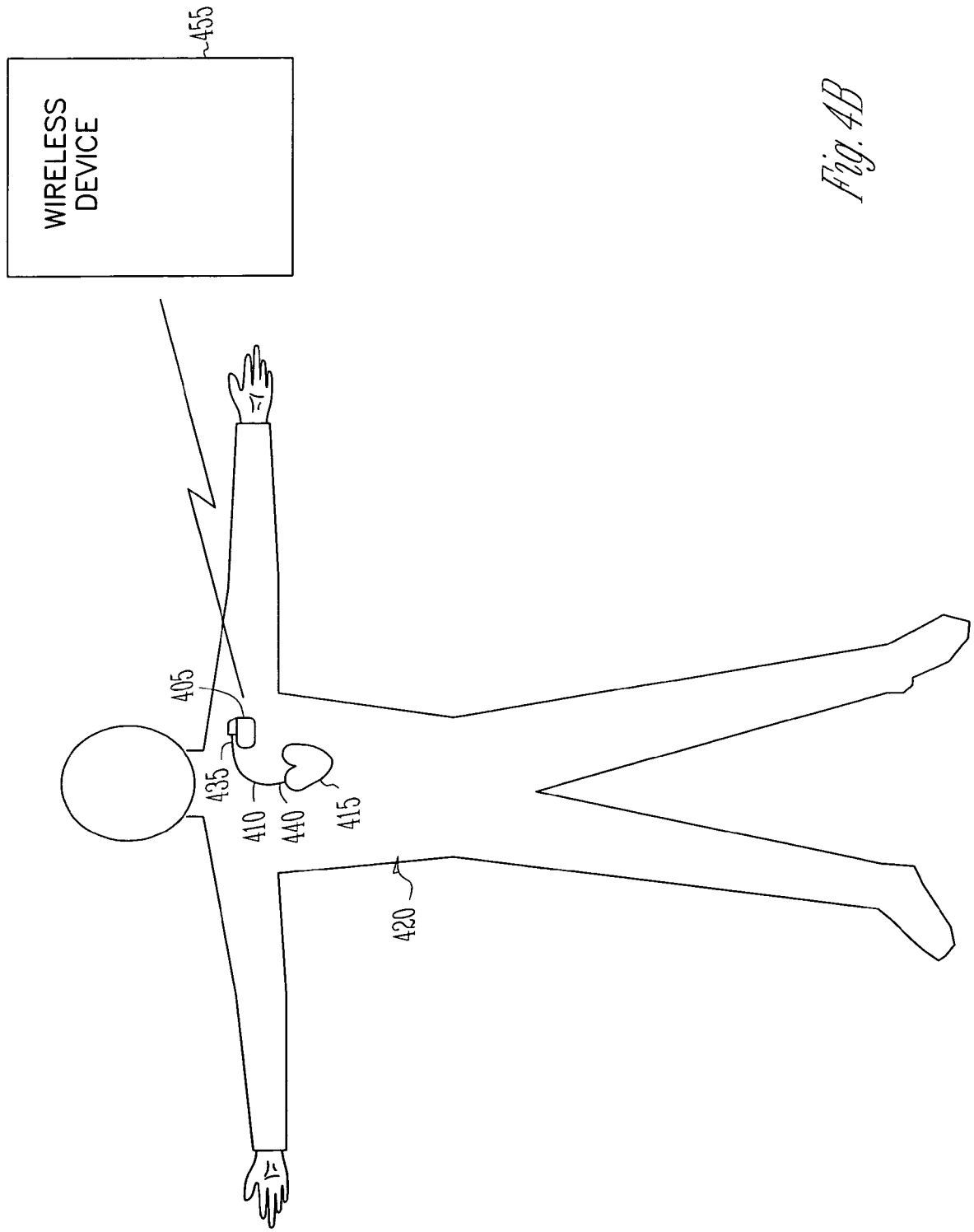

LEAD ELECTRODE INCORPORATING EXTRACELLULAR MATRIX

CROSS-REFERENCE TO RELATED APPLICATION

This application is related to co-pending, commonly assigned U.S. patent application Ser. No. 11/017627, entitled "EPICARDIAL PATCH INCLUDING ISOLATED EXTRACELLULAR MATRIX WITH PACING ELECTRODES," filed on Dec. 20, 2004, U.S. patent application Ser. No. 11/017237, entitled "USE OF EXTRACELLULAR MATRIX AND ELECTRICAL THERAPY," filed on Dec. 20, 2004, and U.S. patent application Ser. No. 11/017432, entitled "IMPLANTABLE MEDICAL DEVICES COMPRISING ISOLATED EXTRACELLULAR MATRIX," filed on Dec. 20, 2004, which are hereby incorporated by reference in their entirety.

TECHNICAL FIELD

This application relates generally to implantable medical devices and, more particularly, to implantable devices incorporating extracellular matrix.

BACKGROUND

The heart is the center of a person's circulatory system. It includes an electro-mechanical system performing two major pumping functions. The heart includes four chambers: right atrium (RA), right ventricle (RV), left atrium (LA), and left ventricle (LV). The left portions of the heart, including LA and LV, draw oxygenated blood from the lungs and pump it to the organs of a body to provide the organs with their metabolic needs for oxygen. The right portions of the heart, including RA and RV, draw deoxygenated blood from the organs of the body and pump it to the lungs where the blood gets oxygenated. The efficiency of the pumping functions, indicative whether the heart is normal and healthy, is indicated by measures of hemodynamic performance, such as parameters related to intracardiac blood pressures and cardiac output.

In a normal heart, the sinoatrial node, the heart's natural pacemaker, generates electrical impulses, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions indicated by a normal hemodynamic performance. A blocked or otherwise abnormal electrical conduction and/or deteriorated myocardial tissue cause dysynchronous contraction of the heart, resulting in poor hemodynamic performance, including a diminished blood supply to the organs of the body. The condition where the heart fails to pump enough blood to meet the body's metabolic needs is known as heart failure.

The adult myocardium is incapable of repairing itself after an injury. Such an injury may result from, for example, myocardial infarction (MI), which is the necrosis of portions of the myocardial tissue resulted from cardiac ischemia, a condition in which the myocardium is deprived of adequate oxygen and metabolite removal due to an interruption in blood supply. The adult heart lacks a substantial population of precursor, stem cells, or regenerative cells. Therefore, after the injury, the heart lacks the ability to effectively regenerate cardiomyocytes to replace the injured cells of the myocardium. Each injured area eventually becomes a fibrous scar that is non-conductive and non-contractile. Consequently, the overall contractility of the myocardium is weakened, resulting in decreased cardiac output. As a physiological compensatory mechanism that acts to increase the cardiac output, the LV diastolic filling pressure increases as the pulmonary and venous blood volume increases. This increases the LV preload, including the stress on the LV wall before the LV contracts to eject blood. The increase of the LV preload leads to progressive change of the LV shape and size, a process referred to as remodeling. Remodeling is initiated in response to a redistribution of cardiac stress and strain caused by the impairment of contractile function in the injured tissue as well as in nearby and/or interspersed viable myocardial tissue with lessened contractility due to the infarct. The remodeling starts with expansion of the region of the injured tissue and progresses to a chronic, global expansion in the size and change in the shape of the entire LV. Although the process is initiated by the compensatory mechanism that increases cardiac output, the remodeling ultimately leads to further deterioration and dysfunction of the myocardium. Consequently, the myocardial injury, such as resulted from MI, results in impaired hemodynamic performance and a significantly increased risk of developing heart failure.

Thus, there is a need to improve the properties of implanted medical devices.

SUMMARY

Native extracellular matrix (ECM) is continuously formed and then degraded by matrix metalloproteinases which along with their natural antagonists, the tissue-inhibiting metalloproteinases, regulate and determine the matrix turnover in living tissue. Bioscaffolds such as isolated ECM can be used as an interface between a mammalian body and an electrode such as a pacing electrode to improve wound healing, e.g., to modulate fibrosis and/or to promote localization of cells, such as stem cells, and/or formation of (e.g., differentiation of stem cells to) electrically excitable cells or tissue, e.g., myocardial cells or tissue. For example, isolated ECM can be used as a coating on one or more lead electrodes to modulate, e.g., decrease (inhibit), fibrotic capsule formation around the electrode(s) after lead implantation. The use of a cardiac pacing lead having an electrode coated with isolated ECM may also promote localization and/or differentiation of stem cells at the site of lead implantation, which allows for repair and/or regeneration of desirable tissue at the site. Thus, once such a lead is implanted, cells, e.g., endogenous stem cells, can migrate into the isolated ECM and proliferate and/or differentiate. In addition, isolated ECM may be used as a delivery device for one or more agents such as donor (exogenously introduced) cells and cytokines by contacting in vitro, for instance, by infusing, isolated ECM with cells and/or one or more cytokines. In one embodiment, donor cells and/or one or more cytokines are contacted with isolated ECM prior to or at the time of device implantation, e.g., prior to applying and/or affixing the isolated ECM to the one or more electrodes. Once a device with isolated ECM is placed in an animal, e.g., a mammal, the implanted isolated ECM is replaced with newly synthesized ECM provided by endogenous cells which localize to the isolated ECM or exogenously introduced cells, e.g., those seeded on the isolated ECM prior to implantation or those administered to the mammal which localize to the isolated ECM after the isolated ECM containing device is implanted.

The invention thus provides a lead comprising one or more electrodes, e.g., pacing electrodes, the surface(s) of which integrates isolated ECM (an ECM scaffold). Isolated ECM may be applied to and/or affixed to at least a portion of the surface of one or more electrodes. In one embodiment, isolated ECM comprises donor cells and/or one or more cytokines. In one embodiment, one or more cytokines are contacted with isolated ECM, e.g., so that the one or more cytokines are coated on and/or embedded in the isolated ECM which itself has been applied and/or affixed to the surface of one or more electrodes. In another embodiment, one or more cytokines are contacted with isolated ECM prior to applying and/or affixing the isolated ECM to the surface of the one or more electrodes. In yet another embodiment, one or more cytokines are administered, for instance, intravenously administered, prior to, during and/or after, or any combination thereof, lead implantation. In one embodiment, one or more immunosuppressive agents are administered, for instance, intravenously administered, prior to, during and/or after, or any combination thereof, lead implantation and/or donor tissue or cell administration, and optionally for at least 1 to 2 weeks post implantation, e.g., to allow for ECM remodeling.

Also provided is a method comprising applying isolated ECM to one or more electrodes, e.g., in amount effective to modulate fibrosis and/or enhance excitable cell or tissue formation at the site of implantation of a lead which includes the one or more electrodes. Further provided are methods of using such leads, e.g., in a method to enhance desirable tissue repair in a mammal subjected implantation of a lead. The method includes introducing to a mammal a lead comprising one or more electrodes which include isolated ECM.

BRIEF DESCRIPTION OF THE FIGURES

FIG. 4B is a diagram showing a wireless device in communication with an implantable device for management of the implanted device and therapy according to one embodiment of the present invention.

DETAILED DESCRIPTION

Figure 1:
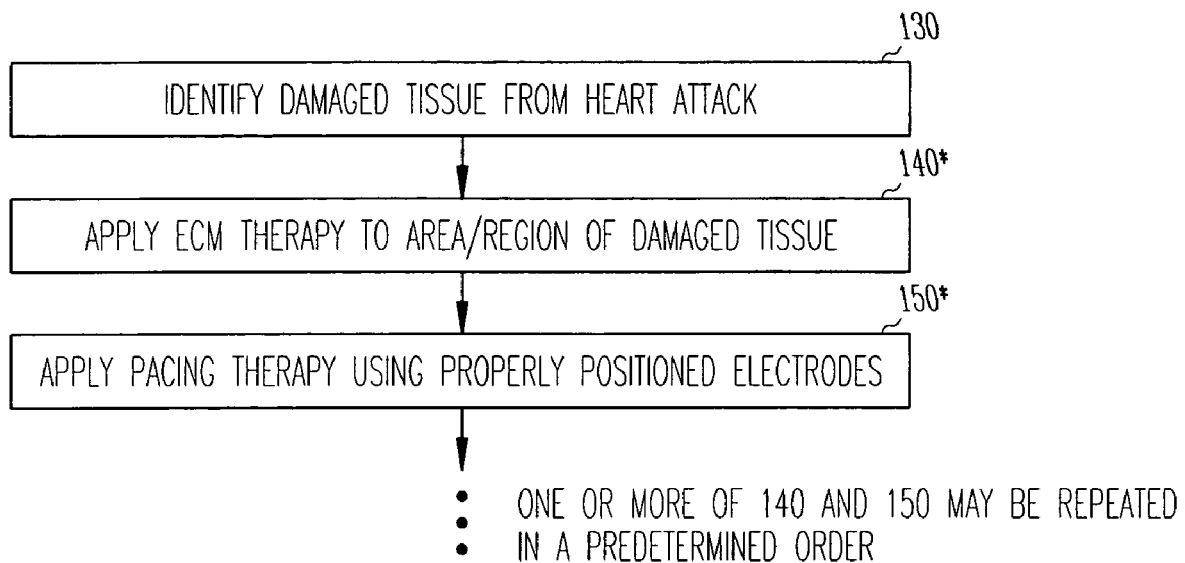
FIG. 1 is a flow diagram for combined isolated ECM and electrical therapies.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

DEFINITIONS

A "cytokine" is a relatively low molecular weight protein secreted by cells, e.g., cells of the immune system, for the purpose of altering the function(s) of those cells and/or adjacent cells. Cytokines include interleukins, e.g., molecules which regulate the inflammatory and immune response, as well as growth and colony stimulating factors. By "growth factor" is meant an agent that, at least, promotes cell growth or induces phenotypic changes. Exemplary growth factors include, but are not limited to, fibroblast growth factor (FGF), vascular endothelial growth factor (VEGF), hepatocyte growth factor (HGF), transforming growth factor (TGF), platelet derived growth factor (PDGF), granulocyte colony stimulatory factor (G-CSF), placental GF, stem cell factor (SCF), or insulin-like growth factor (IGF).

A "vector" or "construct" (sometimes referred to as gene delivery or gene transfer "vehicle") refers to a macromolecule or complex of molecules comprising a polynucleotide to be delivered to a host cell, either in vitro or in vivo. The polynucleotide to be delivered may comprise a sequence of interest for gene therapy. Vectors include, for example, transposons and other site-specific mobile elements, viral vectors, e.g., adenovirus, adeno-associated virus (AAV), poxvirus, papillomavirus, lentivirus, herpesvirus, foamivirus and retrovirus vectors, and including pseudotyped viruses, liposomes and other lipid-containing complexes, and other macromolecular complexes capable of mediating delivery of a polynucleotide to a host cell, e.g., DNA coated gold particles, polymer-DNA complexes, liposome-DNA complexes, liposome-polymer-DNA complexes, virus-polymer-DNA complexes, e.g., adenovirus-polylysine-DNA complexes, and antibody-DNA complexes. Vectors can also comprise other components or functionalities that further modulate gene delivery and/or gene expression, or that otherwise provide beneficial properties to the cells to which the vectors will be introduced. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

A "recombinant viral vector" refers to a viral vector comprising one or more heterologous genes or sequences. Since many viral vectors exhibit size constraints associated with packaging, the heterologous genes or sequences are typically introduced by replacing one or more portions of the viral genome. Such viruses may become replication-defective, requiring the deleted function(s) to be provided in trans during viral replication and encapsidation (by using, e.g., a helper virus or a packaging cell line carrying genes necessary for replication and/or encapsidation). Modified viral vectors in which a polynucleotide to be delivered is carried on the outside of the viral particle have also been described (see, e.g., Curiel et al., *Proc. Natl. Acad. Sci. USA*, 88:8850 (1991)).

"Gene delivery," "gene transfer," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, iontophoresis, "gene gun" delivery and various other techniques used for the introduction of polynucleotides, e.g., targeted recombination). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art.

By "transgene" is meant any piece of a nucleic acid molecule (for example, DNA) which is inserted by artifice into a cell either transiently or permanently, and becomes part of the organism if integrated into the genome or maintained extrachromosomally. Such a transgene may include a gene which is partly or entirely heterologous (i.e., foreign) to the transgenic organism, or may represent a gene homologous to an endogenous gene of the organism.

By "transgenic cell" is meant a cell containing a transgene. For example, a stem cell transformed with a vector containing an expression cassette can be used to produce a population of cells having altered phenotypic characteristics.

The term "wild-type" refers to a gene or gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

"Vasculature" or "vascular" are terms referring to the system of vessels carrying blood (as well as lymph fluids) throughout the mammalian body.

"Blood vessel" refers to any of the vessels of the mammalian vascular system, including arteries, arterioles, capillaries, venules, veins, sinuses, and vasa vasorum.

"Artery" refers to a blood vessel through which blood passes away from the heart. Coronary arteries supply the tissues of the heart itself, while other arteries supply the remaining organs of the body. The general structure of an artery consists of a lumen surrounded by a multi-layered arterial wall.

The term "transduction" denotes the delivery of a polynucleotide to a recipient cell either in vivo or in vitro, via a viral vector and preferably via a replication-defective viral vector, such as via a recombinant AAV.

The term "heterologous" as it relates to nucleic acid sequences such as gene sequences and control sequences, denotes sequences that are not normally joined together, and/ or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature, i.e., a heterologous promoter. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention.

By "DNA" is meant a polymeric form of deoxyribonucleotides (adenine, guanine, thymine, or cytosine) in double-stranded or single-stranded form found, inter alia, in linear DNA molecules (e.g., restriction fragments), viruses, plasmids, and chromosomes. In discussing the structure of particular DNA molecules, sequences may be described herein according to the normal convention of giving only the sequence in the 5' to 3' direction along the nontranscribed strand of DNA (i.e., the strand having the sequence complementary to the mRNA). The term captures molecules that include the four bases adenine, guanine, thymine, or cytosine, as well as molecules that include base analogues which are known in the art.

As used herein, the terms "complementary" or "complementarity" are used in reference to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

A "gene," "polynucleotide," "coding region," or "sequence" which "encodes" a particular gene product, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. Thus, a gene includes a polynucleotide which may include a full-length open reading frame which encodes a gene product (sense orientation) or a portion thereof (sense orientation) which encodes a gene product with substantially the same activity as the gene product encoded by the full-length open reading frame, the complement of the polynucleotide, e.g., the complement of the full-length open reading frame (antisense orientation) and optionally linked 5' and/or 3' noncoding sequence(s) or a portion thereof, e.g., an oligonucleotide, which is useful to inhibit transcription, stability or translation of a corresponding mRNA. A transcription termination sequence will usually be located 3' to the gene sequence.

An "oligonucleotide" includes at least 7 nucleotides, preferably 15, and more preferably 20 or more sequential nucleotides, up to 100 nucleotides, either RNA or DNA, which correspond to the complement of the non-coding strand, or of the coding strand, of a selected mRNA, or which hybridize to the mRNA or DNA encoding the mRNA and remain stably bound under moderately stringent or highly stringent conditions, as defined by methods well known to the art, e.g., in Sambrook et al., A Laboratory Manual, Cold Spring Harbor Press (1989).

The term "control elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence. Thus, a "promoter," refers to a polynucleotide sequence that controls transcription of a gene or coding sequence to which it is operably linked. A large number of promoters, including constitutive, inducible and repressible promoters, from a variety of different sources, are well known in the art.

By "enhancer element" is meant a nucleic acid sequence that, when positioned proximate to a promoter, confers increased transcription activity relative to the transcription activity resulting from the promoter in the absence of the enhancer domain. Hence, an "enhancer" includes a polynucleotide sequence that enhances transcription of a gene or coding sequence to which it is operably linked. A large number of enhancers, from a variety of different sources are well known in the art. A number of polynucleotides which have promoter sequences (such as the commonly-used CMV promoter) also have enhancer sequences.

"Operably linked" refers to a juxtaposition, wherein the components so described are in a relationship permitting them to function in their intended manner. By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. A promoter is operably linked to a coding sequence if the promoter controls transcription of the coding sequence. Although an operably linked promoter is generally located upstream of the coding sequence, it is not necessarily contiguous with it. An enhancer is operably linked to a coding sequence if the enhancer increases transcription of the coding sequence. Operably linked enhancers can be located upstream, within or downstream of coding sequences. A polyadenylation sequence is operably linked to a coding sequence if it is located at the downstream end of the coding sequence such that transcription proceeds through the coding sequence into the polyadenylation sequence. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. Thus, a signal or targeting peptide sequence is operably linked to another protein if the resulting fusion is secreted from a cell as a result of the presence of a secretory signal peptide or into an organelle as a result of the presence of an organelle targeting peptide.

By "mammal" is meant any member of the class Mammalia including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. An "animal" includes vertebrates such as mammals, avians, amphibians, reptiles and aquatic organisms including fish.

By "derived from" is meant that a nucleic acid molecule was either made or designed from a parent nucleic acid molecule, the derivative retaining substantially the same functional features of the parent nucleic acid molecule, e.g., encoding a gene product with substantially the same activity as the gene product encoded by the parent nucleic acid molecule from which it was made or designed.

By "expression construct" or "expression cassette" is meant a nucleic acid molecule that is capable of directing transcription. An expression construct includes, at the least, a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

The term "isolated" when used in relation to a nucleic acid, peptide, polypeptide, virus or complex of biological molecules, e.g., isolated ECM, refers to a nucleic acid sequence, peptide, polypeptide, virus or complex of molecules that is identified and/or separated from at least one contaminant nucleic acid, polypeptide, virus, or other biological component with which it is ordinarily associated in its natural source. Isolated nucleic acid, peptide, polypeptide, virus or ECM is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (i.e., the molecule may single-stranded), but may contain both the sense and antisense strands (i.e., the molecule may be double-stranded).

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "peptide", "polypeptide" and protein" are used interchangeably herein unless otherwise distinguished to refer to polymers of amino acids of any length. These terms also include proteins that are post-translationally modified through reactions that include glycosylation, acetylation and phosphorylation.

The term "angiogenic" means an agent that alone or in combination with other agents induces angiogenesis, and includes, but is not limited to, fibroblast growth factor (FGF), vascular endothelial growth factor (VEGF), hepatocyte growth factor (HGF), angiogenin, transforming growth factor (TGF), tissue necrosis factor (TNF, e.g., TNF-α), platelet derived growth factor (PDGF), granulocyte colony stimulatory factor (G-CSF), placental GF, IL-8, proliferin, angiopoietin, e.g., angiopoietin-1 and angiopoietin-2, thrombospondin, ephrin-A1, E-selectin, leptin and heparin affinity regulatory peptide.

"Gene regulation" or "Gene regulatory therapy" as used herein includes delivery of one or more gene regulatory signals to regulate gene expression in a gene therapy vector. The gene regulatory signals include signals that trigger a transcriptional control element, e.g., a promoter.

A "user" includes a physician or other caregiver using a system to treat a patient.

By "muscle cell" or "muscle tissue" is meant a cell or group of cells derived from muscle, including, but not limited to, cells and tissue derived from skeletal muscle and cardiac muscle, and in some embodiments includes smooth muscle cells. The term includes muscle cells both in vitro and in vivo. Thus, for example, an isolated cardiomyocyte would constitute a "muscle cell" for purposes of the present invention, as would a muscle cell as it exists in muscle tissue present in a subject in vivo. The term also encompasses both differentiated and nondifferentiated muscle cells, such as myocytes, myotubes, myoblasts, both dividing and differentiated, cardiomyocytes and cardiomyoblasts.

By "cardiac cell" is meant a differentiated cardiac cell (e.g., a cardiomyocyte) or a cell committed to differentiating to a cardiac cell (e.g., a cardiomyoblast or a cardiomyogenic cell).

A "myocyte" is a muscle cell that contains myosin.

A "cardiomyocyte" is any cell in the cardiac myocyte lineage that shows at least one phenotypic characteristic of a cardiac muscle cell. Such phenotypic characteristics can include expression of cardiac proteins, such as cardiac sarcomeric or myofilbrillar proteins or atrial natriuretic factor (ANP), or electrophysiological characteristics. Cardiac sarcomeric or myofibrillar proteins include, for example, atrial myosin heavy chain, cardiac-specific ventricular myosin heavy chain, desmin, N-cadherin, sarcomeric actin, cardiac troponin I, myosin heavy chain, and Na/K ATPase. Electrophysiological characteristics of a cardiomyocyte include, for example, $Na^+$ or $K^+$ channel currents. Similarly, by "skeletal muscle cell" is meant any cell in the skeletal muscle cell lineage that shows at least one phenotypic characteristic of a skeletal muscle cell. Such phenotypic characteristics can include expression of skeletal muscle proteins, such as skeletal muscle-specific transcription factor MyoD or skeletal muscle-specific myosin, or electrophysiological characteristics and morphologic characteristics such as fusion into a multinucleated striated fiber.

By "smooth muscle" is meant any cell in the smooth muscle cell lineage that shows at least one phenotypic characteristic of smooth muscle cells. Such phenotypic characterizations can include expression of smooth muscle proteins or transcripts, such as alpha smooth muscle actin, smooth muscle heavy chain mysosin, or contractile characteristics and morphologic characteristics such as vessel formation.

By "myocardium" is meant the muscular portion of the heart. The myocardium includes three major types of muscle fibers: atrial muscle fibers, ventricular muscle fibers, and specialized excitatory and conductive muscle fibers.

By "cardiac-specific enhancer element" is meant an element, which, when operably linked to a promoter, directs gene expression in a cardiac cell and does not direct gene expression in all tissues or all cell types. Cardiac-specific enhancers of the present invention may be naturally occurring or non-naturally occurring. One skilled in the art will recognize that the synthesis of non-naturally occurring enhancers can be performed using standard oligonucleotide synthesis techniques.

As used herein, a "drug" is an agent that is not a protein which is naturally produced by a cell or tissue, and which, in an effective amount, has a prophylactic or therapeutic effect.

As used herein, an "anti-inflammatory" agent includes but is not limited to propionic acid derivatives, e.g., ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, or fluprofen, or a pharmaceutically acceptable salt thereof; acetic acid derivatives, e.g., indomethacin, sulindac, tolmetin, zomepirac, nabumetone, diclofenac, fenclofenac, alclofenac, bromfenac, ibufenac, aceclofenac, acemetacin, fentiazac, clidanac, etodolac, or oxpinac, or a pharmaceutically acceptable salt thereof; fenamic acid derivatives, e.g., mefenamic acid, meclofenamic acid, flufenamic acid, niflu-minic acid, or tolfenamic acid, or a pharmaceutically acceptable salt thereof; biphenylcarboxylic acid derivatives, e.g., diflunisal or flufenisal, or a pharmaceutically acceptable salt thereof; acid enolcarboxamides, e.g., piroxicam, tenoxicam, lomoxicam, or meloxicam, or a pharmaceutically acceptable salt thereof; diaryl heterocycles with methylsulphonyl or aminosulphonyl substituents, or acid sulphonamides, e.g., nimesulide, and including nabumetone, ketorlac, azapropa-zone, sulindac, podophyllotoxin derivatives, acemetacin, aceclofenac, droxicam, floctafenine, phenylbutazone, pro-glumetacin, tolmetin, celcoxib, rofecoxib, diflunisal, indobufen, flurbiprofen, etodolac, aspirin, azulene, phenace-tin, isopropyl antipyrine, acetaminophen, benzadac, phenylb-utazone, sodium salicylate, salicylamide, sazapyrine, dexamethasone, hydrocortisone, prednisolone or triamcinolone.

As used herein, an "anti-thrombotic" agent includes but is not limited to argatroban, cilostazol, clopidogrel, cloric-romen, dalteparin, daltroban, defibrotide, enoxaparin, indobufen, iloprost, integrelin, isbogrel, lamifiban, lamo-parin, nadroparin, ozagrel, picotamide, plafibride, reviparin sodium, ridogrel, sulfin pyrazone, taprostene, ticlopidine, tin-zaparin, tirofiban, triflusal, tPA, uPA, warfarin, hirudin and other thrombin inhibitors, heparin, thromboplastin activating factor inhibitor, beparin and low molecular weight heparins, such as hirudin, abciximab, and eptofibatide.

As used herein, an "anti-arrhythmic" agent includes but is not limited to sodium channel blockers, β-adrenergic receptor blockers, potassium channel blockers and calcium channel blockers, e.g., verapamil, diltiazem or nifedipine, class 1a agents, e.g., disopyramide, procainamide or quinidine, class Ib agents, e.g., lidocaine, phenytoin, mexiletine, or tocainide, class 1c agents, e.g., encainide, flecainide, propafenone or moricizine, class III agents, e.g., amiodarone, sotalol, or bretylium, quindine, flecainide, propranolol, metoprolol, amiodarone, sotalol, cibenzoline, ajmaline, aprindine or ajmilide.

General Overview

This document discloses, among other things, a method and apparatus for synergistic actions among bioscaffolds such as isolated ECM and electrical therapy of living tissue. Eukaryotic derived bioscaffolds include decellularized xeno-geneic or allogeneic isolated ECM, e.g., ECM isolated from small intestinal submucosa. Isolated ECM is a unique bioma-terial with unique properties, e.g., isolated ECM is biocom-patible, e.g., has low immunogenicity, biodegradable, anti-thrombotic, anti-inflammatory and/or anti-bacterial, and optionally has mechanical and regenerative properties. Thus, when ECM is used with an implanted device for electrical therapy, the performance of that device may be improved. For example, when ECM is used as an external interface layer between a patient and an implanted device such as generator, lead, and/or one or more electrodes of a lead, the chronic performance and patient tolerance of these devices may be improved. For example, the use of a ECM containing device can facilitate wound healing, e.g., by preventing or inhibiting scar tissue formation such as a fibrotic capsule formation around an implanted device so as to result in a device encap-sulated by neointima that is less thrombotic and/or a decrease in the radius from current field generation to excitable tissue. Decreased neointima formation around a lead can improve pacing and defibrillation thresholds for capture and internal defibrillation, as well as reduce thromboembolism risk and thereby improve safety for leads including endocardial left-sided leads (arterial), transvenous left-sided leads, trans-venous right-sided leads, and epicardial leads, reduce peri-cardial adhesions, and/or reduce inflammation associated with lead placement, e.g., epicardial lead placement, which in turn improves healing for endocardial or epicardial leads. In particular, a decrease in the radius from current field genera-tion from an electrode to excitable tissue may lead to lower pacing thresholds and increased device longevity, and option-ally enhanced recruitment of stem cells and excitable cells and/or differentiation of stem cells to excitable cells.

The invention thus provides a therapy to combine the prop-erties, e.g., regenerative/repair and mechanical properties, of isolated ECM (ECM scaffolds), such as ECM isolated from allogeneic or xenogeneic small intestine submucosa, urinary bladder submucosa, and the like, with the active unloading and therapeutic benefit of electrical stimulation delivered locally to an infarct and peri-infarct region, optionally in conjunction with drug therapy. For instance, the use of iso-lated ECM for cardiac repair, such as an isolated ECM sup-port which is applied to cardiac tissue, may result in enhanced transient mechanical support, enhanced angiogenesis, enhanced localization of stem cells, and/or reduced adverse effects, e.g., ventricular remodeling, including reduced fibro-sis, of the heart, thereby leading to enhanced function of an infarcted region. The use of electrical stimulation alters the load and work of myocytes and may enhance the localization, differentiation and/or function of stem cells in the infarcted region. Moreover, the use of electrical stimulation, e.g., pac-ing, may improve ECM therapy.

Biodegradable bioscaffolds such as isolated ECM may be seeded with exogenous agents in vitro such as cells, e.g., autologous or allogeneic cells, that may be derived from either biopsies or stem cells, drugs, cellular molecules such as cytokines, and/or gene therapy vectors. Cells seeded onto bioscaffolds such as isolated ECM proliferate, organize, and produce cellular and extracellular matrix, and metabolize the original (isolated) ECM. The implantation of exogenous agent seeded isolated ECM, such as autologous cell seeded isolated ECM, or unseeded, e.g., substantially acellular, iso-lated ECM that is repopulated by host cells after implantation, can avoid the risks of immunological responses such as rejec-tions (hyperacute and delayed), and, for cell seeded isolated ECM, donor cell-derived viral infections.

In one embodiment, donor cells and electrodes are applied to isolated ECM and the resulting apparatus administered, e.g., by applying and/or affixing the apparatus, to cardiac tissue. In another embodiment, donor cells are applied to isolated ECM and the resulting cell seeded, isolated ECM applied and/or affixed to a cardiac region either before or after electrodes are applied and/or affixed to the region or to the cell seeded, isolated ECM. In one embodiment, the cardiac region includes damaged tissue which is then subjected to electric stimulation, such as pacing-level electrical stimulation, using a pulse generator with properly positioned electrodes. Several embodiments are presented below to provide examples of different therapy apparatus and method. It is understood that other apparatus and method are possible as provided by the attached claims and their equivalents.

Isolation of ECM e.g., xenogeneic ECM, which has been separated from at least one contaminant biological structure with which it is normally associated in its natural state in an organism or in an in vitro cultured cell population. An "isolated ECM support" is a structure formed of isolated ECM which is capable of being attached to the epicardial surface of a heart. Isolated ECM preferably has one or more of the following properties including, but not limited to, inhibition of thrombosis, inhibition of bacterial infection, modulation of fibrosis, inhibition of inflammation, promotion of cell infiltration, promotion of deposition of host derived neomatrix, thereby leading to controlled remodeling with a minimum of scar tissue.

In one embodiment, ECM is isolated from any organ or tissue source including the dermis of the skin, liver, heart (cardiac), alimentary, respiratory, intestinal, urinary or genital tracks of a warm blooded vertebrate. ECM employed in the invention may be from a combination of sources. Isolated ECM may be prepared as a sheet, in particulate form, gel form and the like.

In one embodiment, ECM is isolated from the small intestine. Intestinal submucosal tissue for use in the invention typically comprises the tunica submucosa delaminated from both the tunica muscularis and at least the luminal portions of the tunica mucosa. In one embodiment, the submucosal tissue comprises the tunica submucosa and basilar portions of the tunica mucosa including the lamina muscularis mucosa and the stratum compactum. The preparation of submucosal tissue is described in U.S. Pat. No. 4,902,508 and Bell, In: *Tissue Engineering: Current Perspectives*, Cambridge, Mass., Burkhauser Publishers, pp. 179-189 (1993), the disclosures of which are expressly incorporated herein by reference. For example, a segment of vertebrate intestine, preferably harvested from porcine, ovine or bovine species, or other warm blooded vertebrates, is rinsed free of contents, then split longitudinally to form a sheet and delaminated. In particular, the superficial layers of the tunica mucosa are removed by mechanical delamination. The tissue is then turned to the opposite side and the tunica muscularis externa and tunica serosa are mechanically removed leaving the tunica submucosa and the basilar layers of the tunica mucosa. The remaining tissue represents isolated ECM and may include a small number of intact cells.

In one embodiment, ECM is isolated from the urinary bladder. The wall of the urinary bladder is composed of the following layers: the mucosa (including a transitional epithelium layer and the tunica propria), a submucosa layer, up to three layers of muscle and the adventitia (a loose connective tissue layer)—listed in crossection from luminal to abluminal sides. Urinary bladder submucosa may be prepared from bladder tissue harvested from animals raised for meat production, including, for example, porcine, ovine or bovine species or other warm-blooded vertebrates. For example, the urinary bladder is harvested and thoroughly rinsed in a sterile solution, e.g., sterile water, to remove its contents. The bladder is split open through the apex and bisected to yield roughly equal-sized halves that are prepared separately. The luminal side of the bladder is placed face down and the external muscle layers, i.e., muscularis externa (smooth muscle cell layers and serosa), are removed by mechanical delamination. The transitional epithelium of the urinary bladder is removed by either mechanical or ionic methods (e.g., 1.0 N NaCl treatment) leaving behind tissue corresponding to isolated ECM, e.g., approximately a 50 µM to 80 µM thick sheet of ECM that originally resides between the transitional epithelium and the smooth muscle layers of the urinary bladder, i.e., the submucosa and basement membrane of the transitional epithelium.

In another embodiment, ECM from bladder wall segments or small intestine is prepared using a modification to the technique in Meezan et al. (*Life Sci.*, 17:1721 (1975)). The method in Meezan et al. includes placing tissue fractions in a large volume (100:1) of distilled water containing 0.1% sodium azide and magnetically stirring the mixture for 1-2 hours in order to lyse the cells and release the intracellular contents. The lysed tissue suspension is then centrifuged to yield a firm pellet, and the supernatant discarded. The pellet is suspended in 40 ml of 1M NaCl and 2000 Kunitz units of DNAase (Sigma, Deoxyribonuclease 1) are added and the suspension stirred for 1-2 hours. The mixture is again centrifuged to bring down a firm pellet and the supernatant discarded. The pellet is then suspended in 40 ml of 4% sodium deoxycholate containing 0.1% sodium azide and stirred for 2-4 hours at room temperature. The mixture is centrifuged, the supernatant discarded, and the pellet either washed several times with water by centrifugation and resuspension, or by extensive irrigation on a 44 micron nylon sieve (Kressilk Products, Inc., Monterey Park, Calif.). In the modified method, the time of incubation with sodium deoxycholate and sodium azide is increased and additional washing procedures incorporated. Accordingly, first, the mucosa is scraped off mechanically. Afterwards all cell structures of the remaining tissue are eliminated chemically and enzymatically leaving the acellularized muscularis layer. This is achieved with subsequent exposure to a hypoosmolar and hyperosmolar solutions of crystalloids. In addition, a final treatment with sodium deoxycholate destroys remaining cell structures. After following washing procedures, the resulting material, which provides cross-linked fibres of the submucosa with the remaining muscularis collagen-elastin framework, can be stored in PBS solution, e.g., with antibiotics at 4° C. for a few months.

Isolated ECM can be cut, rolled, or folded.

Fluidized forms of submucosal tissue are prepared by comminuting submucosa tissue by tearing, cutting, grinding, or shearing the harvested submucosal tissue. Thus, pieces of submucosal tissue can be comminuted by shearing in a high speed blender, or by grinding the submucosa in a frozen or freeze-dried state, to produce a powder that can thereafter be hydrated with water or buffered saline to form a submucosal fluid of liquid, gel or paste-like consistency.

The comminuted submucosa formulation can further be treated with an enzymatic composition to provide a homogenous solution of partially solubilized submucosa. The enzymatic composition may comprise one or more enzymes that are capable of breaking the covalent bonds of the structural components of the submucosal tissue. For example, the comminuted submucosal tissue can be treated with a collagenase, glycosaminoglycanase, or a protease, such as trypsin or pepsin at an acidic pH, for a period of time sufficient to solubilize all or a portion of the submucosal tissue protein components. After treating the comminuted submucosa formulation with the enzymatic composition, the tissue is optionally filtered to provide a homogenous solution. The viscosity of fluidized submucosa for use in accordance with this invention can be manipulated by controlling the concentration of the submucosa component and the degree of hydration. The viscosity can be adjusted to a range of about 2 to about 300,000 cps at 25° C. Higher viscosity formulations, for example, gels, can be prepared from the submucosa digest solutions by adjusting the pH of such solutions to about 6.0 to about 7.0.

The present invention also contemplates the use of powder forms of submucosal tissues. In one embodiment, a powder form of submucosal tissue is prepared by pulverizing intestinal submucosa tissue under liquid nitrogen to produce particles ranging in size from 0.01 to 1 mm$^2$ in their largest dimension. The particulate composition is then lyophilized overnight, pulverized again and optionally sterilized to form a substantially anhydrous particulate composite. Alternatively, a powder form of submucosal tissue can be formed from fluidized submucosal tissue by drying the suspensions or solutions of comminuted submucosal tissue.

Submucosal tissue may be "conditioned" to alter the viscoelastic properties of the submucosal tissue. Submucosal tissue is conditioned by stretching, chemically treating, enzymatically treating or exposing the tissue to other environmental factors. The conditioning of submucosal tissue is described in U.S. Pat. No. 5,275,826, the disclosure of which is expressly incorporated herein by reference. In accordance with one embodiment, vertebrate derived submucosal tissues are conditioned to a strain of no more than about 20%.

In one embodiment, the submucosal tissue is conditioned by stretching the tissue longitudinally. One method of "conditioning" the tissue by stretching involves application of a given load to the submucosa for three to five cycles. Each cycle consists of applying a load to the tissue for five seconds, followed by a ten second relaxation phase. Three to five cycles produces a stretch-conditioned material. For example, submucosal tissue can be conditioned by suspending a weight from the tissue, for a period of time sufficient to allow about 10 to 20% or more elongation of the tissue segment. Optionally, the material can be preconditioned by stretching in the lateral dimension.

In one embodiment the submucosal tissue is stretched using 50% of the predicted ultimate load. The "ultimate load" is the maximum load that can be applied to the submucosal tissue without resulting in failure of the tissue (i.e., the break point of the tissue). Ultimate load can be predicted for a given strip of submucosal tissue based on the source and thickness of the material. Accordingly, one method of "conditioning" the tissue by stretching involves application of 50 % of the predicted ultimate load to the submucosa for three to ten cycles. Each cycle consists of applying a load to the material for five seconds, followed by a ten second relaxation phase. The resulting conditioned submucosal tissue has a strain of less than 30%, more typically a strain from about 20% to about 28%. In one embodiment, conditioned the submucosal tissue has a strain of no more than 20%. The term strain as used herein refers to the maximum amount of tissue elongation before failure of the tissue, when the tissue is stretched under an applied load. Strain is expressed as a percentage of the length of the tissue before loading.

Typically the conditioned submucosal tissue is immobilized by clamping, suturing, stapling, gluing (or other tissue immobilizing techniques) the tissue to the support, wherein the tissue is held at its preconditioned length in at least one dimension. In one embodiment, delaminated submucosa is conditioned to have a width and length longer than the original delaminated tissue and the conditioned length and width of the tissue is maintained by immobilizing the submucosa on a support. The support-held conditioned submucosal tissue can be sterilized before or after being packaged.

Preferably, isolated ECM is decellularized, and optionally sterilized, prior to storage and/or use. In one embodiment, isolated ECM has a thickness of about 50 to 250 micrometers, e.g., 100 to 200 micrometers, and is >98% acellular. Numerous methods may be used to decellularize isolated ECM (see, for example, Courtman et al., *J. Biomed. Materi. Res.*, 18:655 (1994); Curtil et al., *Cryobiology*, 34:13 (1997); Livesey et al., Workshop on Prosthetic Heart Valves, Georgia Inst. Tech. (1998); Bader et al., *Eur. J. Cardiothorac. Surg.*, 14:279 (1998)). For instance, treatment of isolated ECM with dilute (0.1%) peracetic acid and rinsing with buffered saline (pH 7.0 to 7.4) and deionized water renders the material acellular with a neutral pH. Alternatively, isolated ECM is thoroughly rinsed under running water to lyse the remaining resident cells, disinfected using 0.1% peracetic acid in ethanol, and rinsed in phosphate buffered saline (PBS, pH=7.4) and distilled water to return its pH to approximately 7.0. Decellularization may be ascertained by hematoxylin-eosin staining.

Isolated, and optionally decellularized, ECM contains a mixture of structural and functional molecules such as collagen type I, III, IV, V, VI; proteoglycans; glycoproteins; glycosaminoglycans; and growth factors in their native 3-dimensional microarchitecture, including proteins that influence cell attachment, gene expression patterns, and the differentiation of cells. Isolated ECM is optionally sterilized and may be stored in a hydrated or dehydrated state.

Isolated ECM may be sterilized using conventional sterilization techniques including tanning with glutaraldehyde, formaldehyde tanning at acidic pH, ethylene oxide treatment, propylene oxide treatment, gas plasma sterilization, gamma radiation, electric beam radiation and peracetic acid sterilization. Sterilization techniques which do not adversely affect the mechanical strength, structure, and biotropic properties of the isolated ECM are preferred. For instance, strong gamma radiation may cause loss of strength of sheets of submucosal tissue. Preferred sterilization techniques include exposing isolated ECM to peracetic acid, low dose gamma irradiation, e.g., 1-4 mRads gamma irradiation or more preferably 1-2.5 mRads of gamma irradiation, or gas plasma sterilization. In one embodiment, peracetic acid treatment is typically conducted at a pH of about 2 to about 5 in an aqueous ethanolic solution (about 2 to about 10% ethanol by volume) at a peracid concentration of about 0.03 to about 0.5% by volume. After isolated ECM is sterilized, it may be wrapped in a porous plastic wrap or foil and sterilized again, e.g., using electron beam or gamma irradiation sterilization techniques. Isolated ECM for implantation is generally subjected to two or more sterilization processes. Terminal sterilization, e.g., with 2.5 mRad (10 kGy) gamma irradiation results in a sterile, pyrogen-free biomaterial. Isolated ECM or isolated, decellularized ECM may then be stored, e.g., at 4° C., until use. Lyophilized or air dried ECM can be rehydrated and used in accordance with this invention without significant loss of its properties. Decellularized and/or sterilized isolated ECM is substantially nonimmunogenic and has high tensile strength. Isolated ECM may, upon implantation, undergo remodeling (resorption and replacement with autogenous differentiated tissue), serve as a rapidly vascularized matrix for support and growth of new tissue, and assume the characterizing features of the tissue(s) with which it is associated at the site of implantation, which may include functional tissue.

In some embodiments, isolated ECM may be subjected to chemical and non-chemical means of cross-linking to modify the physical, mechanical or immunogenic properties of naturally derived ECM (Bellamkondra et al., *J. Biomed. Mater. Res.*, 29:633 (1995)). Chemical cross-linking methods generally involve aldehyde or carbodiimide. Photochemical means of protein cross-linking may also be employed (Bouhadir et al., *Ann. NY Acad. Sci.*, 842:188 (1998)). Cross-linking generally results in a relatively inert bioscaffold material which may induce a fibrous connective tissue response by the host to the scaffold material, inhibit scaffold degradation, and/or inhibit cellular infiltration into the scaffold. ECM scaffolds that are not cross-linked tend to be rapidly resorbed in contrast nonresorbable cross-linked materials or synthetic scaffolds such as Dacron or polytetrafluoroethylene (Bell, *Tissue Engin.*, 1:163 (1995); Bell, *In: Tissue Engineering: Current Perspectives*, Burhauser Pub. pp. 179-189 (1993); Badylak et al., *Tissue Engineering*, 4:379 (1998); Gleeson et al., *J. Urol.*, 148:1377 (1992)).

Cells and Genes for Cell-Based and Gene-Based Therapies

Sources for donor cells in cell-based therapies, including cell-based therapies for cardiac repair, include but are not limited to bone marrow-derived cells, e.g., mesenchymal cells and stromal cells, smooth muscle cells, fibroblasts, SP cells, pluripotent cells or totipotent cells, e.g., teratoma cells, hematopoietic stem cells, for instance, cells from cord blood and isolated $CD34^+$ cells, multipotent adult progenitor cells, adult stem cells, embryonic stem cells, skeletal muscle derived cells, for instance, skeletal muscle cells and skeletal myoblasts, cardiac derived cells, myocytes, e.g., ventricular myocytes, atrial myocytes, SA nodal myocytes, AV nodal myocytes, and Purkinje cells. In one embodiment, the donor cells are autologous cells, however, non-autologous cells, e.g., xenogeneic cells, may be employed. The donor cells can be expanded in vitro to provide an expanded population of donor cells for administration to a recipient animal. In addition, donor cells may be treated in vitro as exemplified below. Sources of donor cells and methods of culturing those cells are known to the art.

Donor cells may also be treated in vitro by subjecting them to mechanical, electrical, or biological conditioning, or any combination thereof, as described in U.S. patent application Ser. No. 10/722,115, entitled "METHOD AND APPARATUS FOR CELL AND ELECTRICAL THERAPY OF LIVING TISSUE", which is incorporated by reference herein, conditioning which may include continuous or intermittent exposure to the exogenous stimuli. For instance, biological conditioning includes subjecting donor cells to exogenous agents, e.g., differentiation factors, growth factors, angiogenic proteins, survival factors, and cytokines, as well as to expression cassettes including transgenes encoding a gene product including, but not limited to, an angiogenic protein, a growth factor, a differentiation factor, a survival factor, or a cytokine, or comprising an antisense sequence, for instance, a ribozyme, or any combination thereof. Preferred exogenous agents include those which enhance the localization, differentiation, proliferation and/or function of donor cells after transplant. In one embodiment, the genetically modified (transgenic) donor cells include an expression cassette, the expression of which in donor cells enhances cellular proliferation, cellular localization, cellular differentiation and/or cellular function of the donor cells after implantation. The expression cassette optionally includes at least one control element such as a promoter, optionally a regulatable promoter, e.g., one which is inducible or repressible, an enhancer, or a transcription termination sequence. Preferably, the promoter and/or enhancer is one which is cell-or tissue-specific.

Transgenes useful in a variety of applications including cardiac therapies are disclosed in U.S. patent application Ser. No. 10/722,115, entitled "METHOD AND APPARATUS FOR CELL AND ELECTRICAL THERAPY OF LIVING TISSUE", and U.S. patent application Ser. No. 10/788,906, entitled "METHOD AND APPARATUS FOR DEVICE CONTROLLED GENE EXPRESSION", which are incorporated by reference herein. In one embodiment the expression of the transgene is controlled by a regulatable or tissue-specific promoter.

Optionally, a combination of vectors, each with a different transgene, can be delivered. Delivery of exogenous transgenes may be accomplished by any means, e.g., transfection with naked DNA, e.g., a vector comprising the transgene, liposomes, calcium-mediated transformation, electroporation, or transduction, e.g., using recombinant viruses, for instance, via adenovirus, adeno-associated virus, retrovirus or lentivirus vectors. A number of transfection techniques are generally known in the art. See, e.g., Graham et al., *Virology*, 52, 456 (1973), Sambrook et al., *Molecular Cloning: A Laboratory Manual*, Cold Spring Harbor Laboratories, New York (1989), Davis et al., *Basic Methods in Molecular Biology*, Elsevier (1986) and Chu et al., *Gene*, 13, 197 (1981). Particularly suitable transfection methods include calcium phosphate co-precipitation (Graham et al., *Virol.*, 52, 456 (1973)), direct microinjection into cultured cells (Capecchi, *Cell*, 22, 479 (1980)), electroporation (Shigekawa et al., *BioTechniques*, 6, 742 (1988)), liposome-mediated gene transfer (Mannino et al., *BioTechniques*, 6, 682 (1988)), lipid-mediated transduction (Felgner et al., *Proc. Natl. Acad. Sci. USA*, 84, 7413 (1987)), and nucleic acid delivery using high-velocity microprojectiles (Klein et al., *Nature*, 327, 70 (1987)). Preferred recombinant viruses to deliver exogenous transgenes to cells include recombinant lentiviruses, retroviruses, adenoviruses, adeno-associated viruses (AAV), and herpes viruses including cytomegalovirus.

Gene Therapy Vectors

Gene therapy vectors include, for example, viral vectors, liposomes and other lipid-containing complexes, and other macromolecular complexes capable of mediating delivery of a gene to a host cell. Open reading frames useful in gene therapy vectors include but are not limited to those described in U.S. patent application Ser. No. 10/788,906, entitled "METHOD AND APPARATUS FOR DEVICE CONTROLLED GENE EXPRESSION". Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Gene therapy vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene therapy vectors are described below. Gene therapy vectors may be administered via any route including, but not limited to, intramuscular, buccal, rectal, intravenous or intracoronary administration, and transfer to cells may be enhanced using electroporation and/or iontophoresis.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. Although lentiviruses have specific tropisms, pseudotyping the viral envelope with vesicular stomatitis virus yields virus with a broader range (Schnepp et al., *Meth. Mol. Med.*, 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing tissue specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al,. *Nat. Med.*, 8:864 (2002); Lynch et al., *Circ. Res.*, 80:197 (1997)).

Herpesvirus/Amplicon

Herpes simplex virus 1 (HSV-1) has a number of important characteristics that make it an important gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particulary useful for delivery of large genes.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature*, 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Synthetic Oligonucleotides

Antisense oligonucleotides are short (approximately 10 to 30 nucleotides in length), chemically synthesized DNA molecules that are designed to be complementary to the coding sequence of an RNA of interest. These agents may enter cells by diffusion or liposome-mediated transfer and possess relatively high transduction efficiency. These agents are useful to reduce or ablate the expression of a targeted gene while unmodified oligonucleotides have a short half-life in vivo, modified bases, sugars or phosphate groups can increase the half-life of oligonucleotide. For unmodified nucleotides, the efficacy of using such sequences is increased by linking the antisense segment with a specific promoter of interest, e.g., in an adenoviral construct. In one embodiment, electroporation and/or liposomes are employed to deliver plasmid vectors. Synthetic oligonucleotides may be delivered to cells as part of a macromolecular complex, e.g., a liposome, and delivery may be enhanced using techniques such as electroporation.

Targeted Vectors

The present invention contemplates the use of cell targeting not only by local delivery of the transgene or recombinant cell, but also by use of targeted vector constructs having features that tend to target gene delivery and/or gene expression to particular host cells or host cell types. Such targeted vector constructs would thus include targeted delivery vectors and/or targeted vectors, as described herein. Restricting delivery and/or expression can be beneficial as a means of further focusing the potential effects of gene therapy. The potential usefulness of further restricting delivery/expression depends in large part on the type of vector being used and the method and place of introduction of such vector. In addition, using vectors that do not result in transgene integration into a replicon of the host cell (such as adenovirus and numerous other vectors), cardiac myocytes are expected to exhibit relatively long transgene expression since the cells do not undergo rapid turnover. In contrast, expression in more rapidly dividing cells would tend to be decreased by cell division and turnover. However, other means of limiting delivery and/ or expression can also be employed, in addition to or in place of the illustrated delivery method, as described herein.

Targeted delivery vectors include, for example, vectors (such as viruses, non-viral protein-based vectors and lipid-based vectors) having surface components (such as a member of a ligand-receptor pair, the other half of which is found on a host cell to be targeted) or other features that mediate preferential binding and/or gene delivery to particular host cells or host cell types. As is known in the art, a number of vectors of both viral and non-viral origin have inherent properties facilitating such preferential binding and/or have been modified to effect preferential targeting (see, e.g., Miller, et al., *FASEB Journal*, 9:190 (1995); Chonn et al., *Curr. Opin. Biotech.*, 6:698 (1995); Schofield et al., *British Med. Bull.*, 51:56 (1995); Schreier, *Pharmaceutica Acta Helvetiae*, 68:145 (1994); Ledley, *Human Gene Therapy*, 6:1129 (1995); WO 95/34647; WO 95/28494; and WO 96/00295).

Targeted vectors include vectors (such as viruses, non-viral protein-based vectors and lipid-based vectors) in which delivery results in transgene expression that is relatively limited to particular host cells or host cell types. For example, transgenes can be operably linked to heterologous tissue-specific enhancers or promoters thereby restricting expression to cells in that particular tissue.

Seeding of Isolated ECM with Therapeutic Agents

Seeding of isolated ECM with agents including drugs, cytokines, cells and/or vectors can be performed prior to and/or at the time of implantation. In one embodiment, seeding of isolated ECM can be performed in a static two-dimensional chamber system or a three-dimensional rotating bioreactor. Wet matrix (2×3 cm in size) or tubular segments to be seeded are placed on the bottom of a chamber and covered with a liquid medium such as an aqueous medium, e.g., a cell culture medium, or perfused with such medium, for instance, over a period of up to 6 weeks in the presence of the one or more agents. Initially, for cell seeded ECM, approximately $1 \times 10^6$ cells may be added to isolated ECM. Additional cells may be added during subsequent culture. Cells may attach directly to isolated ECM via several attachment proteins present within the ECM, including type I collagen, type IV collagen, and fibronectin (Hodde et al., *Tissue Engineering*, 8:225 (2002)). Cells may grow to single-layer confluence on both surfaces of isolated ECM sheets, and endothelial cells can penetrate the ECM if they are seeded on the abluminal side of the ECM sheets (Hodde et al., *Tissue Engineering*, 8:225 (2002)).

Compositions, Dosages and Routes of Administration

The amount of agent administered, including cells, gene therapy vectors, one or more cytokines and/or other drugs which are exogenously administered, either in agent seeded isolated ECM or separately, will vary depending on various factors. The agents of the invention may be employed in conjunction with other therapies, e.g., therapies for ischemia or arrhythmias, including other gene therapies and/or cell therapies, e.g., see U.S. patent application Ser. No. 10/723,258, filed on Nov. 25, 2003, entitled "METHOD AND APPARATUS FOR CELL AND ELECTRICAL THERAPY OF LIVING CELLS" and U.S. patent application Ser. No. 10/788,906, filed on Feb. 27, 2004, entitled "METHOD AND APPRATUS FOR DEVICE CONTROLLED GENE EXPRESSION", the disclosures of which are incorporated herein by reference in their entirety.

Administration of the agents in accordance with the present invention may be continuous or intermittent, depending, for example, upon the recipient's physiological condition, whether the purpose of the administration is therapeutic or prophylactic, and other factors known to skilled practitioners. The administration of the agents of the invention which are not incorporated into isolated ECM may be essentially continuous over a preselected period of time or may be in a series of spaced doses. Both local and systemic administration is contemplated.

One or more suitable unit dosage forms comprising the agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes.

The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

Pharmaceutical formulations containing the agents of the invention can be prepared by procedures known in the art using well known and readily available ingredients. For example, the agent can be formulated with common excipients, diluents, or carriers. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols. The formulations can include buffering agents such as calcium carbonate, magnesium oxide and magnesium carbonate, as well as, inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and gelatin, microcrystalline cellulose, sodium lauryl sulfate, starch, talc, or titanium dioxide, or liquid vehicles such as polyethylene glycols (PEGs) and vegetable oil.

The pharmaceutical formulations of the agents of the invention can also take the form of an aqueous or anhydrous solution or dispersion, or alternatively the form of an emulsion or suspension.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

Additionally, the agents are well suited to formulation as sustained release dosage forms and the like. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., a stent, epicardial patch, lead, and the like.

The formulations and compositions described herein may also contain other ingredients such as antimicrobial agents, or preservatives. Furthermore, as described herein the active ingredients may also be used in combination with other therapeutic agents or therapies.

Donor cells may be administered pericardially, epicardially, intramyocardially, intravenously, transvenously, or by any other convenient route, and delivered, for instance, by a lead, needle, catheter, e.g., a catheter which includes an injection needle or infusion port, or other suitable device. Cells to be administered may be a population of individual cells or cells grown in culture so as to form a two dimensional or three dimensional structure. The number of cells to be administered will be an amount which results in a beneficial effect to the recipient. For example, from $10^2$ to $10^{10}$, e.g., from $10^3$ to $10^9$, $10^4$ to $10^8$, or $10^5$ to $10^7$, cells can be administered. Agents which may enhance cellular function or stimulate angiogenesis include but are not limited to pyruvate, catecholamine stimulating agents, fibroblast growth factor, e.g., basic fibroblast growth factor, acidic fibroblast growth factor, fibroblast growth factor-4 and fibroblast growth factor-5, epidermal growth factor, platelet-derived growth factor, vascular endothelial growth factor (e.g., $VEGF_{121}$, $VEGF_{145}$, $VEGF_{165}$, $VEGF_{189}$ or $VEGF_{206}$), tissue growth factors and the like, which may optionally be present in a composition comprising the donor cells or administered separately.

Generally any route of administration may be employed for non-cell based gene therapy vectors, including oral, mucosal, intramuscular, buccal and rectal administration. For certain vectors, certain routes of administration may be preferred. Several techniques have been developed for cardiac gene delivery, including pericardial infusion, endomyocarial injection, intracoronary injection, coronary venous retroperfusion, and aortic root injection (Isner, *Nature,* 415:234 (2002)). The different techniques achieve variable response in homogeneity of gene delivery, resulting in focal gene expression within the heart (Hajjar et al., *Circ. Res.,* 86:616 (2000). For this reason, techniques that achieve diffuse uptake would seem to be superior. Two such methods utilize the heart's arterial and venous circulation to accomplish disseminated viral transfection. Arterial injection, performed directly through a percutaneous approach or indirectly by an infusion into the cross-clamped aorta, has shown promise in animal models of heart failure and is appealing in that it can be performed either at the time of cardiac surgery or as percutaneous intervention (Hajjar et al., *PNAS USA,* 95:5251 (1998)). Similarly, retroperfusion through the coronary sinus appears to produce a more global gene expression in comparison with techniques of localized or focal injection (Boeckstegers et al., *Circ.,* 100:1 (1999)).

Direct myocardial injection of plasmid DNA as well as virus vectors, e.g., adenoviral vectors, and cells including recombinant cells has been documented in a number of in vivo studies. This technique when employed with plasmid DNA or adenoviral vectors has been shown to result in effective transduction of cardiac myocytes. Thus, direct injection may be employed as an adjunct therapy in patients undergoing open-heart surgery or as a stand-alone procedure via a modified thorascope through a small incision. In one embodiment, this mode of administration is used to deliver a gene or gene product that would only require limited transfection efficiency to produce a significant therapeutic response, such as a gene that encodes for or leads to a secreted product (e.g., VEGF, endothelial nitric oxide synthase). Virus, e.g., pseudotyped, or DNA- or virus-liposome complexes may be delivered intramyocardially.

Intracoronary delivery of genetic material can result in transduction of approximately 30 % of the myocytes predominantly in the distribution of the coronary artery. Parameters influencing the delivery of vectors via intracoronary perfusion and enhancing the proportion of myocardium transduced include a high coronary flow rate, longer exposure time, vector concentration, and temperature. Gene delivery to a substantially greater percent of the myocardium may be enhanced by administering the gene in a low-calcium, high-serotonin mixture (Donahue et al., *Nat. Med.,* 6:1395 (2000)). The potential use of this approach for gene therapy for heart failure may be increased by the use of specific proteins that enhance myocardial uptake of vectors (e.g., cardiac troponin T).

Improved methods of catheter-based gene delivery have been able to achieve almost complete transfection of the myocardium in vivo. Hajjar et al. (*Proc. Natl. Acad. Sci. USA,* 95:5251 (1998)) used a technique combining surgical catheter insertion through the left ventricular apex and across the aortic valve with perfusion of the gene of interest during cross-clamping of the aorta and pulmonary artery. This technique resulted in almost complete transduction of the heart and could serve as a protocol for the delivery of adjunctive gene therapy during open-heart surgery when the aorta can be cross-clamped.

Gene delivery can be performed by incorporating a gene delivery device or lumen into a lead such as a pacing lead, defibrillation lead, or pacing-defibrillation lead. An endocardial lead including a gene delivery device or lumen allows endocardial gene delivery. An epicardial lead including a gene delivery device or lumen allows epicardial gene delivery. A transvenous lead including a gene delivery device or lumen may also allow intravenous gene delivery. Lead-based delivery is particularly advantageous when the lead is used to deliver electrical and gene therapies to the same region.

Gene delivery to the ventricular myocardium by injection of genetic material into the pericardium has shown efficient gene delivery to the epicardial layers of the myocardium. However, hyaluronidase and collagenase may enhance transduction without any detrimental effects on ventricular function. Recombinant cells may also be delivered pericardially.

Vectors of the invention may conveniently be provided in the form of formulations suitable for administration, e.g., into the blood stream (e.g., in an intracoronary artery). A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. Vectors of the present invention should preferably be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions can also be prepared to enhance shelf life and stability. Therapeutically useful compositions of the invention can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors can be provided in a dosage form containing an amount of a vector effective in one or multiple doses. For viral vectors, the effective dose may be in the range of at least about $10^7$ viral particles, preferably about $10^9$ viral particles, and more preferably about $10^{11}$ viral particles. The number of viral particles may, but preferably does not exceed $10^{14}$. As noted, the exact dose to be administered is determined by the attending clinician, but is preferably in 1 ml phosphate buffered saline. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered.

By way of illustration, liposomes and other lipid-containing gene delivery complexes can be used to deliver one or more transgenes. The principles of the preparation and use of such complexes for gene delivery have been described in the art (see, e.g., Ledley, *Human Gene Therapy*, 6:1129 (1995); Miller et al., *FASEB Journal*, 9:190 (1995); Chonn et al., *Curr. Opin. Biotech.*, 6:698 (1995); Schofield et al., *British Med. Bull.*, 51:56 (1995); Brigham et al., *J. Liposome Res.*, 3:31 (1993)).

One or more suitable unit dosage forms comprising the gene therapy vector, which may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

Pharmaceutical formulations containing the gene therapy vector can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions for convenient oral administration or as solutions appropriate for parenteral administration, for instance by intramuscular, subcutaneous or intravenous routes.

The pharmaceutical formulations of the vectors can also take the form of an aqueous or anhydrous solution or dispersion, or alternatively the form of an emulsion or suspension.

Thus, the vector may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

For administration to the upper (nasal) or lower respiratory tract by inhalation, the vector is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the vector and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the vector may be administered via nose drops, a liquid spray, such as via a plastic bottle atomizer or metered-dose inhaler. Typical of atomizers are the Mistometer (Wintrop) and the Medihaler (Riker).

The local delivery of the vectors can also be by a variety of techniques which administer the vector at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the vectors may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The vector may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents or preservatives.

Devices Having Isolated ECM

In accordance with the present invention, isolated ECM is used advantageously to decrease undesirable sequelae at the site of device implantation in a warm blooded vertebrate. A solid sheet, strip or loop of isolated ECM, or fluidized or powder forms of isolated ECM, may be applied to and/or fixed to a device. A sheet of isolated ECM can be applied to (contacted with) or adhered to (fixed to) an implantable device. Particulate isolated ECM may be coated on an implantable device, and/or a gel form of ECM may be applied to an implantable device and subsequently lyophilized to form a coating. In one embodiment, ECM in sheet form can be used to form coated implantable devices. Isolated ECM may be applied to or affixed to a device or to other isolated ECM materials, other bioscaffolds or other materials with anchoring projections (such as plastic or metal pins or sutures), adhesives, or other fixation devices known to those skilled in the art. In one embodiment, an isolated ECM sheet is sutured or otherwise secured to a device. For example, isolated ECM may be wrapped around the device and redundant tissue gathered and secured via sutures. Tissue segments or sheets can be attached to each other before or during attachment to a device using surgically acceptable techniques, e.g., suturing, gluing, stapling or compressing. Multilaminate constructs may be formed by overlapping individual strips of isolated ECM and applying pressure to the overlapped portions to fuse the strips together. In one embodiment, pressure is applied to the overlapped strips under conditions allowing dehydration of the isolated ECM.

Example of Isolated ECM Based Therapy

The present teachings are useful in a number of therapies. In one example, the treatment of a failing heart is possible. Such therapies may be employed for both ischemic and non-ischemic heart failure etiologies.

In one approach, isolated ECM incorporating donor cells, cytokine(s), and/or gene therapy vectors is applied to a tissue and electrical therapy is delivered to that tissue, optionally in conjunction with a drug or other agent administration while in other approaches isolated ECM is applied to a tissue and electrical therapy is delivered to that tissue, optionally in conjunction with separate delivery of an agent such as a drug, donor cell, cytokine(s), and/or gene therapy vector(s). In one approach, donor cell, cytokine(s) and/or gene therapy is administered prior to introduction of isolated ECM and the initiation of electrical therapy. Moreover, it is understood that multiple donor cell, cytokine(s), and/or gene therapies may be implemented prior to and/or after applying isolated ECM and/or delivering electrical therapy to an identified tissue region. Also, for example, donor cell, cytokine, and/or gene therapy may be followed by multiple electrical therapies. It is understood that different permutations of drug, donor cell, cytokine, and/or gene therapy, isolated ECM therapy and electrical therapy may be performed in varying embodiments. For instance, electrical therapy may be applied before, during, or after exogenous agent therapy. In one approach, cellular localization, proliferation, differentiation, and/or function, e.g., contractile function, of donor cells or endogenous stem cells in the recipient is enhanced by the electrical stimulus from the electrical therapy.

In one embodiment an advanced patient management system is used to control the applied electrical therapy in conjunction with inputs regarding other therapies such as drug, cell, cytokine, and/or gene therapies, inputs regarding patient health, and inputs regarding environmental conditions. Other inputs are contemplated, and those provided herein are intended to demonstrate the flexibility and programmability afforded the user when the cell and electrical therapies are managed with an advanced patient management system. Such a system is discussed in various applications by the assignee, including, but not limited to, in U.S. patent application Ser. No. 10/093,353, filed Mar. 6, 2002 and U.S. patent application Ser. No. 10/323,604, filed Dec. 18, 2002, which are hereby incorporated by reference in their entirety.

FIG. 1 is a flow diagram showing a particular therapy for treating cardiac tissue using combined isolated ECM and electrical therapies according to one embodiment of the present invention. The cardiac tissue region (or regions) of damaged tissue are identified at 130 and then isolated ECM therapy is applied to one or more areas of damaged tissue at 140. Pacing therapy is applied to the identified cardiac tissue region at 150. Tissue damage resulting from a myocardial infarction or heart attack is one type of tissue treatable by these apparatus and methods.

Different methods of locating the damaged tissue may be employed. For example, electrophysiology, such as electrocardiograms, can be used to locate damaged cardiac tissue. Other locating methods include, but are not limited to: echocardiography and catheter-based voltage mapping of a portion of the heart; catheter based strain mapping; invasive or minimally invasive surgery (visualization of damaged tissue); and other imaging techniques, such as MRI, perfusion imaging, fluoroscopy, and angiography.

Once the damaged tissue is located, the localized area may be treated by applying isolated ECM. In one embodiment, the isolated ECM is contacted with donor cells, one or more cytokines and/or one or more gene therapy vectors prior to or at the time of implantation. Combined isolated ECM and electrical therapy may also be accompanied by the administration of drugs.

In the example of cardiac tissue, electric current is imposed across or adjacent to the damaged tissue. In one embodiment a pacemaker with implanted catheter leads is employed to provide the appropriate pacing stimulation to the identified region of tissue. In varying embodiments, one or more electrodes serve to apply an electric field over portions of the identified tissue region. In implanted pacemaker applications the pacemaker housing may serve as an electrode.

In one embodiment, the pacemaker is programmed to perform VDD pacing using an atrioventricular delay which is relatively short when compared to the intrinsic atrioventricular interval. In such embodiments, the electrical pace wavefront is near the infarcted region very early in the cardiac cycle so as to electrophysiologically capture and mechanically unload the identified region with the pacing stimulus. The VDD mode of the pacemaker allows the heart to maintain a rate at a normal sinus rhythm, providing better control of the activation pattern; the ventricles are pre-excited without advancing the pacing rate unnecessarily. In this way, the depolarization wavefront fuses with the paced complex, resulting in the most intrinsic activation of the ventricles, yet providing for the pre-excitement of the damaged tissue region. In another embodiment, the pacemaker is programmed to perform DDD pacing using an atrioventricular delay which is relatively short when compared to the intrinsic atrioventricular interval (measured when at least the ventricular beat is intrinsic). The DDD mode of the pacemaker forces the heart to beat in a normal or desired rate when the heart fails to maintain normal sinus rhythm. The VDD and DDD modes each includes a biventricular version where both the right ventricle (RV) and the left ventricle (LV) are paced. The RV and LV are paced using same or different atrioventricular pacing delays and a controllable interventricular (RV to LV) pacing delay. Other pacing modes are possible, and those provided here are not intended in an exhaustive or exclusive sense.

In varying embodiments and combinations, the electrical therapy includes different programming modes for use with a particular therapy. In one embodiment, electrical therapy is invoked during periods of relative inactivity such as are common during nocturnal sleep to condition the cardiac tissue and improve cell localization to cardiac tissue. In one embodiment, electrical therapy is invoked based on physical activity of the patient during which heart wall stress is reduced via electrical pre-excitation. Such physical activity may be measured by detection of accelerometer or minute ventilation sensor data. In one embodiment, the electrical therapy is invoked for certain times of day or during specifically programmed, recurring patterns of intrinsic (M beats) and paced beats (N beats) in a ratio of M:N. In embodiments featuring programmable microprocessors, the time of day is downloaded to the microprocessor upon programming and therapy is programmably selectable. In varying embodiments and combinations, electrical therapy is delivered upon preselected sensor inputs. For example, electrical therapy is invoked (continuous or M:N patterns) upon detected patient activity. In one embodiment, electrical therapy is invoked upon detection of patient stress. In one embodiment, electrical therapy is invoked upon detection of patient metabolic low stress in the heart, such as in sleep, where ventricles are distended and filling better. In one embodiment internal pressure is measured to determine local stress. Different sensors may be employed to determine conditions for delivery of electrical therapy.

Additional programming modes are contemplated by the present description. For example, in one embodiment a variable programming mode incorporates traditional electrical pacing interspersed with specialized cell therapy pacing cycles. In one embodiment, such pacing is used to provide complementary pacing therapies to a patient's heart to provide multiple benefits. In one embodiment, the varying pacing is applied using a duty-cycle approach. For example, a ratio of pacing of a first type to a pacing of a second type is programmed into the implantable device to provide a plurality of pacing therapies to a patient. This provides a new pacing mode where the programmability of duty cycle affords electrical therapy that complements at least one other pacing therapy such as cardiac resynchronization therapy and optionally other therapies such as cell therapy.

Another pacing variation provides a dynamically changing atrioventricular delay. In one exemplary embodiment, an atrioventricular delay is increased over a predetermined time period. For one example, an atrioventricular delay is lengthened by approximately one (1) millisecond each day over a predetermined time, such as three (3) months. In one embodiment, the atrioventricular delay is lengthened by 10 milliseconds over a predetermined amount of time, such as 2 months. In such embodiments, incremental increase in atrioventricular delay results in progressively loading a cardiac region, based on location of the electrodes. Similar but opposite effects might be obtained by progressively shortening the atrioventricular delay. Certain areas of the myocardium might be progressively unloaded, resulting in desired phenotypical changes at the chamber, tissue and cell levels.

Other embodiments and combinations are possible without departing from the scope of the present therapy system. The foregoing examples are intended to demonstrate some varying embodiments of the present therapy system, and are not intended in an exclusive or exhaustive sense.

In one embodiment, the pacing lead is positioned as close as possible to the site of engraftment. Positioning is performed using electrophysiology (e.g., ECG), echocardiographic mapping, or catheter based voltage mapping of the heart. Other location methods are possible without departing from the scope of the present teachings.

Lead placement is possible using epicardial leads implanted with minimal thoracotomy, and/or endocardial leads. Treatment of the left ventricular region is possible using leads positioned in the coronary venous structures.

It is understood that a plurality of infarcted tissue regions may be treated using multiple cell and electrical therapy treatments.

Example Cardiac Function Management Device

Figure 2:
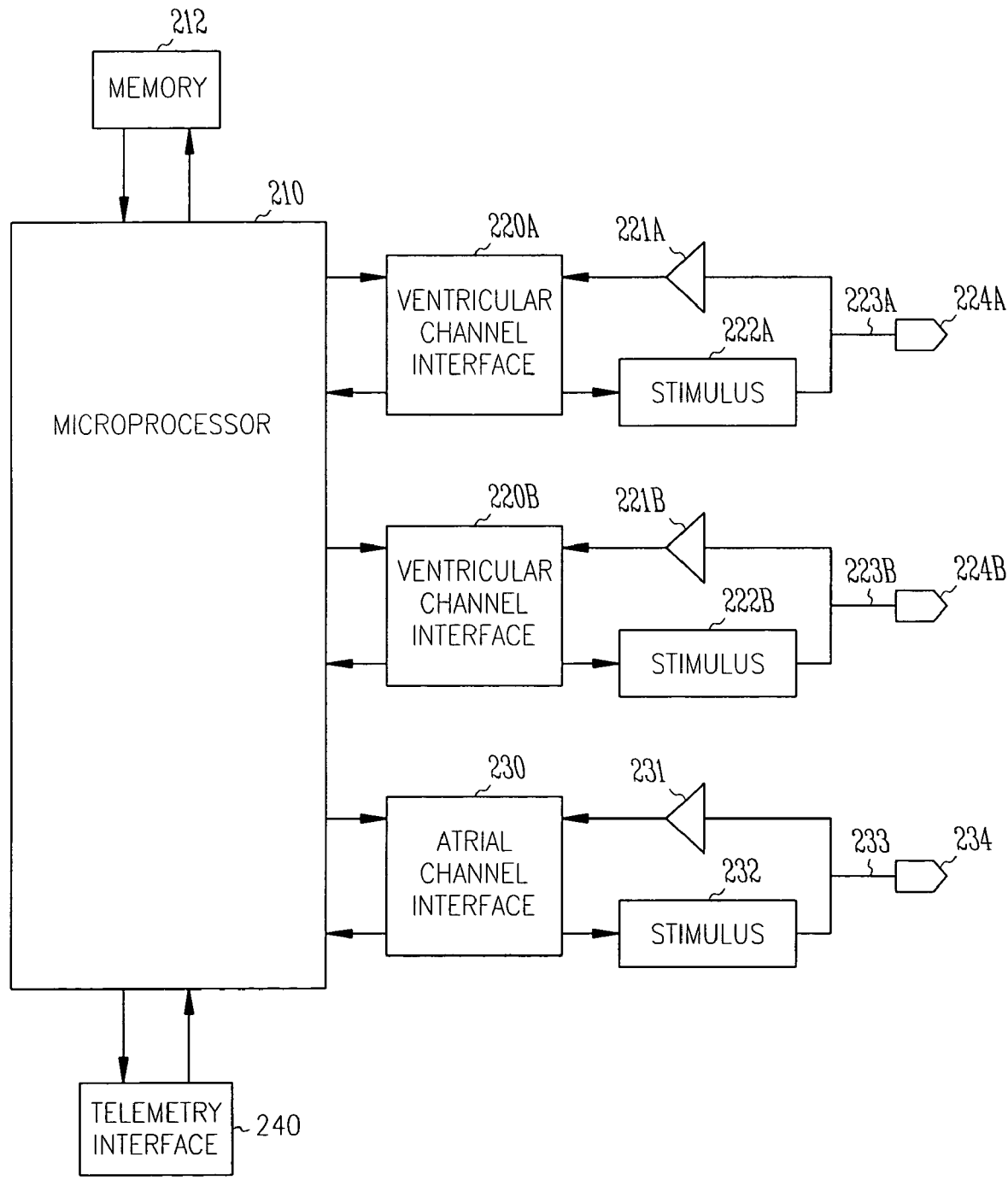
FIG. 2 shows a block diagram of pacemaker for electrical therapy according to one embodiment of the present invention.

FIG. 2 shows a pacemaker performing the electrical therapy described herein. As used herein, the term pacemaker should be taken to mean any cardiac rhythm management (CRM) device for pacing the heart and includes implantable pacemakers, external pacemakers, and implantable cardiac defibrillator/converters having a pacing functionality. A block diagram of a cardiac pacemaker having two ventricular pacing channels is shown in FIG. 2. Microprocessor 210 communicates with a memory 212 via a bidirectional data bus. In varying embodiments memory 212 comprises a ROM or RAM for program storage and a RAM for data storage. In one embodiment, the control unit includes dedicated circuitry either instead of, or in addition to, the programmed microprocessor for controlling the operation of the device. In one embodiment, the pacemaker employs a programmable microprocessor to implement the logic and timing functions for operating the pacemaker in accordance with a specified pacing mode and pacing parameters as well as for performing the data acquisition functions. A telemetry interface 240 is also provided for communicating with an external programmer. Such an external programmer may be used to change the pacing mode, adjust operating parameters, receive data stored by the device, and issue commands that affect the operation of the pacemaker. Such an interface also provides communications with advanced patient management devices, such as portable computers, PDA's, and other wireless devices as described herein and provided by the documents incorporated herein.

In embodiments incorporating physical motion detection for application of therapy the pacemaker includes sensors to detect exercise. For example, accelerometers and minute ventilation sensors may be incorporated for these purposes. Some embodiments may incorporate time of day for application of therapy. Such embodiments may include timing modules and may update them using information from a programmer or other wireless device.

The pacemaker has atrial sensing/stimulation channels comprising electrode 234, lead 233, sensing amplifier/filter 231, pulse generator 232, and an atrial channel interface 230 which communicates bidirectionally with a port of microprocessor 210. The device also has two ventricular sensing/stimulation channels that include electrodes 224A-B, leads 223A-B, sensing amplifiers 221A-B, pulse generators 222A-B, and ventricular channel interfaces 320A-B where "A" designates one ventricular channel and "B" designates the other. For each channel, the same lead and electrode are used for both sensing (i.e., detecting P-waves and R-waves) and stimulation. The ventricular electrodes could be disposed in each of the ventricles for biventricular pacing or in only one ventricle for multi-site pacing of that ventricle. The channel interfaces 220A-B and 230 include analog-to-digital converters for digitizing sensing signal inputs from the sensing amplifiers and registers which can be written to by the microprocessor in order to output stimulation pulses, change the stimulation pulse amplitude, and adjust the gain and threshold values for the sensing amplifiers. After digitization of the sensed signals by the channel interfaces, the signal samples can be processed in the digital domain by algorithms executed by the microprocessor in order perform further filtering. The detection of R wave and P wave peaks for timing purposes can also be performed digitally. Alternatively, a standard peak detection circuit could be used.

In one embodiment, the lead system includes endocardial leads, although other types of leads, such as epicardial leads, could also be used within the scope of the present teachings. In one embodiment, a first ventricular lead system is adapted for placement in a first cardiac region of the heart. In one example, the first cardiac region of the heart is within the coronary sinus and/or the great cardiac vein of the heart adjacent to the left ventricle. In one embodiment, the first lead system includes a number of electrodes and electrical contacts. A tip electrode is located at, or near, the distal end of the first lead system, and connects electrically to terminal through a conductor provided within the first lead system. The first lead system also includes a proximal electrode which is spaced proximal the tip electrode. In one embodiment, the proximal electrode is spaced proximal the tip electrode for placement adjacent to the left ventricle of the heart. The proximal electrode is electrically connected to terminal through an internal conductor within the first lead system. The proximal electrode can be of either an annular or a semi-annular construction, encircling or semi-encircling the peripheral surface of the first lead system.

The pacemaker further includes a second ventricular lead system. In one embodiment, the second lead system is an endocardial lead, although other types of leads, such as epicardial leads, could be used within the scope of the present teachings. The second ventricular lead system is adapted for placement within a second cardiac region of the heart. In one example, the second cardiac region of the heart is the right ventricle of the heart. In one embodiment, the second lead system includes a number of electrodes and electrical contacts. For example, in one embodiment, a tip electrode is located at, or near, the distal end of the second lead system, and connects electrically through a conductor provided in the lead, for connection to terminal. The second lead system further optionally includes a first defibrillation coil electrode spaced proximal to the distal end for placement in the right ventricle. The first defibrillation coil electrode is electrically connected to both terminals and through internal conductors within the body of the second lead system. The second lead system also optionally includes a second defibrillation coil electrode, which is spaced apart and proximal from the distal end of the second lead system such that the second defibrillation coil electrode is positioned within the right atrium or major vein leading to the right atrium of the heart. The second defibrillation coil electrode is electrically connected to terminal through an internal conductor within the body of the second lead system.

In varying embodiments, the first and second system each include one, two, or more electrodes. In varying embodiments, the system includes multiple atrial electrodes and optionally includes the defibrillation components. The configuration and placement of electrodes may vary without departing from the scope of the present teachings.

In one embodiment, the pacemaker is a programmable microprocessor-based system, with a microprocessor and memory, which contains parameters for various pacing and sensing modes. Pacing modes include, but are not limited to, normal pacing, overdrive or burst pacing, and pacing for prevention of ventricular tachyarrhythmias. The system also includes means for adjusting atrioventricular delay. The microprocessor further includes means for communicating with an internal controller, in the form of an RF receiver/transmitter. This includes an antenna, whereby it may receive and transmit signals to and from an external controller. In this manner, programming commands or instructions can be transferred to the microprocessor after implant. In one embodiment operating data is stored in memory during operation. This data may be transferred to the external controller for medical analysis.

In one embodiment, pacing pulses are controlled by the microprocessor to carry out a coordinated pacing scheme at the two ventricular pacing locations. Pacing modes include, but are not limited to, normal sinus rhythm pacing modes, overdrive or burst pacing modes for treating ventricular tachyarrhythmia, pacing regimens for preventing the onset of a ventricular tachyarrhythmia, cardiac resynchronization therapy and/or cardiac remodeling control therapy. Additional advantages for providing pacing from the two ventricular pacing locations include the ability for either one of the two pacing systems to serve as a back-up pacing system and location for the other in the event that one pacing system were to fail.

Atrial sensing circuit is coupled by an atrial lead to a heart for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. An atrial sensing circuit provides one or more signals to controller to indicate, among other things, the presence of sensed intrinsic atrial heart contractions.

An atrial therapy circuit provides atrial pacing therapy, as appropriate, to electrodes located at or near one of the atria of the heart for obtaining resulting evoked atrial depolarizations. In one embodiment, the atrial therapy circuit also provides cardioversion/defibrillation therapy, as appropriate, to electrodes located at or near one of the atria of the heart, for terminating atrial fibrillation and/or other atrial tachyarrhythmias.

Although FIG. 2 shows an implanted CRM device, it is understood that the teachings may be used with devices other than CRM devices. The teachings are also applicable to non-mammalian heart therapies. Those skilled in the art, upon reading and understanding the present description, shall appreciate other uses and variations within the scope of the present teachings.

Figure 3:
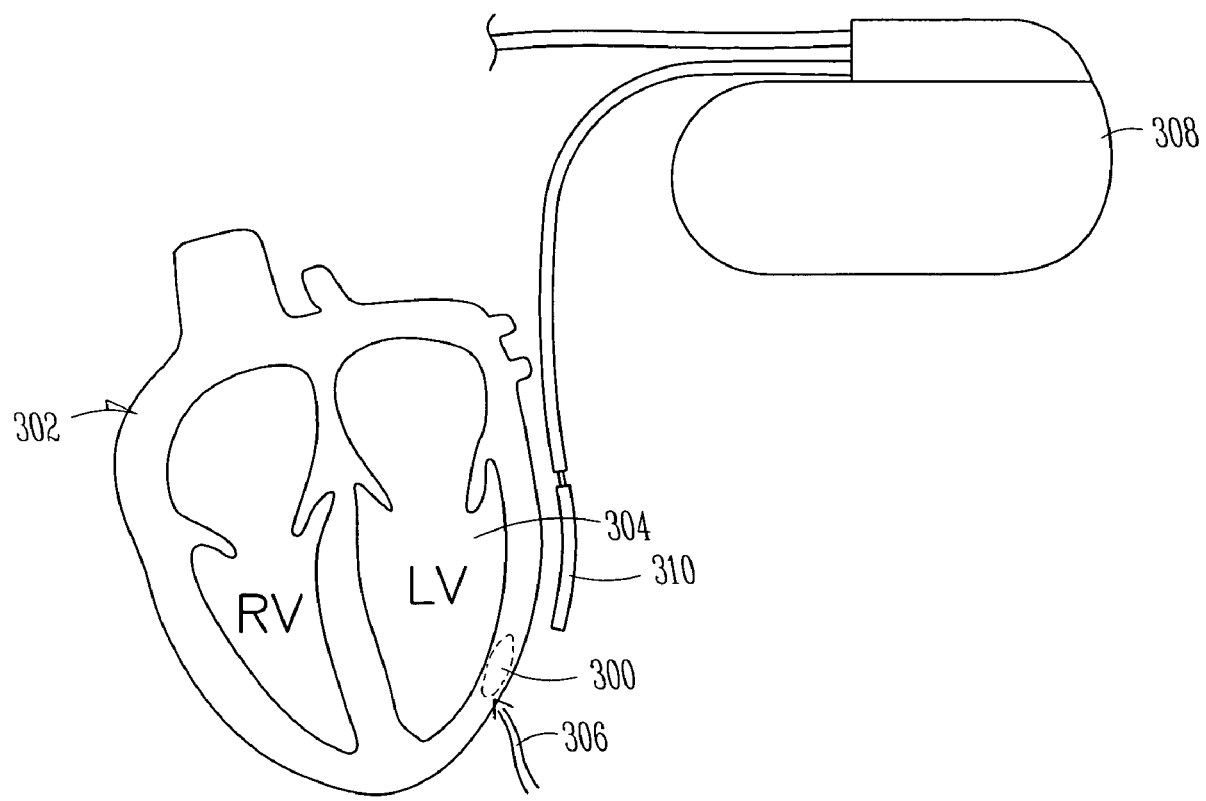
FIG. 3 shows a block diagram of one example of isolated ECM, exogenous cell and electrical therapies.

FIG. 3 shows one example of administration of isolated ECM seeded with exogenous cells and electrical therapy to a region of cardiac tissue subject to myocardial infarction. The heart 302 includes a left ventricle 304 which has tissue injured by a myocardial infarction in an affected region 300. Affected region 300 is determined by methods including those described herein. Isolated ECM 306 is preferably administered in close proximity to adjacent non-infarcted tissue and/or directly to the affected region 300 and electrical therapy is applied using a programmable pulse generator 308 and lead 310.

The electrical therapy includes pacing in vivo preferably near infarcted or hibernating myocardium and including sites targeted for isolated ECM therapy, which enhances the localization, proliferation, and/or function, and optionally the differentiation, of cells at the site(s). The pacing may be applied to lessen local stress and strain that might otherwise inhibit the successful localization of cells including the successful formation of gap junctions between cells and noninfarcted recipient myocardial cells. Such therapy thus affects both mechanical and electrical connections to neighboring cells of the native myocardium. In particular, pacing at or near such sites may enhance development of new gap junctions which may be needed for coordinating the function of the donor cells with that of the native myocardium. The therapy also operates to control metabolic demands at the site of therapy to increase the viability of cells migrating to the ECM. Another benefit is that electrical stimulation of myocytes promotes release of factors that encourage angiogenesis. In one embodiment, electrical therapy improves the local environment in damaged cardiac tissue, e.g., by improving pump efficiency, oxygen consumption, and/or mechanical synchrony, decreasing metabolic load and/or stress, and/or reorienting stress-strain patterns. In one embodiment, preconditioning of donor cells cultured in vitro, e.g., contacted with drugs or other chemical agents, gene therapy vectors, and/or subjected to electrical stimulation and/or mechanical stimulation, may benefit in vivo localization, proliferation, differentiation and/or functioning of the donor cells.

In vivo left ventricle pacing controls local stress by managing atrioventricular delay, RV-LV offset (e.g., applying an interventricular delay between RV and LV pacing pulse deliveries, or two independent atrioventricular delays for RV and LV pacing pulse deliveries), stimulation site alternation, heart rate, and pacing waveform parameters. The LV stimulus may also promote cell localization, proliferation, differentiation and/or functioning in vivo and is controllable based on pacing waveform, rate, and site.

In one embodiment, the pacemaker is programmed to perform VDD pacing using an atrioventricular delay which is relatively short when compared to the intrinsic atrioventricular interval. In another embodiment, the pacemaker is programmed to perform DDD pacing using an atrioventricular delay which is relatively short when compared to the intrinsic atrioventricular interval (measured when at least the ventricular beat is intrinsic). Other electrical therapies are possible given the teachings herein. For example, it is possible that the affected region is pre-treated to strengthen the region before other therapies. Upon reading and understanding the teachings provided herein, those skilled in the art will understand other electrical therapies are possible without departing from the scope of the present teachings.

Figure 4A:
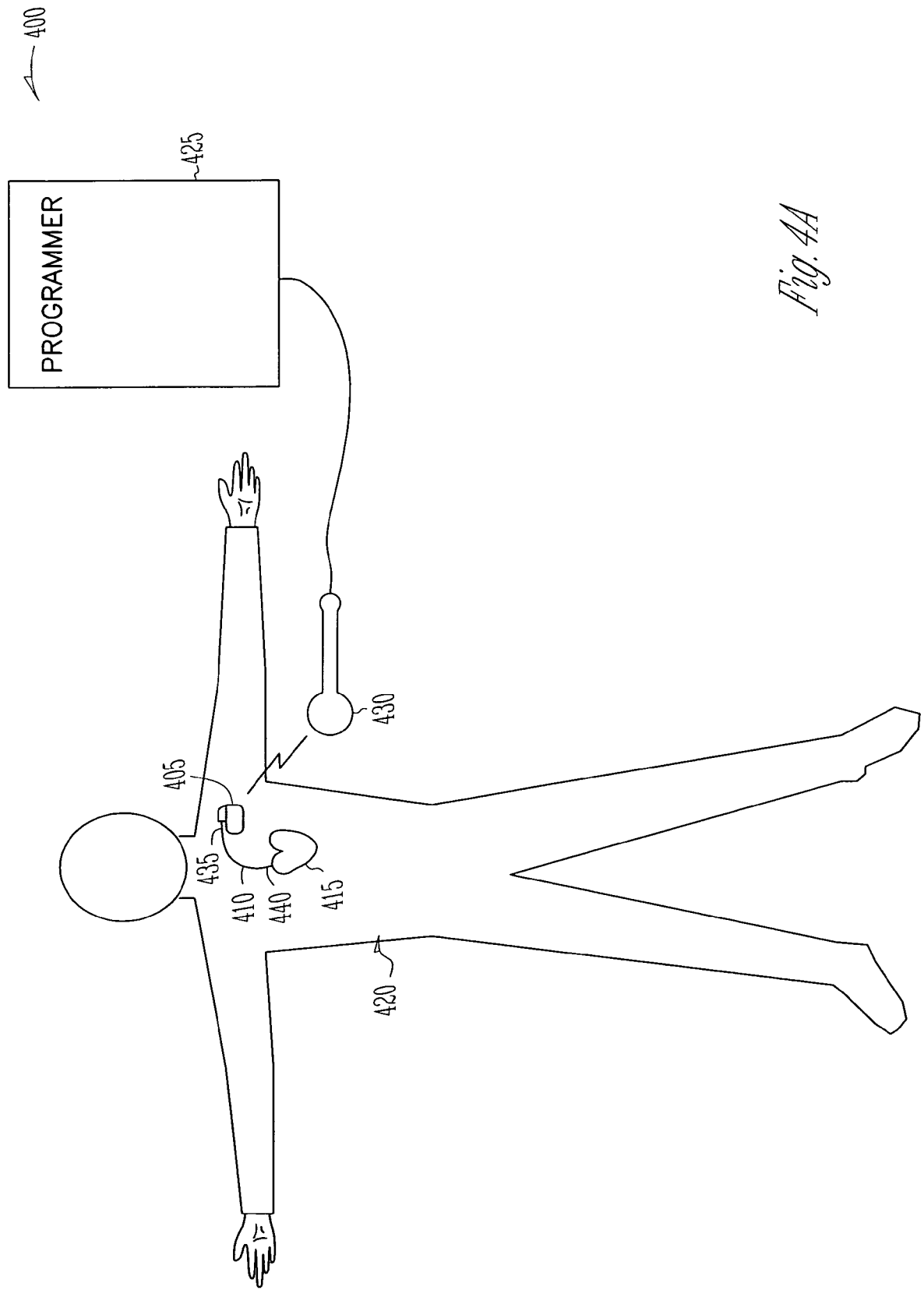
FIG. 4A is a diagram showing a programmer for use with an implanted CRM system according to one embodiment of the present invention.

FIG. 4A is a schematic drawing illustrating, by way of example, but not by way of limitation, one embodiment of portions of a CRM system 400 and an environment in which it is used. System 400 includes an implantable CRM device 405, also referred to as an electronics unit, which is coupled by an intravascular endocardial lead 410, or other lead, to a heart 415 of patient 420. Implantable CRM device 405 includes a pacemaker. System 400 also includes an external programmer 425 providing wireless communication with implantable CRM device 405 using a telemetry device 430. Lead 410 includes a proximal end 435, which is coupled to implantable CRM device 405, and a distal end 440, which is coupled to one or more portions of heart 415. Although FIG. 4A shows a human with an implanted CRM device, it is understood that the teachings may be used with devices other than CRM devices. The teachings are also applicable to non-mammalian heart therapies. Those skilled in the art, upon reading and understanding the present description, shall appreciate other uses and variations within the scope of the present teachings.

Figure 4C:
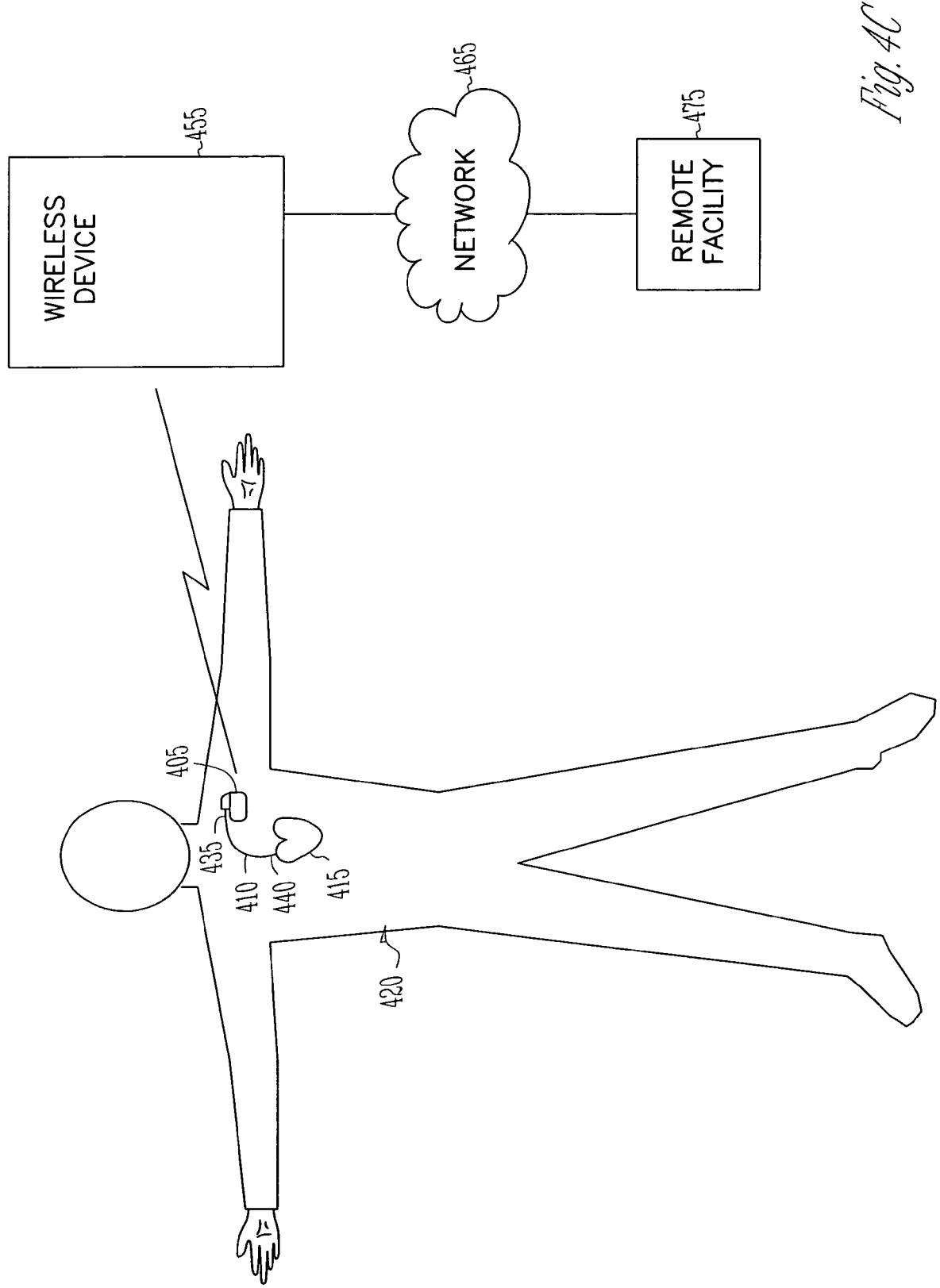
FIG. 4C is a diagram showing a wireless device in communication with an implanted device and connected to a network for communication with a remote facility for management of the implanted device and therapy according to one embodiment of the present invention.

FIG. 4B is a diagram showing a wireless device in communications with an implanted device for management of the implanted device and therapy according to one embodiment of the present invention. In one embodiment, wireless device 455 is used to conduct communications with implantable CRM device 405. In one application, wireless device 455 is a personal digital assistant (PDA). In one embodiment, wireless device 455 is a computer with wireless interface. In one embodiment, wireless device 455 is a cellular phone. The communications between implantable CRM device 405 and wireless device 455 can be used for coordinating operations and therapies of the pacemaker and/or to communicate device operations and physiological data to another site in communications with the wireless device 455. FIG. 4C shows one example of communications where a network 465 is in contact with wireless device 455. The connection between wireless device 455 and network 465 can be either wired or wireless. In one embodiment, network 465 is the Internet. Remote facility 475 is a medical facility or location which a doctor or health care provider can access data from implantable CRM device 405. Alternatively, data and/or instructions can be transmitted from the remote facility 475 to the wireless device 455 and/or the implantable CRM device 405. Alternatively, instructions and data can be transferred bidirectionally between the remote wireless device, and/or implantable CRM device 405.

The network is a communication system that interconnects a number of computer processing units when those units are some distance away from one another, but within the same contiguous property to allow private communications facilities to be installed. The network may also include the facility to allow multiple compute processors to communicate with each other when some or all of those processors are within the same enclosure and connected by a common back plane.

Connections with a remote facility and wireless device are useful for advanced patient management. Some exemplary apparatus and methods for patient management include, but are not limited to, the teachings provided in the patent application entitled: Method and Apparatus for Establishing Context Among Events and Optimizing Implanted Medical Device Performance, U.S. patent application Ser. No. 10/093,353, filed Mar. 6, 2002, which is incorporated by reference in its entirety.

Variations in design and placement of elements may be implemented without departing from the teachings provided herein, and the examples given are not intended in a limited or exclusive sense.

Figure 5:
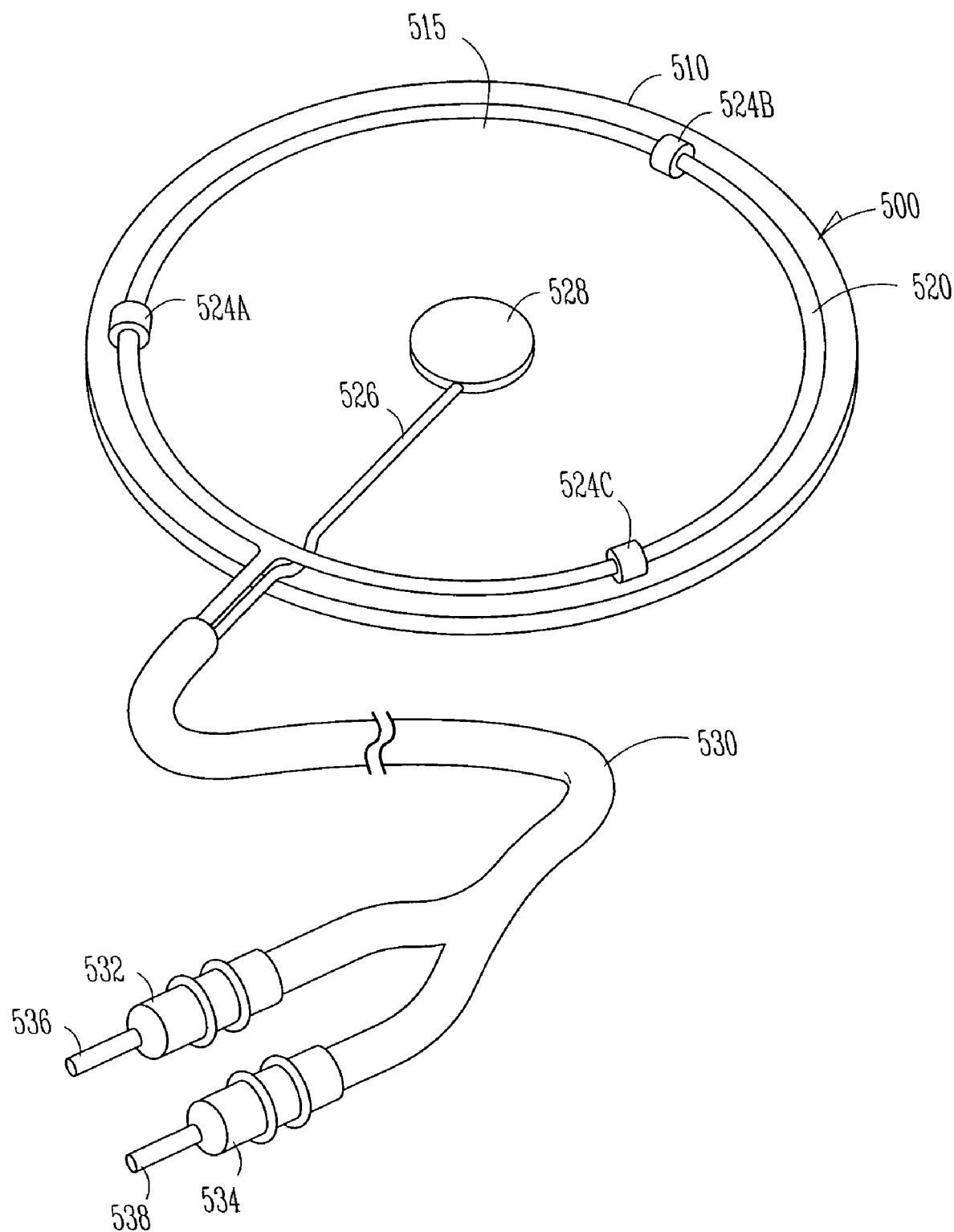
FIG. 5 is an illustration of one embodiment of an epicardial patch which includes electrodes and an isolated ECM support.

FIG. 5 is an illustration of one embodiment of an epicardial patch 500 integrating isolated ECM support 510 and pacing electrodes 524A-C and 528. Isolated ECM support 510 generally defines the shape of epicardial patch 500, which is configured for being attached to the epicardial surface of a heart. In one embodiment, epicardial patch 500 is sutured to the epicardial surface for a stable attachment. Isolated ECM support 510 includes an attachment surface 515 that is configured for epicardial attachment over the myocardial region including at least portions of the injured area, such as a myocardial infarcted area. In one embodiment, isolated ECM support 510 has an approximately circular shape with a diameter in a range from approximately 10 mm to approximately 150 mm, with 30 mm being a specific example. In one embodiment, isolated ECM support 510 has a thickness in a range from approximately 0.5 mm to approximately 2 mm, with 1 mm being a specific example. In one embodiment, versions of epicardial patch 500 with difference sizes and/or shapes are made available for selection or otherwise modified, e.g., using a scalpel or scissors, based on the general size and shape of individual injured myocardial areas. Preferably, a version of epicardial patch 500 is selected and/or modified to cover substantially the entire injured area. In one embodiment, a version of epicardial patch 500 is selected to provide an isolated ECM support having an attachment surface covering substantially the entire injured area. In another embodiment, a version of epicardial patch 500 is selected to provide an isolated ECM support having an attachment surface covering substantially the entire injured area and substantial portions of myocardial tissue surrounding the injured area.

Electrodes 524A-C and 528 are integrated into isolated ECM support 510 to allow pacing pulses to be delivered to the myocardial region. In one embodiment, electrodes 524A-C and 528 are configured to provide the myocardial region with approximately uniform unloading and stress reduction during at least a portion of each cardiac cycle by pacing. In one embodiment, a distal end portion of a conductor 520 forms a loop near the circumference of isolated ECM support 510. Electrodes 524A-C are peripheral electrodes approximately evenly distributed along the loop and are electrically connected to conductor 520. A proximal end of conductor 520 is connected to a conductive terminal pin 536. Electrode 528 is a center electrode attached to approximately the center of isolated ECM support 510. A distal end portion of a conductor 526 is electrically connected to electrode 528. A proximal end of conductor 526 is connected to a conductive terminal pin 538. A major portion of conductor 520 and a major portion of conductor 526 physically join to form a lead 530 having an outer shell made of insulating material such as silicone or polyurethane. In one embodiment, a biological primer is applied to (such as spread onto or deposited into) the insulating material to minimize histological reactions when in contact of ECM support 510. Generally, the biological primer is applied to any component that is made of materials such as silicone or polyurethane and is in direct contact with ECM support 510. Lead 530 has a distal end portion connected to isolated ECM support 510 and, in one embodiment, a branched proximal end portions connected to a lead connector 532 that includes terminal pins 536 and a lead connector 534 that includes terminal pin 538. Terminal pins 536 and 538 mechanically connect epicardial patch 500 to the implantable medical device through lead 530 and electrically connect electrodes 524A-C and 528 to the implantable medical device. In an alternative embodiment, lead connectors 532 and 534 are integrated into a single multi-conductor connector. In another alternative embodiment, conductors 520 and 526 are separately insulated to form two leads each connected to a lead connector having a terminal pin.

In one embodiment, electrodes 524A-C, the distal end portion of conductor 520, electrode 528, and the distal end portion of conductor 526 are attached to attachment surface 515 of isolated ECM support 510. Methods for attaching the electrodes and the portions of the conductors to attachment surface 515 include, but are not limiting to, stapling, suturing, and gluing. In another embodiment, electrodes 524A-C, the distal end portion of conductor 520, electrode 528, and the distal end portion of conductor 526 are embedded in isolated ECM support 510. In one specific embodiment, isolated ECM support 510 is formed by at least two layers of biological material. The electrodes and the portions of the conductors are laid on a first layer, and a second layer is overlaid onto the first layer over the electrodes and the portions of the conductors.

In one embodiment, conductors 520 and 526 each include a coiled multifilar wire made of material such as stainless steel, stainless steel alloys, MP35N, titanium, or tantalum. The distal end portions of conductors 520 and 526, which are attached to or embedded in isolated ECM support 510, are each insulated with an insulating layer made of material such as silicone or polyurethane. In one embodiment, electrodes 524A-C are electrode collars constructed along the distal end portion of conductor 520. Except for the portions connecting to the electrode collars, the distal end portion of conductor 520 is insulated with the insulation layer. In one embodiment, terminal pins 536 and 538 are each made of material such as stainless steel, titanium, and platinum-iridium.

In an alternative embodiment, electrodes 524A-C are individually connected to the implantable medical device through separate conductors, such that the delivery of the pacing pulses to each electrode can be individually controlled. In another alternative embodiment, isolated ECM support 510 has a contour that is not approximately circular. The distal end portion of conductor 520 forms a loop having a shape approaching the contour such that electrodes 524A-C are distributed in or on isolated ECM support 510 near its contour.

Figure 6:
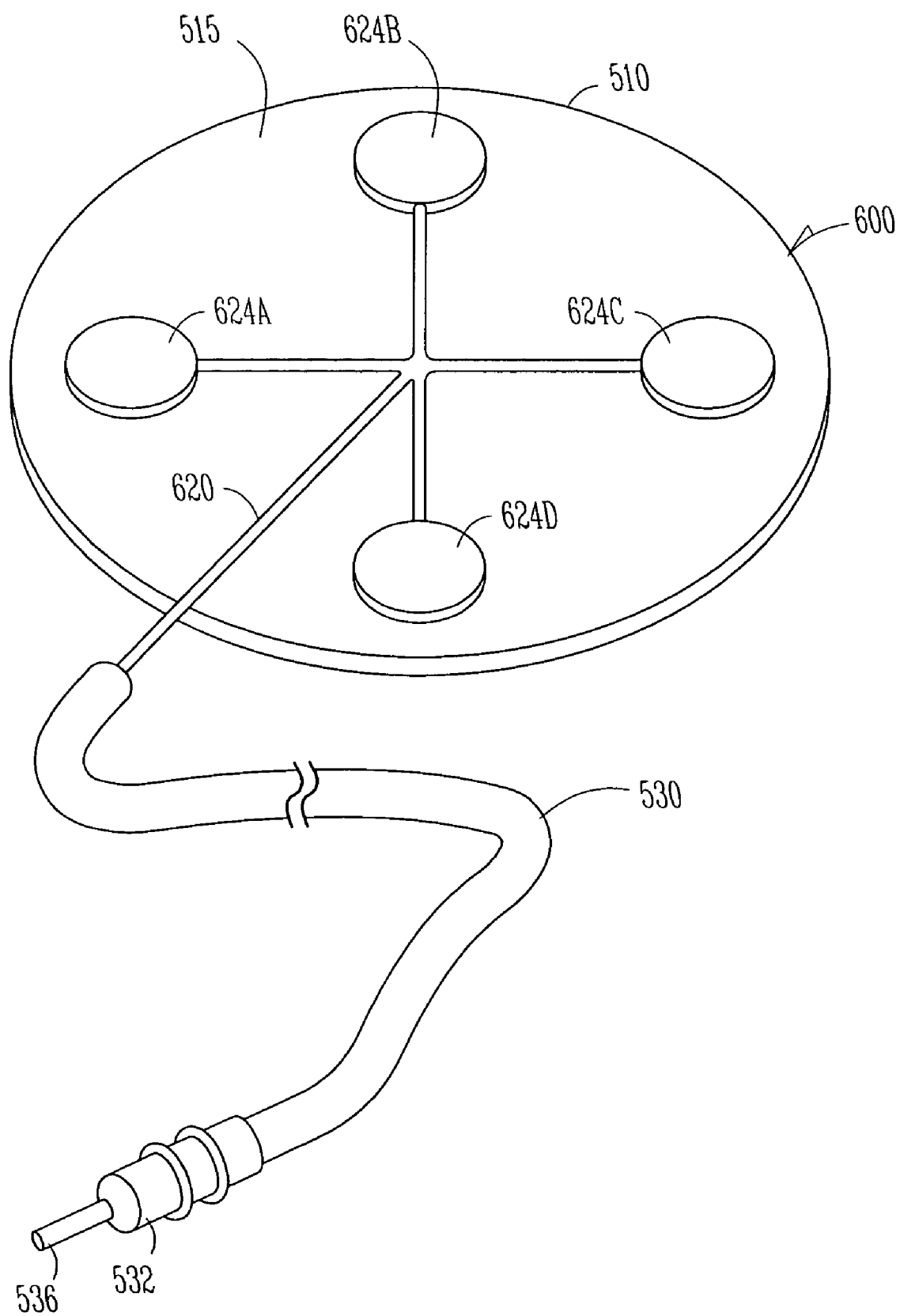
FIG. 6 is an illustration of one embodiment of another epicardial patch.

FIG. 6 is an illustration of one embodiment of an epicardial patch 600 integrating isolated ECM support 510 and pacing electrodes 624A-D. Electrodes 624A-D are approximately evenly distributed in or on isolated ECM support 510 near its circumference or contour. A conductor 620 includes a distal end portion that branches out as shown to connect to electrodes 624A-D and a proximal end connected to terminal pin 536.

Figure 7:
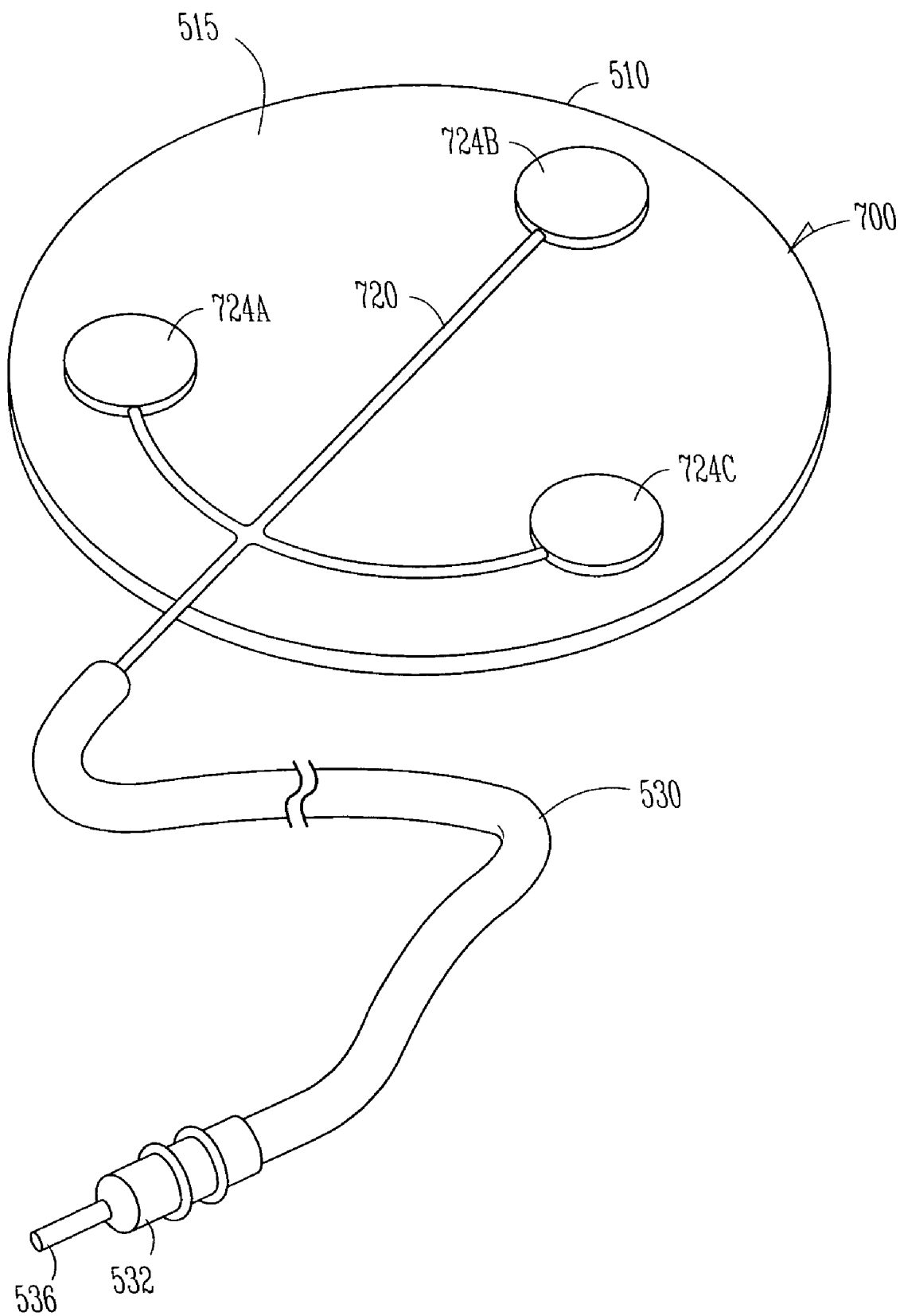
FIG. 7 is an illustration of one embodiment of another epicardial patch.

FIG. 7 is an illustration of one embodiment of an epicardial patch 700 integrating isolated ECM support 510 and pacing electrodes 724A-C. Electrodes 724A-C are approximately evenly distributed in or on isolated ECM support 510 near its circumference or contour. A conductor 720 includes a distal end portion that branches out as shown to connect to electrodes 724A-C and a proximal end connected to terminal pin 536.

Epicardial patches 500, 600, and 700 are each an example of the configuration of an epicardial patch including isolated ECM integrated with electrodes for electrical stimulation for treating a myocardial injury. FIGS. 5-7 are intended to be illustrative, but not restrictive. Electrical stimulation such as cardiac pacing can be delivered to the myocardial region including at least the portions of the injured area by using other electrode configurations. In various embodiments, the epicardial patch may incorporate different numbers and/or configurations of electrodes, conductors, lead, and lead connectors, including modifications and combinations of the embodiments discussed above. In one embodiment, the electrodes and portions of the conductors are attachment onto a surface of an isolated ECM support. In another embodiment, the electrodes and portions of the conductors are embedded in an isolated ECM support.

Figure 8:
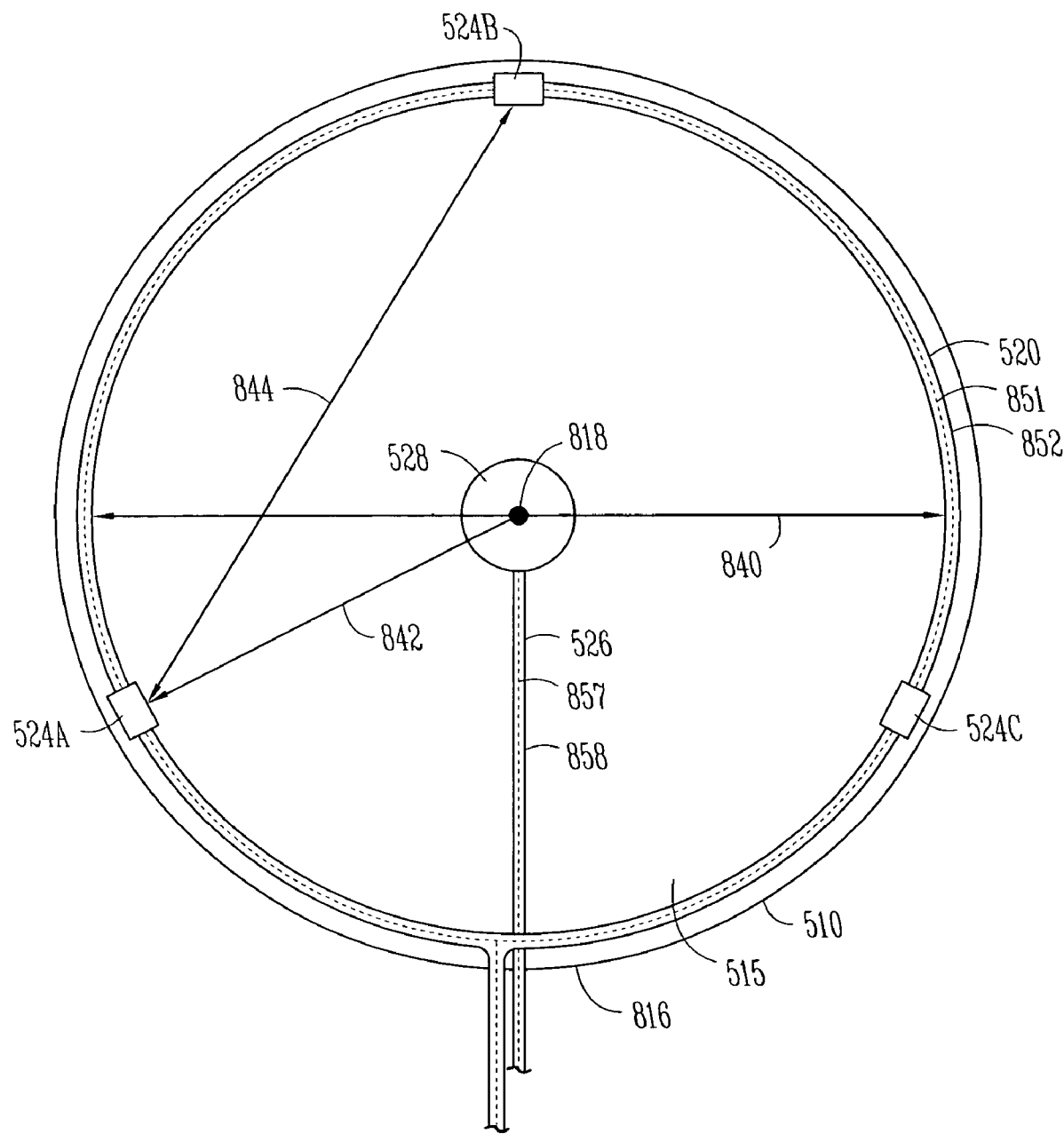
FIG. 8 is an illustration of one specific embodiment of the epicardial patch of FIG. 1.

FIG. 8 is an illustration of one specific embodiment of epicardial patch 500. In this specific embodiment, isolated ECM support 510 includes a circular attachment surface 515 having a circumference 816 and a center 818. The distal end portion of conductor 520 is attached onto attachment surface 515 and forms a circular loop near circumference 816. The circular loop is centered at center 818 and has a diameter 840. Diameter 840 is within a range approximately between 10 mm and 150 mm, with approximately 35 mm being a specific example. Electrodes 524A-C are approximately evenly distributed along the circular loop formed by the distal end portion of conductor 520 and are electrically connected to conductor 520. In various embodiments, electrodes 524A-C are collar electrodes, patch electrodes, or electrodes in any other suitable geometrical configuration. The distal end portion of conductor 526 is attached onto attachment surface 515 and is electrically connected to electrode 528, which is approximately centered at center 818. A distance 842 between the center of electrode 528 and the center of any one of electrodes 524A-C approximately equals the radius of the circuit loop, i.e., within a range approximately between 5 mm and 75 mm, with approximately 17.5 mm being a specific example. A distance 844 between any two of electrodes 524A-C is within a range approximately between 8 mm and 130 mm, with approximately 30.31 mm being a specific example.

In one embodiment, electrodes 524A-C are each made of a platinum/iridium alloy (such as an alloy of 90% platinum and 10% iridium) and coated with iridium oxide (IROX). A thin film of silicone is provided between each of electrodes 524A-C and attachment surface 515. Conductor 520 includes a coiled stainless steel wire or braid 851 insulated by insulation layer 852 made of silicone.

In one embodiment, electrode 528 is made of the platinum/iridium alloy and coated with IROX. A thin film of silicone is provided between center electrode 528 and attachment surface 515. Conductor 526 includes a coiled stainless steel wire or braid 857 insulated by insulation layer 858 made of silicone. In one embodiment, electrode 528 includes a fixation device. In one specific embodiment, electrode 528 includes a helix configured for screwing into epicardial tissue to provide for a stable attachment of epicardial patch 500 onto the myocardial region. In another specific embodiment, electrode 528 includes a disk electrode. The disk electrode includes two or more holes allowing for suturing the disk electrode onto epicardial tissue. The disk electrode has a surface area between approximately 1 $mm^2$ and 30 $mm^2$, with approximately 17.8 $mm^2$ being a specific example. In another embodiment, electrode 528 includes a ring electrode with a surface area between approximately 1 $mm^2$ and 20 $mm^2$, with approximately 13.8 $mm^2$ being a specific example.

Figure 9:
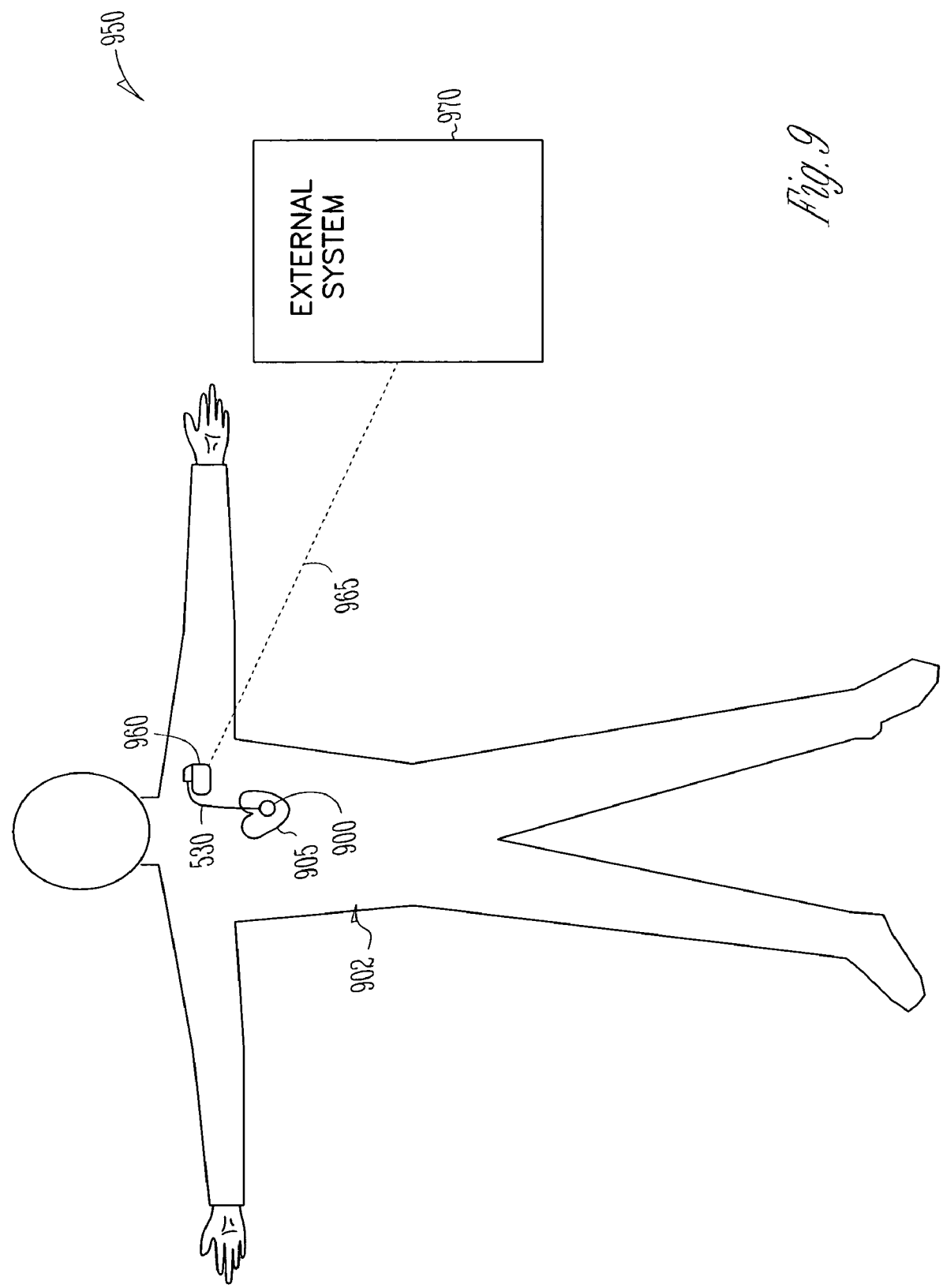
FIG. 9 is an illustration of an embodiment of a CRM system and portions of an environment in which the system is used.

FIG. 9 is an illustration of an embodiment of a CRM system 950 and portions of an environment in which system 950 is used. System 950 includes epicardial patch 900, an implantable medical device 960, an external system 970, and a wireless telemetry link 965. Epicardial patch 900 includes a plurality of pacing electrodes integrated with an isolated ECM configured for epicardial attachment. Examples of epicardial patch 900 include, but are not limited to, epicardial patches 500, 600, and 700. Wireless telemetry link 965 wirelessly couples the implantable medical device 960 and external system 970.

After implantation, implantable medical device 960 operates within a body 902 to sense activities of a heart 905 and deliver one or more therapies to heart 905. Implantable medical device 960 includes, but is not limited to, one or more of a pacemaker, a cardioverter/defibrillator, a cardiac resynchronization therapy (CRT) device, a cardiac remodeling control therapy (RCT) device, or any other medical device providing for cardiac pacing. Implantable medical device 960 includes a pacing circuit to deliver pacing pulses to heart 905 through at least the electrodes of epicardial patch 900 and a pacing controller to control the parameters of the pacing pulses and their delivery. In one embodiment, the pacing controller controls the pacing delivery by executing an RCT pacing algorithm. The RCT pacing algorithm is designed to reduce the loading and stress on cardiac wall during at least portions of each cardiac cycle, such as by delivering pacing pulses to pre-excite the myocardial region before the systolic phase of each cardiac cycle begins. In another embodiment, the pacing controller controls the pacing delivery by executing a CRT pacing algorithm. The CRT pacing algorithm is designed to restore synchrony in cardiac contractions. In a further embodiment, the pacing controller controls the pacing delivery by alternately executing the RCT pacing algorithm and the CRT pacing algorithm based on a patient's changing needs and conditions.

External system 970 communicates with implantable medical device 960 through telemetry link 965. It allows a physician or other caregiver to control implantable medical device 960 and monitor the patient through implantable medical device 970. In one embodiment, external system 970 includes an external programmer. In another embodiment, external system 970 is a patient management system including an external device, a telecommunication network, and a remote device. The external device is placed within the vicinity of implantable medical device 960 and communicates with implantable medical device 960 bi-directionally via telemetry link 965. The remote device is in a remote location and communicates with the external device bi-directionally through the telecommunication network, thus allowing the physician or other caregiver to monitor and treat the patient from a distant location.

Telemetry link 965 provides for bi-directional communications between implantable medical device 960 and external system 970. In one embodiment, telemetry link 965 is an inductive telemetry link. In an alternative embodiment, telemetry link 965 is a far-field radio-frequency telemetry link. Telemetry link 965 provides for data transmission from implantable medical device 960 to external system 970. This may include, for example, transmitting real-time physiological data acquired by implantable medical device 960, extracting physiological data acquired by and stored in implantable medical device 960, extracting therapy history data, and extracting data indicating an operational status (e.g., battery status and lead impedance). The physiological data represent signals acquired by implantable medical device 960. In one embodiment, such signals include one or more electrograms sensed through the electrodes of epicardial patch 900. Telemetry link 965 also provides for data transmission from external system 970 to implantable medical device 960. This may include, for example, parameters for programming implantable medical device 960 to acquire physiological data, to perform at least one self-diagnostic test (such as for a battery status and lead impedance status), and/or to deliver at least one electrical therapy including cardiac pacing delivered through the electrodes of epicardial patch 900.

In one embodiment, implantable medical device 960 includes a hermetically sealed can to house at least portions of its circuit. At least a portion of the can is used as a can electrode. A header, which includes connectors to mate at least connector 536 and/or connector 538, is attached to the can. In one embodiment, a header electrode is incorporated onto the header. The can electrode and the header electrode are each used as a reference electrode for sensing electrograms and/or delivering pacing pulses. In one embodiment, implantable medical device 960 includes a programmable electrode interface circuit providing for electrical connections between the pacing circuit and pacing electrodes and electrical connections between the sensing circuit and sensing electrodes. The pacing and sensing electrodes are selected from at least the electrodes of epicardial patch 900, the can electrode, and the header electrode. In one embodiment, additional leads with electrodes are connected to implantable medical device 960 for sensing from and/or delivering pacing pulses to myocardial regions other than the myocardial region onto which epicardial patch 900 is attached. The pacing controller includes an electrode configuration controller to control the programmable electrode interface circuit in making the electrical connections. In one embodiment, the electrode configuration controller includes an electrode selector to select the pacing and sensing electrodes from at least the electrodes of epicardial patch 900, the can electrode, and the header electrode. In a further embodiment, the electrode configuration controller includes an electrode polarity controller to assign each of the selected pacing and sensing electrodes as one of a cathode and an anode. The pacing and sensing are each performed with either a bipolar electrode configuration, such as through one or more pairs of electrodes selected from the electrodes of epicardial patch 900, or with a unipolar configuration, such as through one or more electrodes selected from the electrodes of epicardial patch 900 and one of the can electrode and the header electrode.

Figure 10:
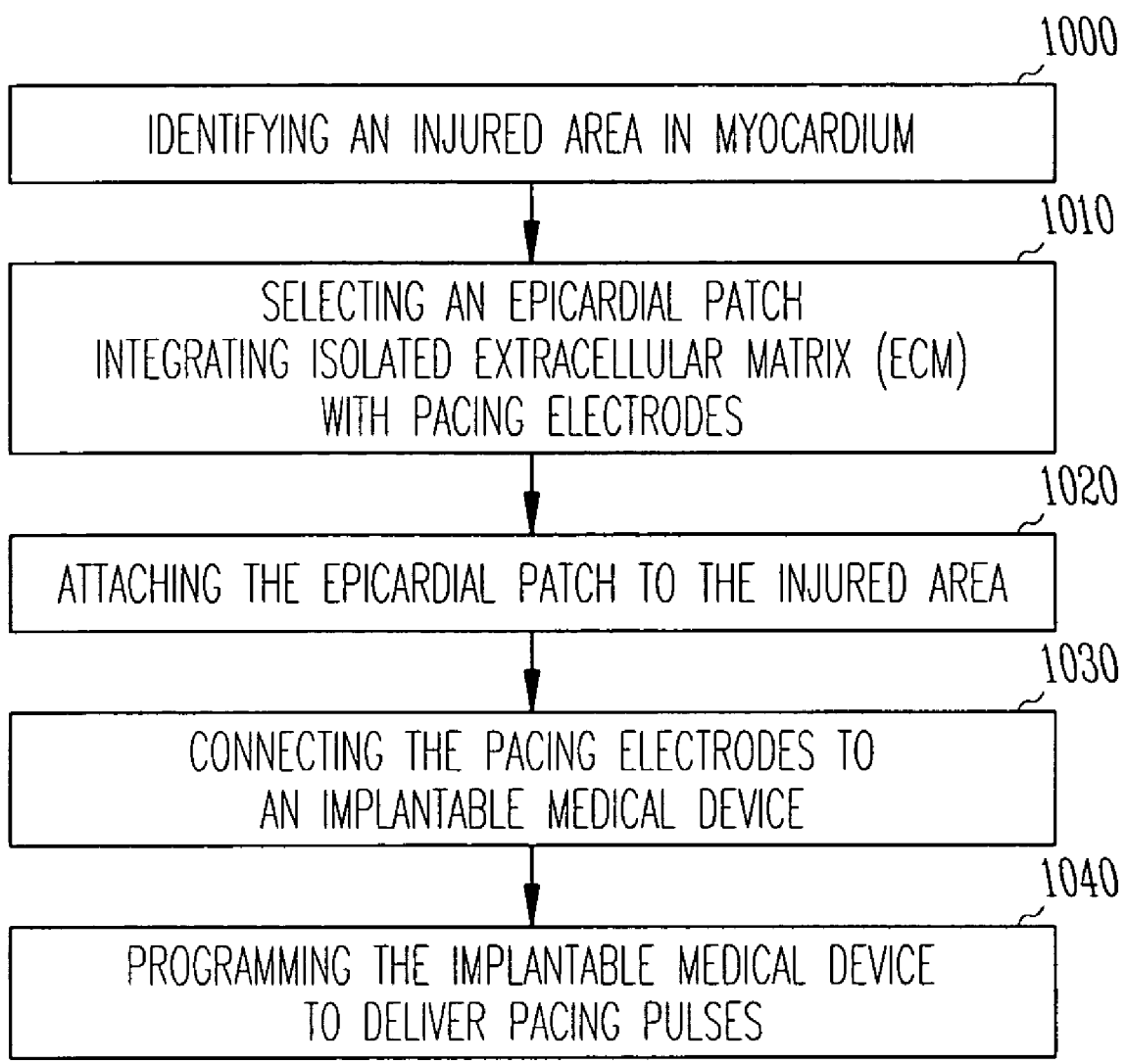
FIG. 10 is a flow chart illustrating a method for delivering combined ECM support and electrical stimulation therapies.

FIG. 10 is a flow chart illustrating a method for delivering combined isolated ECM and electrical stimulation therapies to the myocardial region including at least the portions of the injured area. In one embodiment, the method is performed with CRM system 950 including epicardial patch 900.

The injured area is identified at 1000. The identification includes locating the injured area and assessing the size and/or shape of the injured area. An epicardial patch including isolated ECM integrated with a plurality of pacing electrodes is selected at 1010. In one embodiment, the epicardial patch is selected from pre-manufactured epicardial patches of different sizes and/or shapes based on an approximate size and/or the shape of the injured area as assessed. The selected epicardial patch is attached to the epicardium over at least the portions of the injured area constituting the myocardial region at 1020. The plurality of pacing electrodes of the epicardial patch is connected to an implantable medical device at 1030. The implantable medical device is programmed to deliver pacing pulses to the heart through one or more electrodes of the plurality of pacing electrodes at 1040.

In one embodiment, the implantable medical device is programmed to deliver pacing pulses to approximately uniformly reduce loading and stress on the myocardial region including at least the portions of the injured area, onto which the epicardial patch is attached. In one embodiment, the programming includes configuring pacing electrodes. The pacing electrodes are selected from the plurality of pacing electrodes of the epicardial patch and one or more reference electrodes on the implantable medical device. In one embodiment, the plurality of pacing electrodes of the epicardial patch includes at least a center electrode and a plurality of peripheral electrodes. In specific embodiment, a bipolar electrode configuration is programmed for delivering the pacing pulses through an anode being the center electrode and one or more cathodes each being one of the peripheral electrodes. In another specific embodiment, a bipolar electrode configuration is programmed for delivering the pacing pulses through a cathode being the center electrode and one or more anodes each being one of the peripheral electrodes. In another embodiment, a unipolar electrode configuration for delivering the pacing pulses through one of the plurality of pacing electrodes of the epicardial patch and one of the one or more reference electrodes.

Figure 11:
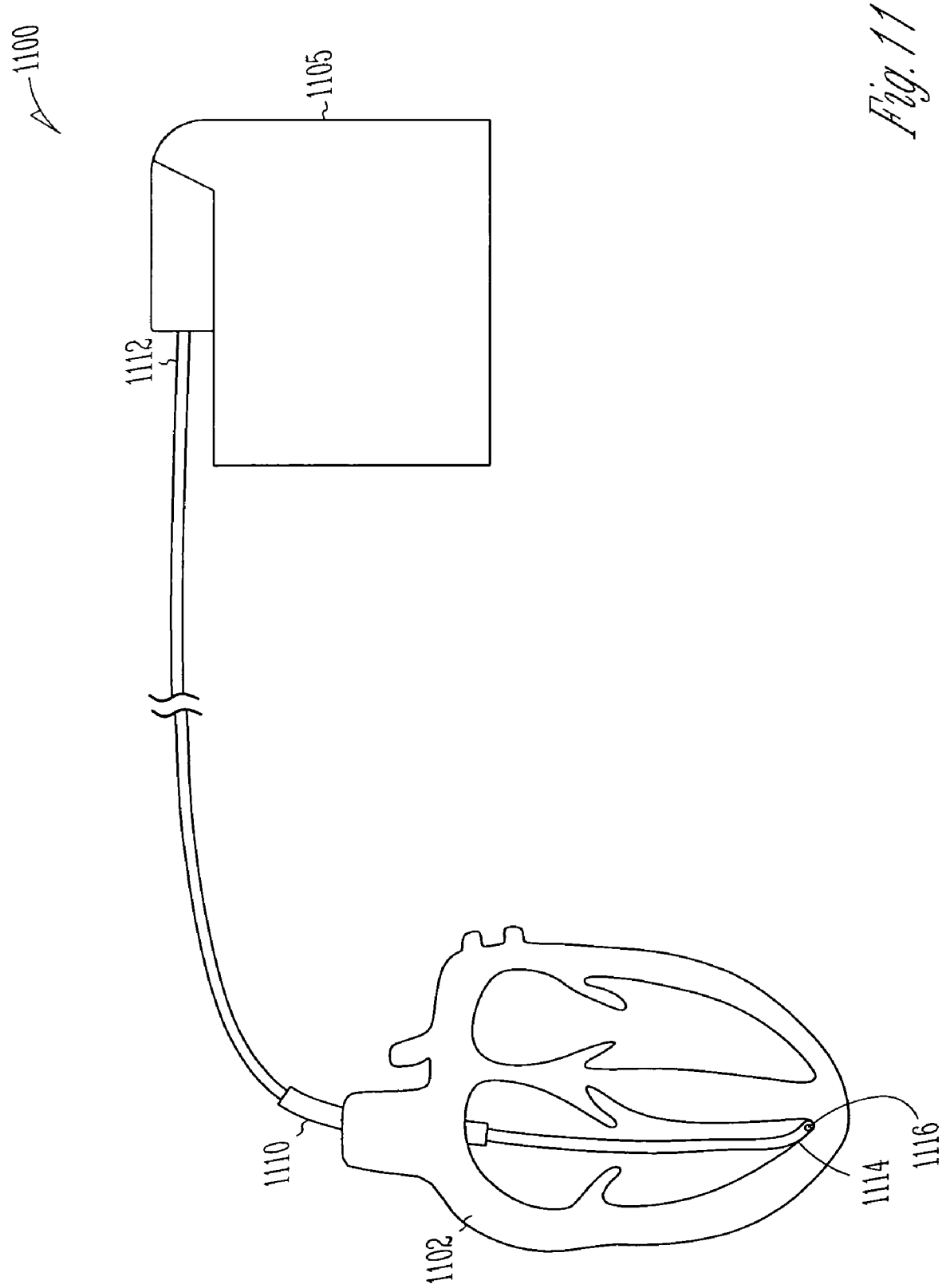
FIG. 11 illustrates a block diagram of an assembly constructed in accordance with at least one embodiment.

In one example of a medical device, a lead assembly includes a lead 1110 including one or more electrodes 1116. FIG. 11 illustrates one example of a lead 1110 and a lead system 1100, where the system 1100 can be used for delivering and/or receiving electrical pulses or signals to stimulate and/or sense the heart 1102. The system 1100 optionally includes a pulse generator 1105 and a lead 1110. The pulse generator 1105 includes a source of power, as well as an electronic circuitry portion. The pulse generator 1105 further includes and/or optionally includes electronics to sense and/or receive electronic pulses from the heart 1102, for example, transmitted through the lead 1110. In one example, the electronic circuitry portion includes a pacing circuit configured to deliver pacing pulses to electrodes and to the heart and/or tissue. In another example, the electronic circuitry portion includes a sensing circuit configured to receive sensed electronic signals from the electrode.

The pulse generator 1105, in one option, is a battery powered device which generates a series of timed electrical discharges or pulses. The pulse generator 1105 is generally implanted into a subcutaneous pocket made in the wall of the chest. Alternatively, the pulse generator 1105 is placed in a subcutaneous pocket made in the abdomen, or in other locations. In yet another option, the pulse generator 1105 can be located external to a body.

The lead 1110 extends from a proximal end 1112, where it is coupled with the pulse generator 1105, for example, with a connector. The lead 1110 extends also to a distal end 1114, which can be coupled with a portion of the heart 1102, for example when implanted endocardially. Disposed between the distal end 1114 and the proximal end 1112 of the lead 1110 includes an intermediate portion. Optionally, the intermediate portion of the lead 1110 can be used to couple the lead 1110 with a portion of the heart 1102 and/or vasculature of a patient. Disposed along a portion of the lead 1110 is at least one electrode 1116. For example, the electrode 1116 can be disposed near a distal end 1114 of the lead 1110, along the intermediate portion of the lead 1110, and/or near a proximal end 1112 of the lead 1110. Multiple electrodes 1116 can also be disposed along the lead 1110 including near the distal end 1114, the proximal end 1112, and/or along the intermediate portion of the lead 1110.

The at least one electrode 1116 can be in a number of different forms. For example, in one option, the at least one electrode 1116 forms a helix at the distal end 1114 of the lead 1110. In another option, the at least one electrode 1116 includes a porous surface, such as a micro porous surface. In another option, the pulse generator 1105, which houses the electronic circuitry as discussed above, is formed of a metal housing and forms a reference electrode.

The electrode 1116 allows for the lead 1110 to be electrically coupled with the heart 1102, and allows for the electrical signals to be transmitted from the pulse generator 1105 to the electrode 1116, and to the heart 1102. In another option, the lead 1110 further includes at least one electrical conductor that can be disposed within the lead 1110, for example, within a lead body. The electrical conductor is electrically coupled with the electrode 1116, and is one example of how electrical signals can be transmitted between the pulse generator 1105 and the electrode 1116.

Figure 12:
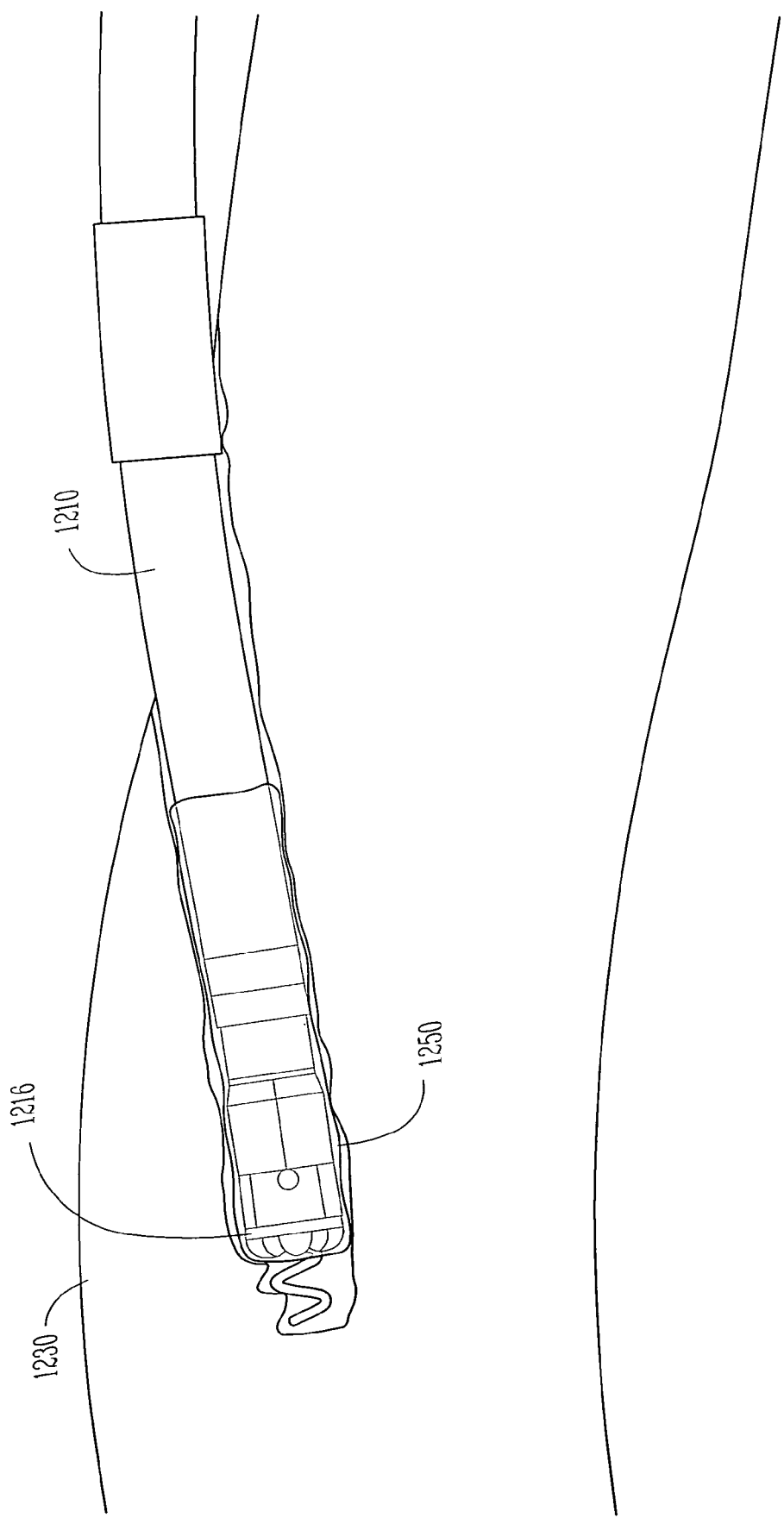
FIG. 12 illustrates a portion of an assembly constructed with in accordance with at least one embodiment.

FIG. 12 illustrates another embodiment of a lead 1210. The lead 1210 includes a lead body and an electrode 1216 that is disposed near tissue, or can be implanted within tissue 1230, as illustrated in FIG. 12. The lead 1210 includes isolated ECM 1250 associated therewith. The isolated ECM is disposed along a portion of the lead 1210, for example, along a portion of the electrode 1216.

The isolated ECM 1250 can be associated with the lead 1210, the lead body, and/or the electrode 1216 in a number of manners, such as disposing the isolated ECM along a portion of the electrode 1216. For example, the isolated ECM 1250 can be attached and/or secured with at least a portion of the electrode 1216 or the lead body. In another example, the isolated ECM 1250 is coated on at least a portion of the electrode 1216 or the lead body, for example a surface of the electrode such as a microporous surface of the electrode 1216, or a surface of the lead body. In another option, the isolated ECM 1250 is embedded with a portion of the electrode 1216 and/or the lead body.

The isolated ECM 1250 can be disposed along, or placed proximal to an electrode 1216 in a number of different manners. For example, the isolated ECM can be coated on the electrode. Alternatively, the isolated ECM can be attached to or about the electrode with one or more types of mechanical fasteners or mechanical fastening procedure, chemical fastening procedures, or otherwise operably associated with the electrode 1216. In an example of a mechanical fastener, anchoring devices such as projections including, but not limited to, plastic or metal pins, sutures, or other fixation devices can be included. In another example mechanical fixation, the isolated ECM is disposed about the electrode. For example, can be provided in a sheet form and wrapped around the electrode 1216, and redundant tissue can be gathered such that the isolated ECM can be secured via sutures. In yet another option, multiple sheets of the isolated ECM can be gathered attached, or secured together before, during or after attachment to the medical device, using for example, surgically acceptable techniques, e.g., suturing, gluing, stapling or compressing on, about, or within the electrode and/or the isolated ECM. These techniques can also be used to dispose, place, or associate the isolated ECM 1250 along or with the lead body.

The isolated ECM 1250 can take a number of different forms, and/or a combination of one or more of the following forms. For example, the isolated ECM can take the form of a solid sheet, a strip or loop of isolated ECM. In another option, the isolated ECM can be fluidized or placed in a coating form. In yet another option, the isolate ECM may be in a particulate form, and/or a gel form. In yet another option, the isolated ECM can be applied to the medical device and subsequently lyophilized to form a coating. Still further, in another option, the isolated ECM can be placed on the lead body electrode or disposed along the electrode in a form of a coating. In another option, multi-laminate constructs may be formed by overlapping individual strips or other forms of isolated ECM and applying pressure to the overlapped portions to fuse the strips together. Other processes for fusing the forms of isolated ECM can be used as well. In one embodiment, pressure is applied to the overlapped strips under conditions allowing dehydration of the isolated ECM.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method comprising affixing an isolated extracellular matrix (ECM) sheet including isolated ECM having a native three dimensional microstructure to an electrode in an amount effective to inhibit fibrotic capsule formation and/or enhance excitable tissue formation around a lead comprising the electrode after implantation of the lead.

2. The method of claim 1, wherein the isolated ECM is affixed to the surface of the electrode.

3. The method of claim 1, wherein donor cells and/or one or more cytokines are contacted with the isolated ECM sheet after affixing the isolated ECM to the electrode.

4. The method of claim 3, wherein one cytokine is G-CSF, SCF, HGF or IGF.

5. The method of claim 1, wherein donor cells and/or one or more cytokines are contacted with the isolated ECM sheet prior to affixing the isolated ECM to the electrode.

6. The method of claim 5, wherein one cytokine is G-CSF, SCF, HGF or IGF.

7. The method of claim 3 or 5, wherein the donor cells are stem cells.

8. The method of claim 3 or 5, wherein the donor cells are autologous cells.

9. The method of claim 3 or 5, wherein the donor cells are bone marrow-derived cells.

10. The method of claim 3 or 5, wherein the donor cells are mesenchymal cells.

11. The method of claim 1, wherein the ECM is isolated from small intestine submucosa or urinary bladder submucosa.

12. The method of claim 1 wherein the isolated ECM is xenogeneic.

13. The method of claim 1, wherein the isolated ECM is decellularized.

14. The method of claim 1, wherein the isolated ECM is allogeneic.

15. The method of claim 1, further comprising affixing an isolated ECM sheet to a portion of a surface of the lead body.

16. The method of claim 1 wherein the isolated ECM sheet has a thickness of approximately 50 microns to 80 microns.

17. The method of claim 1 wherein the isolated ECM sheet comprises a rinsed and mechanically delaminated portion of small intestine or urinary bladder.

\* \* \* \* \*